United States Patent
Stampfer et al.

(10) Patent No.: US 10,689,652 B2
(45) Date of Patent: Jun. 23, 2020

(54) METHODS FOR IMMORTALIZATION OF EPITHELIAL CELLS

(71) Applicant: The Regents of the University of California, Oakland, CA (US)

(72) Inventors: Martha R. Stampfer, Oakland, CA (US); James C. Garbe, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/256,395

(22) Filed: Sep. 2, 2016

(65) Prior Publication Data

US 2017/0130232 A1     May 11, 2017

Related U.S. Application Data

(63) Continuation-in-part of application No. 14/505,491, filed on Oct. 2, 2014, now abandoned.

(60) Provisional application No. 61/886,021, filed on Oct. 2, 2013, provisional application No. 62/238,029, filed on Oct. 6, 2015.

(51) Int. Cl.
| | |
|---|---|
| *C12N 15/85* | (2006.01) |
| *C12N 15/113* | (2010.01) |
| *C12N 15/62* | (2006.01) |
| *G01N 33/50* | (2006.01) |
| *C12N 5/09* | (2010.01) |
| *C12N 5/071* | (2010.01) |

(52) U.S. Cl.
CPC ........ *C12N 15/1137* (2013.01); *C12N 5/0631* (2013.01); *C12N 5/0693* (2013.01); *C12N 15/1136* (2013.01); *C12N 15/62* (2013.01); *G01N 33/5011* (2013.01); *G01N 33/5014* (2013.01); *G01N 33/5044* (2013.01); *C12N 2310/14* (2013.01); *C12N 2501/606* (2013.01); *C12N 2510/04* (2013.01)

(58) Field of Classification Search
None
See application file for complete search history.

(56) References Cited

U.S. PATENT DOCUMENTS

| | | |
|---|---|---|
| 2006/0286552 A1 | 12/2006 | Goldsmith et al. |
| 2010/0022000 A1 | 1/2010 | Stampfer et al. |
| 2010/0280134 A1 | 11/2010 | Renard et al. |
| 2012/0270317 A1 | 10/2012 | Harper et al. |
| 2013/0011920 A1 | 1/2013 | Zhou |
| 2013/0252835 A1 | 9/2013 | Koh et al. |

FOREIGN PATENT DOCUMENTS

| | | |
|---|---|---|
| WO | 98/37181 A2 | 8/1998 |
| WO | 2014/020048 A1 | 2/2014 |

OTHER PUBLICATIONS

Freimuth, R.R., et al., "Human cytosolic sulfotransferase database mining: identification of seven novel genes and pseudogenes," The Pharmacogenomics Journal (2004) 4(1):54-65.
Kiyono, T., et al., "Both Rb/p16INK4a inactivation and telomerase activity are required to immortalize human epithelial cells," Nature (1998) 396:84-88.
Romanov, S.R., et al., "Normal human mammary epithelial cells spontaneously escape senescence and acquire genomic changes," Nature (2001) 409:633-637.
Shamanin, V.A., et al., "hAda3 Degradation by Papillomavirus Type 16 E6 Correlates with Abrogation of the p14ARF-p53 Pathway and Efficient Immortalization of Human Mammary Epithelial Cells," Journal of Virology (2008) 82(80):3912-3920.
Ulbricht, U., et al., "Isogenic human mammary epithelial cell lines: novel tools for target identification and validation," Breast Cancer Res. Treat (2013) 138:437-456.

*Primary Examiner* — Celine X Qian
(74) *Attorney, Agent, or Firm* — Brian E. Davy; Bozicevic, Field & Francis LLP

(57) ABSTRACT

Methods for inducing non-clonal immortalization of normal epithelial cells by directly targeting the two main senescence barriers encountered by cultured epithelial cells. In finite lifespan pre-stasis human mammary epithelial cells (HMEC), the stress-associated stasis barrier was bypassed, and in post-stasis HMEC, the replicative senescence barrier, a consequence of critically shortened telomeres, was bypassed. Early passage non-clonal immortalized lines exhibited normal karyotypes. Methods of efficient HMEC immortalization, in the absence of "passenger" genomic errors, should facilitate examination of telomerase regulation and immortalization during human carcinoma progression, methods for screening for toxic and environmental effect on progression, and the development of therapeutics targeting the process of immortalization.

9 Claims, 39 Drawing Sheets

Specification includes a Sequence Listing.

p53/DDR(+) stasis can be overcome with loss of p53 function, giving viable post-stasis cells

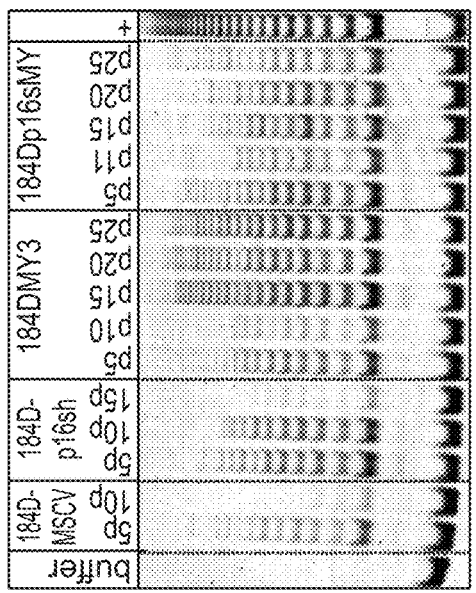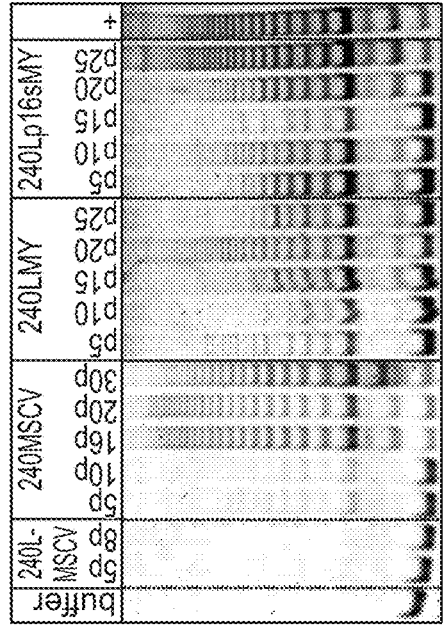
FIG. 6A
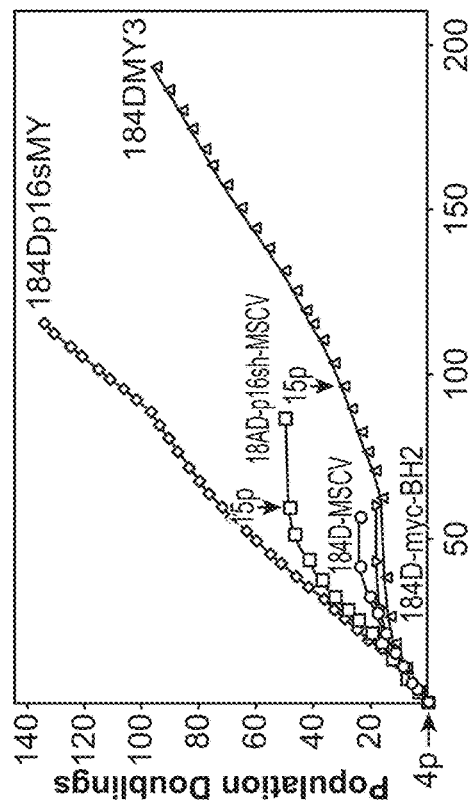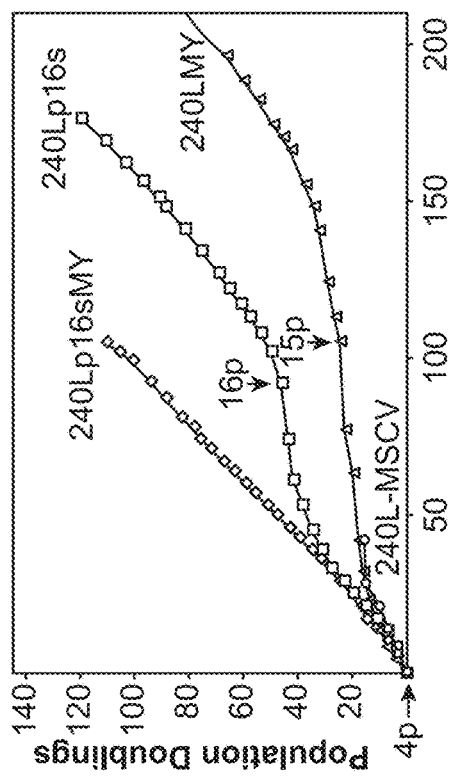
FIG. 6B

FIG. 7A        FIG. 7B
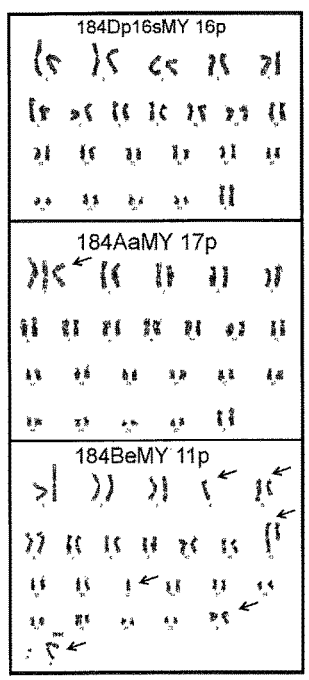
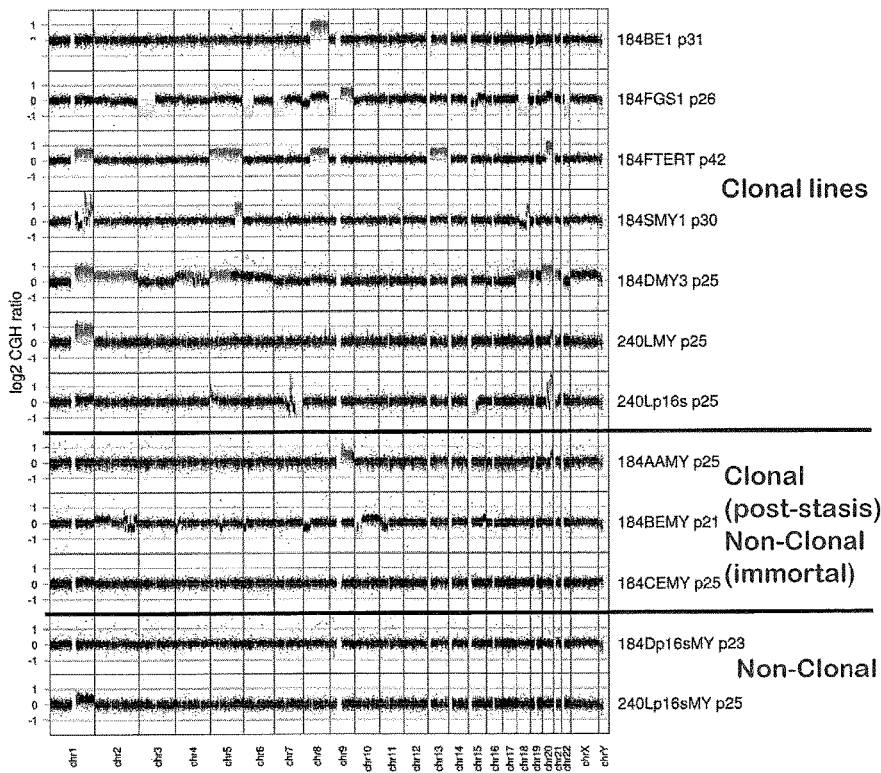

|  | Chromosome # | | | |
| --- | --- | --- | --- | --- |
| Cell # | 122Lp16sMY | 122LD1MY | 240LD1MY | 805p16sMY |
| 1 | 93 | 45 | 46 | 46 |
| 2 | 46 | 46 | 46 | 46 |
| 3 | 45 | 46 | 46 | 46 |
| 4 | 46 | 46 | 46 | 46 |
| 5 | 46 | 46 | 46 | 46 |
| 6 | 46 | 46 | 46 | 46 |
| 7 | 46 | 44 | 43 | 46 |
| 8 | 46 | 46 | 46 | 45 |
| 9 | 45 | 46 | 46 | 46 |
| 10 | 46 | 45 | 46 | 46 |
| 11 | 46 | 46 | 46 | 92 |
| 12 | 46 | 46 | 45 | 45 |
| 13 | 46 | 46 | 46 | 46 |
| 14 | 46 | 45 | 46 | 46 |
| 15 | 46 | 46 | 46 | 46 |
| 16 | 46 | 46 | 46 | 45 |
| 17 | 46 | 46 | 46 | 46 |
| 18 | 46 | 46 | 46 | 46 |
| 19 | 46 | 46 | 46 | 46 |
| 20 | 46 | 46 | 46 | 46 |

FIG. 7C

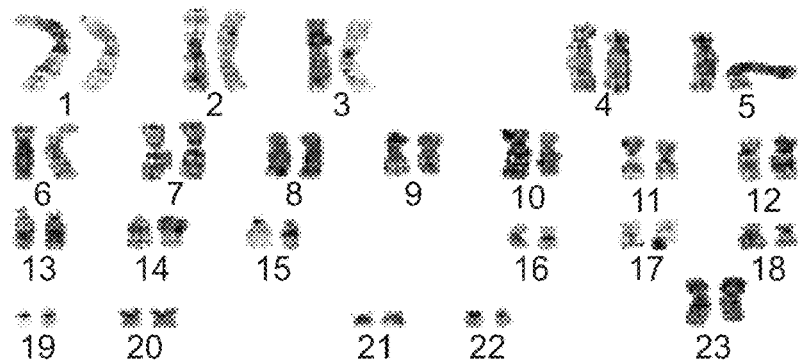
240LD1MY
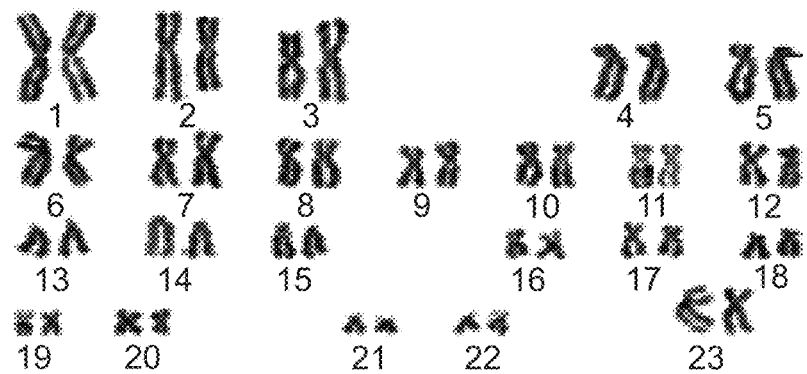
122LD1MY
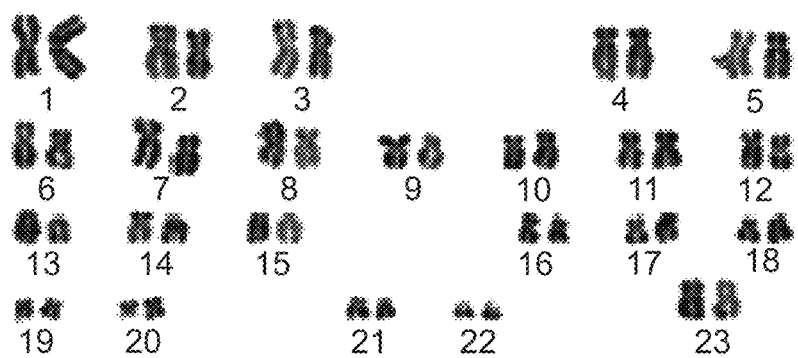
122L p16sMY
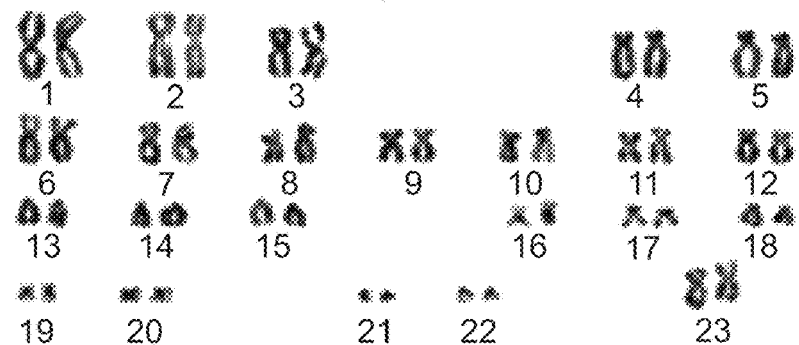
805Pp16sMY
FIG. 7C (Cont.)

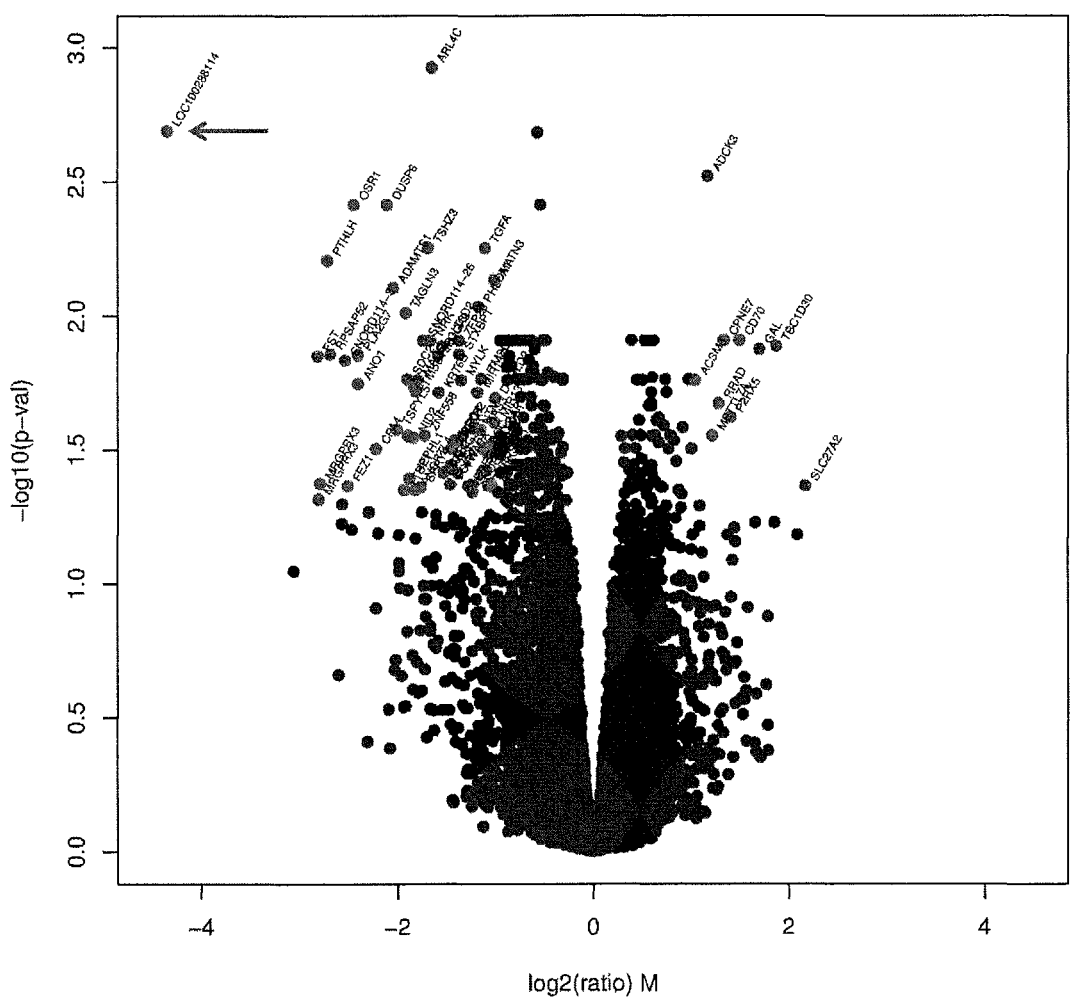

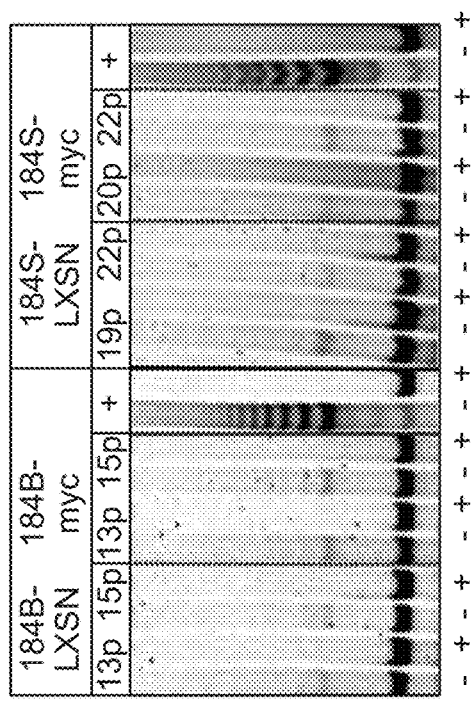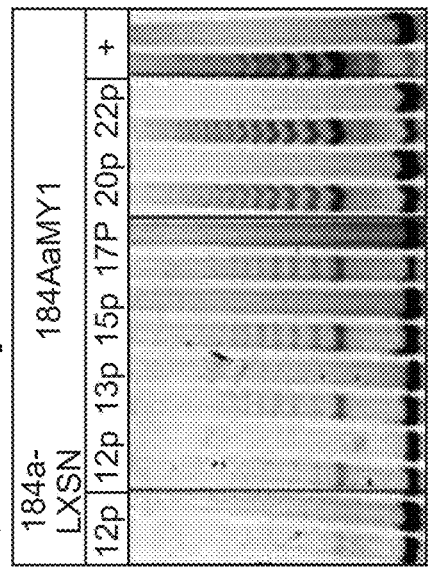
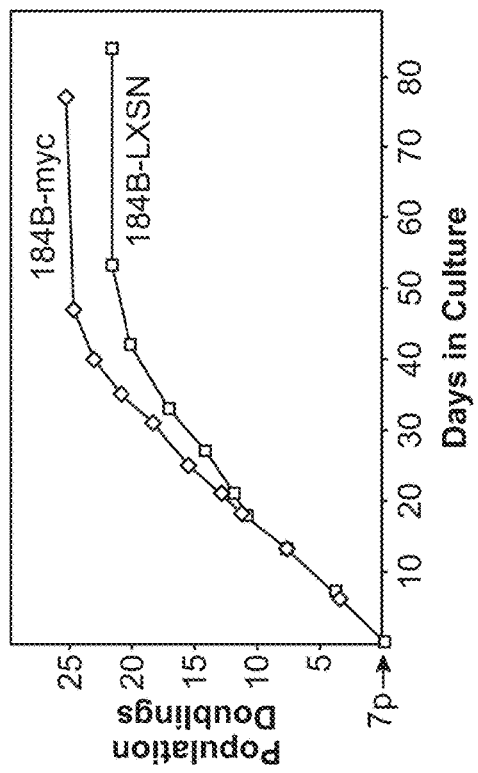
FIG. 10A
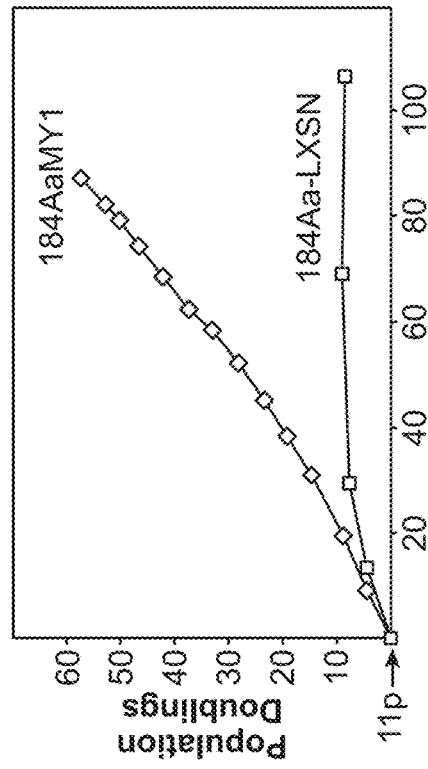
FIG. 10B

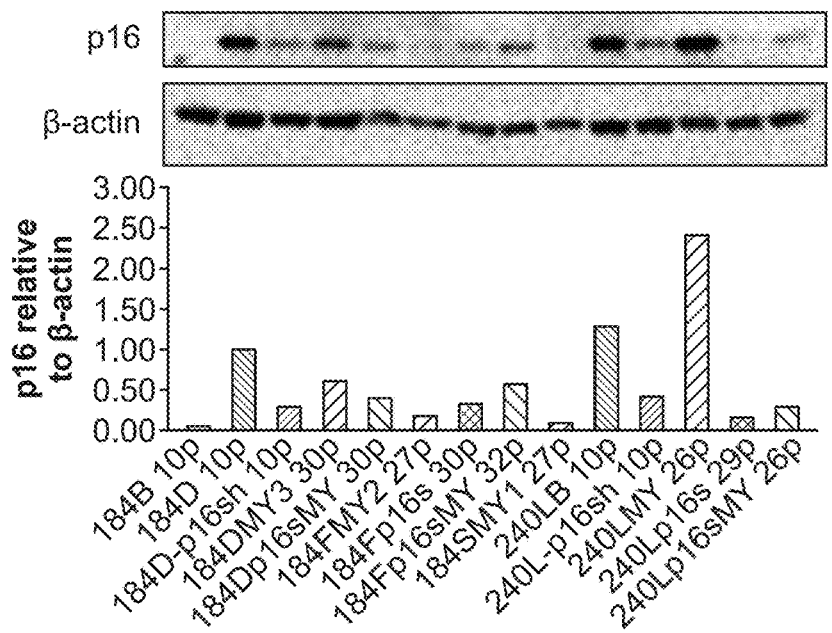
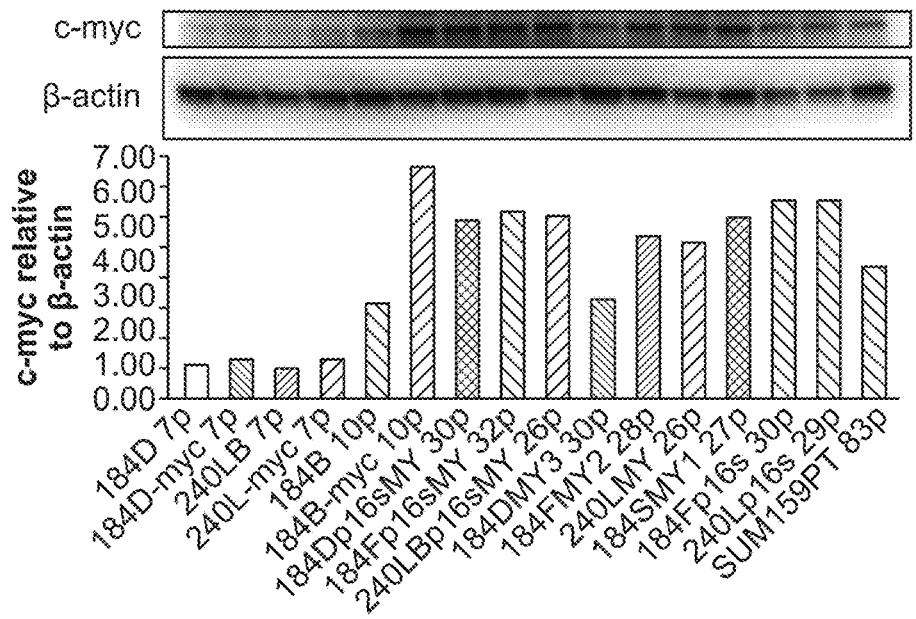
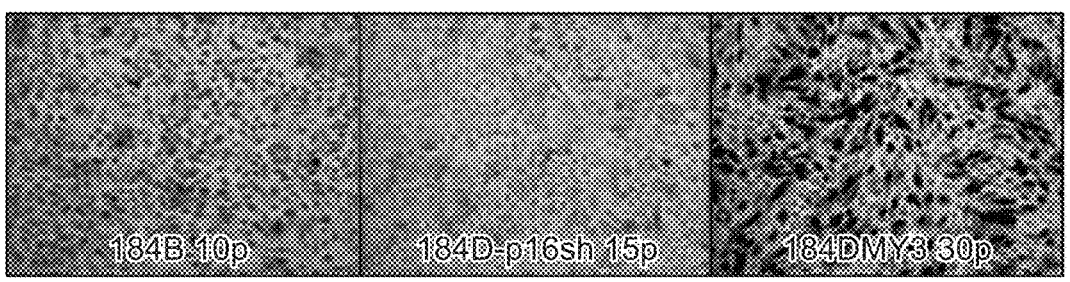
FIG. 11

FIG. 12A-D
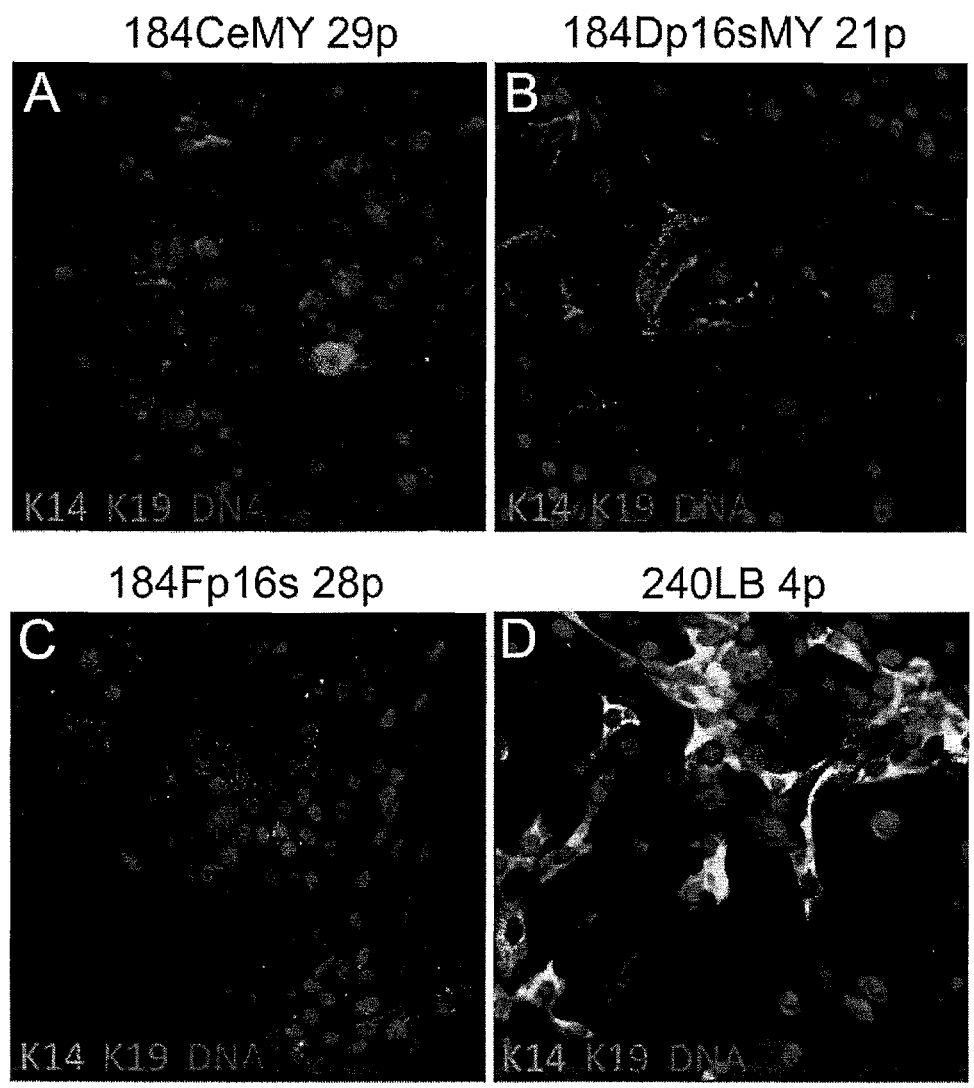

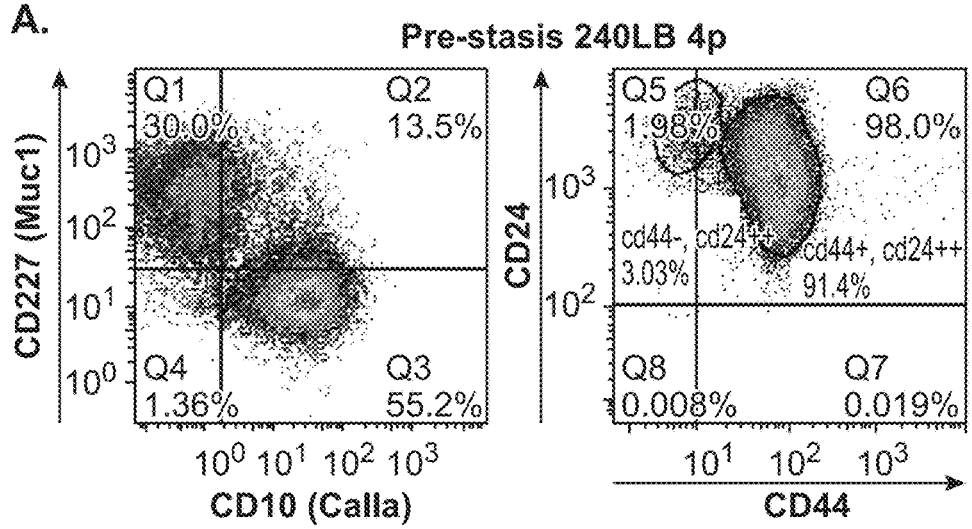
FIG. 14A
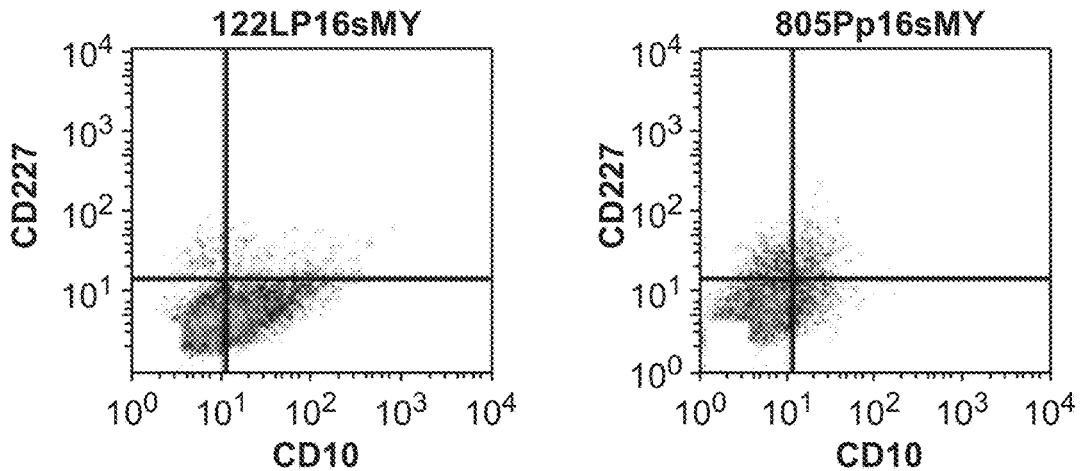
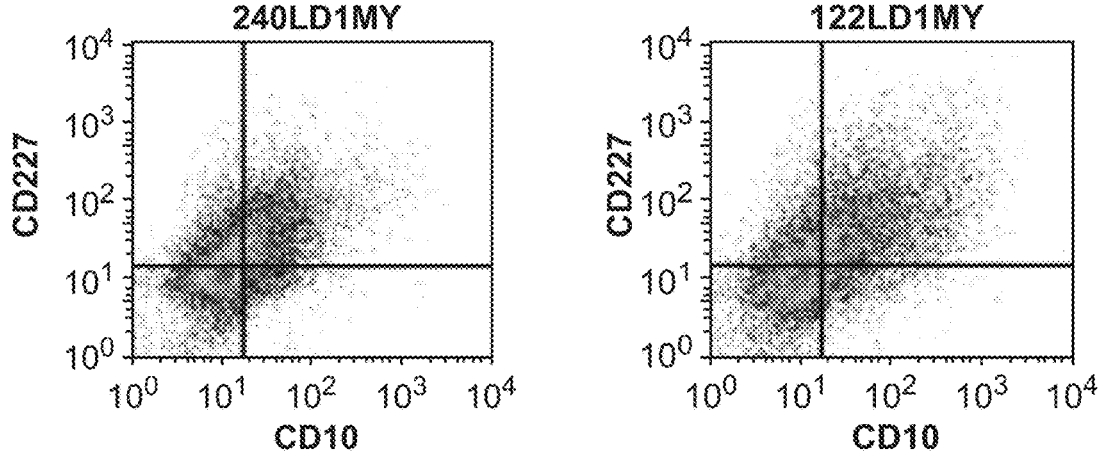
FIG. 14D

B. Clonal Lines

B. Pre-stasis 184F ± p16 shRNA and/or c-Myc

E. Pre-stasis 184D TRAP activity ± oxytocin

METHODS FOR IMMORTALIZATION OF EPITHELIAL CELLS

CROSS REFERENCE TO RELATED APPLICATIONS

This application claims priority to and is a continuation-in-part application of U.S. patent application Ser. No. 14/505,491, filed on Oct. 2, 2014, which is a non-provisional application of and claiming priority to U.S. Provisional Patent Application No. 61/886,021, filed on Oct. 2, 2013, both of which are hereby incorporated by reference in their entirety.

This application is also related to and claims priority to U.S. Provisional Patent Application No. 62/238,029, filed on Oct. 6, 2015, also hereby incorporated by reference in its entirety for all purposes.

STATEMENT OF GOVERNMENTAL SUPPORT

This invention was made with government support under Grant Nos. CA24844, AG033176, AG040081, CA23074 and CA65662 awarded by the National Institutes of Health, under Grant No. BCRP 060444 awarded by the Department of Defense, and under Contract No. DE-AC02-05CH11231 awarded by the U.S. Department of Energy. The government has certain rights in the invention.

BACKGROUND OF THE INVENTION

Field of the Invention

The present invention relates to methods for efficient immortalization of normal human epithelial cells and screening using these cells.

Related Art

The lack of knowledge about the process of human epithelial cell telomerase reactivation and immortalization has impeded efforts to target this process therapeutically. Although there has been work to understand telomerase activity in immortal cells, and to target the telomerase enzyme, there has been almost no effort to target the process of immortalization, to examine the regulation of telomerase in pre-malignant cells, or to determine how telomerase is reactivated during carcinoma progression. Part of the difficulty in doing this, in additional to the absence of small short-lived animal models that accurately model human cell immortalization, has been the absence of human cell culture models. Previous methods to immortalize human epithelial cells in vitro, that employed oncogenic agents that might reflect processes that occur during in vivo carcinogenesis, produced only rare clonal lines with genomic errors. This situation made it difficult to experimentally examine the immortalization process as it occurred. To get around this problem, many labs immortalized human cells by experimentally introducing and overexpressing into finite cells the gene for the telomerase enzyme, hTERT. Doing so precludes understanding what errors occur during carcinogenesis that are responsible for the reactivation of the endogenous telomerase gene. HMEC immortalized by hTERT show properties unlike either normal or abnormal HMEC in vivo. Another approach other labs have utilized to more immortalize human cells has been by employing the oncogenes present in oncogenic viruses like HPV16 or 18, or SV40. However, SV40 does not efficiently immortalize and is not an etiological agent for human cancers except under unusual (immunosuppressed) conditions and thus does not provide a model that reflects in vivo carcinogenesis. HPV is not an etiologic agent for breast cancer, though it has been implicated in cervical and oral cancer. However, it confers many distinct and undefined effects on cells, and its role in immortalization (e.g., whether or not it is the same process as occurs during in vivo immortalization during cervical carcinogenesis) is not definitively known.

Previously there was little effort to address this question of the mechanisms involved in reactivation of telomerase/immortalization as it occurs during in vivo carcinogenesis in humans, as there is currently no easy method to do so, and, as above, the importance of immortalization in human cancer progression has tended to be ignored since it is not a significant barrier for mice and rat "models". Some labs and companies are addressing ways to inhibit telomerase. A recent paper examines regulation of the hTERT gene integrated into a mouse genome during murine SV40T mediated carcinogenesis—a method that cannot accurately reflect all the specific mechanisms that regulate hTERT during human carcinogenesis. Our studies and hypotheses have further pointed out that telomere maintenance in cancer cells appears to be distinct from the (usually low level) telomere/telomerase regulation seen in normal telomerase expressing human stem and progenitor cells, i.e., cancer cells have short stable telomere lengths that may be regulated similar to telomerase regulation in the unicellular yeast organism. We are unaware of anyone else making this observation, other than in Sexton, A et al., "Genetic and molecular identification of three human TPP1 functions in telomerase action: recruitment, activation, and homeostasis set point regulation, *Genes Dev.* 2014 Sep. 1; 28(17):1885-99, hereby incorporated by reference.

We hypothesize that this difference in telomere regulation in cancer cells may require an active process as cells immortalize, including epigenetic changes; we further hypothesize that this is represented by the conversion process we see as part of HMEC in vitro immortalization. Such processes, which would be unique to cells becoming cancerous and not present in any other cell type in the body, could be a basis for the existence of unique (no collateral damage to normal cell mechanisms) therapeutically targetable mechanisms.

In short, this problem has been largely ignored, despite the essential and critical role of immortalization in human solid cancer progression. Indeed, many of the top scientists and journals refer to non-malignant immortally transformed human epithelial cells (i.e., cells that have acquired all the errors needed to overcome the main tumor suppressor barriers that normally prevent normal finite cells from transforming to immortality and thereby becoming vulnerable to malignant transformation) as "normal" or "untransformed", thereby ignoring the importance of all the errors that needed to occur to transform normal finite cells to immortality.

Therefore, what is needed is a method for efficient reproducible immortalization of HMEC that uses pathologically relevant agents and could be employed to examine the process of human epithelial cell immortalization as it might occur during in vivo carcinogenesis. Further, there is currently no method for inducing immortalization in the absence of pervasive "passenger" errors, using pathologically relevant agents. Such a method would permit easier examination of the underlying mechanisms of cancer progression and would enable the production of immortal lines lacking gross genomic errors as are present in the currently available immortal lines.

BRIEF SUMMARY OF THE INVENTION

Immortalization, associated with telomerase reactivation, is necessary for progression of most human carcinomas, and could therefore be a valuable therapeutic target. However, the paucity of experimentally tractable model systems that can examine human epithelial cell immortalization as it might occur during carcinogenesis has limited this potential. The prevalence of many genomic errors in primary human cancers makes it difficult to identify the driver errors responsible for immortalization using only in vivo tissues.

Herein is described an efficient reproducible method to immortalize cultured human epithelial cells by directly targeting the two main tumor-suppressive senescence barriers. The resultant lines exhibit normal karyotypes, indicating that genomic instability is not necessary per se for immortalization. This method of achieving non-clonal immortalization in the absence of "passenger" genomic errors should facilitate examination of this critical step in cancer progression, as well as exploration of agents that may prevent or reverse immortalization. That transduction of only shRNA to p16 and c-MYC can immortally transform normal human epithelial cells validates our model of the two main senescence barriers: (i) stasis, a stress-associated arrest independent of telomere length and extent of replication, and (ii) replicative senescence due to telomere dysfunction.

Thus in one embodiment, a method to efficiently and reproducibly immortalize normal human mammary epithelial cells (HMEC). This method, described in FIG. 5, is based upon our model of the HMEC tumor suppressive senescence barriers (FIGS. 1A and 1B).

In various embodiments, a method to immortalize normal human epithelial cells, the method comprising the steps of: a) providing normal pre-stasis epithelial cells in a low stress-inducing medium; b) introducing into normal pre-stasis epithelial cells a first polynucleotide construct that prevents the cell-cycle control protein retinoblastoma (RB) from staying in an active form, wherein such introduction occurs prior to the induction of cyclin-dependent kinase inhibitor 2A (p16$^{INK4a}$) and induces changes that bypass stasis; c) providing the epithelial cells that have bypassed stasis from the previous step, wherein the epithelial cells have bypassed stasis by bypassing the RB block; d) introducing into the post-stasis epithelial cells a polynucleotide construct that will induce expression of human telomerase reverse transcriptase (hTERT) and/or telomerase activity, wherein such introduction of the polynucleotide construct occurs prior to telomere dysfunction from eroded telomeres, and whereby said introduction induces changes that reactivate sufficient telomerase activity; and e) reactivating telomerase activity thereby inducing immortalization of said post-stasis epithelial cells.

Herein is described methods and constructs for direct targeting of the two main tumor-suppressive senescence barriers, using agents implicated in in vivo carcinogenesis, that enables examination of HMEC immortalization as it occurs. It is shown that early passages of immortalized cells that bypassed the senescence barriers through direct targeting possess a normal karyotype. This result highlights the importance of telomere dysfunction-induced genomic instability prior to immortalization in the generation of cancer-associated genomic errors (driver and passenger).

Thus, a method to efficiently and reproducibly immortalize normal human mammary epithelial cells (HMEC), the method comprising the steps of: a) providing HMEC in a low stress-inducing medium; b) introducing into pre-stasis HMEC a first polynucleotide construct that prevents the cell-cycle control protein retinoblastoma (RB) from staying in an active form, wherein such introduction occurs prior to the induction of cyclin-dependent kinase inhibitor 2A (p16) and induces changes that bypass the RB block and stasis; c) providing HMEC that have bypassed stasis from the previous step, wherein the HMEC have bypassed stasis by bypassing the RB block; d) introducing into the post-stasis HMEC a polynucleotide construct that will induce expression of human telomerase reverse transcriptase (hTERT) and/or telomerase activity, wherein such introduction of the polynucleotide construct occurs prior to telomere dysfunction from eroded telomeres, and whereby said introduction induces changes that reactivate sufficient telomerase activity; and e) reactivating telomerase activity thereby inducing immortalization of said post-stasis HMEC.

The low-stress inducing medium can be M87A or a medium that does not produce a rapid rise of the stress-induced molecule cyclin-dependent kinase inhibitor 2A (p16$^{INK4a}$) in the HMEC.

The first polynucleotide construct for transduction of pre-stasis HMEC can be a p16 shRNA, a cyclin D1/cyclin dependent kinase 2 (CDK2) fusion protein, a mutant cyclin-dependent kinase 4 (CDK4) protein, or an inhibitory molecule to inactivate RB function. In some embodiments, the first polynucleotide construct is a p16 shRNA.

The method may further comprise a step of introducing into pre-stasis HMEC a second polynucleotide construct that targets either direct loss of RB function or inactivation of p53.

The second polynucleotide construct can be an inhibitory molecule to inactivate RB function to target direct loss of RB function or p53 shRNA or GSE p53 inhibitor to inactivate p53.

Herein we describe support for the model of the senescence barriers encountered by cultured HMEC, by illustrating the functional distinctions between stasis (a stress-associated arrest independent of both telomere length and extent of replication), and replicative senescence due to telomere dysfunction. At the basic level, it is shown that genomic instability is not required per se for immortalization, but is needed to generate the errors that bypass/overcome senescence barriers.

At a practical level, the presently described method of generating immortalized lines that lack "passenger" errors should greatly facilitate examination of the mechanisms underlying this crucial, but still poorly understood step in human carcinogenesis.

At a potential translational level, the process of immortalization could be a valuable therapeutic target for multiple cancer types. The absence of good model systems of human epithelial cell cancer-associated immortalization has hampered examination of ways to prevent or reverse this process.

Using the non-clonal immortalized cells produced by the methods described herein, further methods of screening are provided. A method for screening the effect of toxin on cancer progression comprising the steps of: a) providing human cells in a low stress-inducing medium; b) introducing a toxin to said pre-stasis cells, wherein such introduction occurs prior to the induction of cyclin-dependent kinase inhibitor 2A (p16) and induces errors that bypass stasis; c) providing cells that have bypassed stasis from the previous step, wherein the cells have bypassed stasis by bypassing the RB block; d) screening said post-stasis cells for differential expression profiles from the normal cells and/or sequencing said post-stasis cells to identify the changes induced by toxin-induced stasis bypass.

A method for screening the effect of an agent on cancer progression comprising the steps of: a) providing cells in a low stress-inducing medium; b) introducing into pre-stasis cells a first agent that prevents the cell-cycle control protein Retinoblastoma (RB) from staying in an active form, wherein such introduction occurs prior to the induction of cyclin-dependent kinase inhibitor 2A (p16) and induces errors that bypass stasis; c) providing cells that have bypassed stasis from the previous step, wherein the cells have bypassed stasis by bypassing the RB block; d) introducing to the post-stasis cells a second agent to determine if the second agent induces expression of human telomerase reverse transcriptase (hTERT) and/or telomerase activity, wherein such introduction of the agent occurs prior to telomere dysfunction from eroded telomeres; and e) screening for induction of errors that reactivate telomerase activity and thereby inducing immortalization of said post-stasis cells.

In some embodiments, such methods can be carried out using cells progressing to immortalization from any human cell type. In various embodiments, the cells are epithelial cells. In some embodiments, the cells are breast or mammary cells.

In certain aspects, the present disclosure provides methods to immortalize epithelial cells. The methods include culturing pre-stasis epithelial cells in a low stress-inducing medium, and prior to induction of cyclin-dependent kinase inhibitor 2A (p16) in the pre-stasis epithelial cells, introducing into the pre-stasis epithelial cells a polynucleotide that prevents the retinoblastoma protein (RB) from staying in an active form, to produce post-stasis epithelial cells. Such methods further include, prior to telomere dysfunction in the post-stasis epithelial cells, introducing into the post-stasis epithelial cells a polynucleotide that induces telomerase activity, to immortalize the epithelial cells. According to certain embodiments, the low stress-inducing medium is M87A medium. In certain aspects, the polynucleotide that prevents RB from staying in an active form is selected from a p16 shRNA, a polynucleotide that encodes a cyclin D1/cyclin dependent kinase 2 (CDK2) fusion protein, a polynucleotide that encodes a mutant cyclin-dependent kinase 4 (CDK4) protein, and an RB shRNA. According to certain embodiments, the polynucleotide that prevents RB from staying in an active form is a p16 shRNA. In certain aspects, the polynucleotide that prevents RB from staying in an active form does not directly target Rb expression, and the method further includes introducing an additional polynucleotide into the pre-stasis epithelial cells that targets RB expression or inactivates p53. The additional polynucleotide may include, e.g., an RB shRNA, a p53 shRNA, a p53 genetic suppressor element, and/or the like. In certain aspects, the pre-stasis epithelial cells are pre-stasis mammary epithelial cells. According to some embodiments, the pre-stasis epithelial cells are pre-stasis mammary epithelial cells, e.g., pre-stasis human mammary epithelial cells (HMEC). In certain aspects, the polynucleotide that induces telomerase activity induces expression of hTERT. According to some embodiments, the polynucleotide that induces telomerase activity encodes c-MYC. In certain aspects, the polynucleotide that prevents RB from staying in an active form is a p16 shRNA and the polynucleotide that induces telomerase activity encodes c-MYC. For example, the polynucleotide that prevents RB from staying in an active form may be a p16 shRNA, the polynucleotide that induces telomerase activity may encode c-MYC, the low stress-inducing medium may be M87A medium, and/or the pre-stasis epithelial cells may be pre-stasis human mammary epithelial cells (HMEC). The methods may include analyzing, e.g., by gene expression profiling, sequencing, and/or the like, immortalized cells produced according to any of the above methods. Also provided are immortalized cells produced according to any of the above methods.

According to some embodiments, the present disclosure provides methods of identifying an agent that prevents cell immortalization. Such methods include culturing pre-stasis epithelial cells in a low stress-inducing medium, and prior to induction of cyclin-dependent kinase inhibitor 2A (p16) in the pre-stasis epithelial cells, introducing into the pre-stasis epithelial cells a polynucleotide that prevents the retinoblastoma protein (RB) from staying in an active form, to produce post-stasis epithelial cells. Such methods further include, prior to telomere dysfunction in the post-stasis epithelial cells, introducing into the post-stasis epithelial cells an agent and a polynucleotide that induces telomerase activity. Such methods further include, subsequent to introducing the agent and the polynucleotide that induces telomerase activity, culturing the epithelial cells to determine whether the cells are immortalized. When the cells are not immortalized, the agent is identified as an agent that prevents cell immortalization. In certain aspects, the agent is a polynucleotide or a small molecule. According to certain embodiments, the RB-inactivating polynucleotide is a p16 shRNA, the polynucleotide that induces telomerase activity encodes c-MYC, or both. In certain aspects, the low stress-inducing medium is M87A medium. According to certain embodiments, the pre-stasis epithelial cells are pre-stasis human mammary epithelial cells (HMEC), e.g., normal or abnormal HMEC.

Also provided by the present disclosure are methods of identifying an agent that reverses cell immortalization. Such methods include culturing pre-stasis epithelial cells in a low stress-inducing medium, and prior to induction of cyclin-dependent kinase inhibitor 2A (p16) in the pre-stasis epithelial cells, introducing into the pre-stasis epithelial cells a polynucleotide that prevents the retinoblastoma protein (RB) from staying in an active form, to produce post-stasis epithelial cells. Such methods further include, prior to telomere dysfunction in the post-stasis epithelial cells, introducing into the post-stasis epithelial cells a polynucleotide that induces telomerase activity to produce immortalized cells. Such methods further include introducing an agent into the immortalized cells, and subsequent to introducing the agent into the immortalized cells, culturing the epithelial cells to determine whether the cells remain immortalized. When the cells do not remain immortalized, the agent is identified as an agent that reverses cell immortalization. In certain aspects, the agent is a polynucleotide or a small molecule. According to certain embodiments, the RB-inactivating polynucleotide is a p16 shRNA, the polynucleotide that induces telomerase activity encodes c-MYC, or both. In certain aspects, the low stress-inducing medium is M87A medium. According to certain embodiments, the pre-stasis epithelial cells are pre-stasis human mammary epithelial cells (HMEC), e.g., normal or abnormal HMEC.

The present disclosure further provides methods of identifying an agent that immortalizes post-stasis epithelial cells. Such methods include culturing pre-stasis epithelial cells in a low stress-inducing medium, and prior to induction of cyclin-dependent kinase inhibitor 2A (p16) in the pre-stasis epithelial cells, introducing into the pre-stasis epithelial cells a polynucleotide that prevents the retinoblastoma protein (RB) from staying in an active form, to produce post-stasis epithelial cells. Such methods further include, prior to telomere dysfunction in the post-stasis epithelial cells, introducing an agent into the post-stasis epithelial cells. Such methods further include, subsequent to introducing the agent, culturing the epithelial cells to determine whether the cells are immortalized as a result of introduction of the agent. When the cells are immortalized, the agent is identified as an agent that immortalizes non-clonal post-stasis epithelial cells. Also provided are immortalized cells produced according to any of the above methods. The methods may include analyzing, e.g., by gene expression profiling, sequencing, and/or the like, immortalized cells produced according to any of the above methods. The agent may be a polynucleotide or a small molecule. In certain aspects, the agent is a toxin. According to certain embodiments, the RB-inactivating polynucleotide is a p16 shRNA, the polynucleotide that induces telomerase activity encodes c-MYC, or both. In certain aspects, the low stress-inducing medium is M87A medium. According to certain embodiments, the pre-stasis epithelial cells are pre-stasis human mammary epithelial cells (HMEC), e.g., normal or abnormal HMEC.

Also provided by the present disclosure are methods for identifying an agent that causes pre-stasis epithelial cells to bypass stasis. Such methods include culturing pre-stasis epithelial cells in a low stress-inducing medium, introducing an agent into the pre-stasis epithelial cells, and subsequent to introducing the agent, determining whether the epithelial cells have bypassed stasis as a result of introduction of the agent. According to certain embodiments, determining whether the epithelial cells have bypassed stasis includes introducing into the epithelial cells an agent that immortalizes post-stasis epithelial cells, and determining whether the epithelial cells are immortalized, where when the epithelial cells are immortalized, the agent introduced into the pre-stasis epithelial cells is identified as an agent that causes pre-stasis epithelial cells to bypass stasis. According to certain embodiments, determining whether the epithelial cells have bypassed stasis includes introducing into the epithelial cells an agent that induces p16 in pre-stasis cells, and determining whether p16 is induced in the epithelial cells, where when p16 is not induced as a result of introduction of the agent that induces p16 in pre-stasis cells, the agent introduced into the pre-stasis epithelial cells is identified as an agent that causes pre-stasis epithelial cells to bypass stasis. According to certain embodiments, the low stress-inducing medium is M87A medium. In certain aspects, the agent is a polynucleotide or a small molecule. According to certain embodiments, the agent is a toxin. In certain aspects, the agent that immortalizes post-stasis epithelial cells encodes c-MYC.

BRIEF DESCRIPTION OF THE DRAWINGS

FIG. 3, Panel A: Newly immortalized p53(+) HMEC (shown here the 184A1 line) have the capacity to express telomerase activity (measured by the TRAP assay), but show low expression until mean TRF levels become very short (~3 kb); telomere lengths continue to shorten and growth capacity (CFE) declines. After mean TRF declines to ~3 kb, the conversion process is engaged; telomerase activity and growth capacity gradually increase, and mean TRF stabilizes at ~3-7 kb. FIG. 3, Panel B: If p53 is inactivated (B; using the p53 inhibitor GSE22) then TRAP activity rapidly increases and telomere lengths stabilize, indicating that the ability to express telomerase activity was already present, but repressed by p53. Resistance to OIS is associated with the gain of telomerase activity. We have postulated that the conversion process may involve epigenetic changes. [Stampfer et al. MCB 1997, Oncogene 2003, Springer 2013]

FIG. 6A-6D: Examples of efficient immortalization using shRNA to p16 or D1/cdk2 to bypass stasis, and c-MYC to immortalize post-stasis HMEC from 4 different individuals. HMEC from specimens 184, 21 yrs (FIG. 6A) and 240L 19 yrs (FIG. 6B) produced non-clonal immortal lines after exposure to p16 shRNA at passage (p) 3, followed by c-MYC at 4p. Rare clonal lines were generated by p16 shRNA or c-MYC alone. TRAP activity increases at the point of immortalization. HMEC from specimen 805P, 91 yrs (FIG. 6C) and 122L, 66 yrs (FIG. 6D) were also non-clonally immortalized by p16 shRNA or D1/cdk2 followed by c-MYC, with rare clonal lines generated by p16 shRNA or c-MYC alone.

FIGS. 7A and 7B: Non-clonal lines have a normal karyotype at early passage, whereas clonal lines contain many genomic errors. FIG. 7A. Representative karyograms of newly derived immortalized lines at early passages; non-clonal 184Dp16sMY (46,XX) is show as an example of a normal karyotype. 184Dp16sMY: 46,XX; 184AaMY1: 47,XX,+i(1)(q10); and 184BeMY: 46,X,add(X)(q28), −4,der(5)t(5; 15)(q11.2; q11.2), der(12)t(5; 12)(q11.2; q24.3), −15,+2mar. Individual abnormalities are shown by arrows. The non-clonal line derived from normal pre-stasis 184 exposed to p16 shRNA followed by c-MYC (184Dp16sMY) shows a normal karyotype at passage 16. Lines derived from pre-stasis 184 first exposed to BaP to become clonally post-stasis, and then exposed to c-MYC for non-clonal immortalization (184AaMY, 184BeMY), contain some errors, presumably due to the entry into telomere dysfunction prior to c-MYC exposure. FIG. 7B. aCGH analysis of clonal and non-clonal lines shows that the clonal lines contain many genomic errors, whereas the non-clonal lines (184Dp16sMY and 240Lp16sMY) at higher passage show 1-2 errors: a small deletion in the p16 region that would not be apparent by karyology, and an amplification of 1 q in a subpopulation of 240Lp16sMY. 184CeMY, which was non-clonally immortalized from a BaP post-stasis clone prior to telomere dysfunction has a normal karyotype at 12p and shows no aCGH changes at 25p.

FIG. 7C shows biochemical and karyologic characterization of non-clonal non-malignant immortal HMEC cell lines. The left panel shows a table of karyotypes of 20 cells each of the indicated cell lines. The right panel shows representative examples of karyotypes from the indicated cell lines.

FIG. 8: Significant gene expression changes linked to non-clonal immortalization of the four individuals shown in FIG. 1B pre-stasis HMEC using p16sh or transduced D1/cdk2 to become post-stasis, and c-MYC transduction for immortalization. Gene expression was analyzed using Affytmetrix ST microarrays, and a plot of gene expression differences that compares the 6 non-clonal immortal cell lines to the finite parent cell strains is shown. The x-axis shows the log 2-fold change in gene expression and the y-axis shows the multiple testing corrected p-values. All the genes are represented by dots on the plot. The blue dots represent genes that do not show significant changes in gene expression, while the red dots represent genes that displayed significant decreases or increases in gene expression in the immortal cells when compared to the finite parent strains. The arrow points to a differentially expressed lncRNA (Mort).

FIG. 9A, Aberrant DNA methylation of the HOXD gene cluster during the conversion step of HMEC immortalization. DNA methylation was determined in seven HMEC cultures using MeDIP coupled microarray analysis. These specimens range from finite (pre-stasis 184D, post-selection post-stasis 184B and BaP post-stasis 184Aa) to immortal undergoing the conversion process (184A1 p14 immortal pre-conversion, 184A1 p21 in conversion, 184A1 p49 fully converted); 184A1-TERT is a control for an immortal line expressing telomerase that did not undergo conversion (because hTERT was transduced pre-conversion at p12). The level of DNA along ~125 kb of the HOXD genomic interval is shown. The heat map shows the lowest level DNA methylation in yellow to the highest level of DNA methylation in blue. Shown below the heat maps are the CpG islands (green) and the genomic position along chromosome 2. FIG. 9B. Aberrant DNA Methylation during conversion can recapitulate events that occur at other proliferation barriers. Epigenetic changes associated with the transition from pre-stasis to post-selection post-stasis (184B) are also seen during the conversion process in HMEC that immortalized (184A1) from BaP post-stasis cultures (184Aa) that did not acquire these changes when they became post-stasis. DNA methylation was determined as above in the same samples. The levels of DNA methylation in miR183/96/182, WNT5A, and p16 are shown. The heat map shows the lowest level DNA methylation in yellow to the highest level of DNA methylation in blue. Shown below the heat maps are the CpG islands (green) and the genomic position along the respective chromosomes.

FIGS. 10A and 10B: Effect of c-MYC on post-stasis HMEC growth and TRAP activity. FIG. 10A: Post-stasis post-selection 184B HMEC grown in MCDB170 were transduced with a c-MYC containing retrovirus (LXSN, red) or empty vector control at 7p (blue). Cultures ceased net growth at agonescence (15p). Post-selection 184S HMEC were transduced with c-MYC or control at 15p; net growth ceased at 22p (not shown). No significantly increased TRAP activity was seen following c-MYC transduction in either experiment. FIG. 10B: BaP post-stasis 184Aa, 184Be, and 184Ce HMEC grown in MCDB170 were transduced with a c-MYC containing retrovirus (LXSN/BH2), red) or empty vector (blue) at the indicated passages. Control cells ceased net growth at agonescence while c-MYC-transduced populations maintained proliferation indefinitely, associated with increased TRAP activity. The continuous exponential growth following c-MYC transduction reflects the visually observed non-clonal immortalization; growth was maintained throughout the dish with no areas of clonal growth. Proliferating control cultures of 184Ce expressed low TRAP activity.

FIG. 11, Panels A-C, show expression of p16 (CDNK2A) and c-MYC protein in HMEC cultures. Panel A: Western analysis of p16 expression. Cells transduced with p16sh exhibit reduced p16 levels, while variable levels were seen in MYC-alone transduced clonal lines. Post-selection 184B and the line derived from post-selection 184 (184SMY1) express little or no p16. Transduction of 184Dp16sMY at 20p with a p16-containing construct (pLenti-p16-neo) resulted in complete growth arrest within 11 days, indicating that this p16sh-tranduced line was still responsive to p16 inhibition (data not shown). Pre-stasis HMEC are shown in green, post-stasis in blue, and immortalized lines in red. Panel B: Western analysis of c-MYC expression. Immortalized lines, including lines derived without use of transduced c-MYC, exhibit variable increased c-MYC expression levels. Normal pre-stasis HMEC transduced with c-MYC did not show significant increased c-MYC, but expression was increased in transduced abnormal post-selection 184B, which did not immortalize Similar results were seen by ELISA assay (not shown). Pre-stasis HMEC are shown in green, post-stasis in blue, and immortalized lines in red. Panel C: Immunohistochemistry of p16 expression. Transduction of p16sh into 3p pre-stasis 184D led to the absence of detectable p16 protein expression in p16sh post-stasis 184D at 15p, when cell proliferation was stopped by agonescence. No protein is seen in post-selection 184B, whereas a population mixed for p16 expression is seen in immortalized 184DMY3.

FIG. 12A-12D: Immunofluorescent images of representative HMEC lines stained for the myoepithelial lineage marker keratin 14 and the luminal marker keratin 19. (Panels A-C) Lines show expression of keratin 14 and little or no expression of keratin 19, confirming the basal phenotype. (Panel D) Normal pre-stasis 240L HMEC at 4p are shown as a positive control for keratin 19.

FIG. 13A shows the tiling microarray data from the TERT promoter region displayed as a heatmap, with blue indicating high enrichment of particular epigenetic mark and yellow indicating no enrichment. This region includes the areas bound by H3K4me3 and transcription factors including c-MYC according to online data (Genome website and browser at ucsc.edu). Upper and middle sections of the heatmap show permissive H3K4me3 and repressive H3K27me3 histone marks, respectively; the bottom section shows DNA methylation data. Two regions (UP and TSS) indicated by brown bars at the bottom were analyzed for DNA methylation at higher resolution by MassARRAY analysis. The small black rectangles above the heatmap indicate positions of individual microarray probes. The vertical bars below the heatmap indicate positions of individual CpG dinucleotides. The CpG island is marked in green. The 5' part of the hTERT gene is in blue. The genomic coordinates at the top are hg18. FIG. 13B and FIG. 13C show MassARRAY analysis data for regions UP and TSS indicated in FIG. 13A. The data are presented as a heatmap with methylated CpG units in blue and unmethylated CpG units in yellow.

FIG. 14A-14D. FACS characterization of HMEC lines for CD10/CD227 and CD44/CD24. FIG. 14A: pre-stasis HMEC; FIG. 14B: clonal lines; FIG. 14C and FIG. 14D: non-clonally immortalized lines. Expression of CD227 and CD10, and CD44 and CD24$^{hi}$ in 14A of 4p normal pre-stasis finite strain 240L, shows two clear populations CD10−/CD227+, CD44$^{hi}$/CD24$^{low}$ luminal and CD10+/CD227−, CD44$^{hi}$/CD24$^{hi}$ myoepithelial cells. The new immortal lines from young individuals are predominantly CD44$^{hi}$/CD24$^{hi}$, but significant CD44$^{hi}$/CD24$^{low}$ subpopulations were often present; the relationship between these populations is not known. FIG. 14D, Panel (1): Immortal non-clonal non-malignant HMEC lines from two older women that used p16shRNA to bypass stasis. FIG. 14D, Panel (2): Both immortal non-clonal non-malignant HMEC lines that used cyclinD1/CDK2 to bypass stasis. Quadrant lines are indicated for frame of reference. FIG. 14B: Immortal clonal non-malignant HMEC lines from two younger women. FIG. 14C: Immortal non-clonal non-malignant HMEC lines from two younger women.

(FIG. 15A) Post-selection post-stasis 48RS HMEC grown in MCDB170 were transduced with a c-MYC containing retrovirus (LNCX2-MYC-ires-GFP (red) or empty vector control (blue) at 7p. All cells ceased net proliferation at agonescence. (FIG. 15B) Pre-stasis 184F was grown in M85+CT from 2p and transduced at 4p with a p16shRNA expressing retrovirus (MSCV) (blue) or empty vector (black). At 5p cultures ±p16sh were transduced with c-MYC or vector control (LXSN) (red+ p16sh; purple −p16sh). c-MYC-transduced p16sh post-stasis HMEC maintained active growth indefinitely (184Fp16sMY). Cells transduced with p16sh alone bypassed stasis and ceased growth at agonescence, with a clonal immortalization at agonescence from one population (184Fp16s). Cells transduced with c-MYC alone ceased growth at stasis, with a clonal escape from stasis leading to immortalized 184FMY2. Control cultures transduced with empty vectors ceased growth at stasis. TRAP activity assayed at 8p indicated high activity for 184Fp16sMY and increased activity in 184FMY2. (FIG. 15C) Pre-stasis 184D grown in M87A+CT+X were transduced at 3p with an hTERT expressing retrovirus (pBabe-hygro-TERT) (red) or vector alone (black). Both populations maintained equivalent good growth up to stasis at 11p; control cultures stopped growth at stasis whereas hTERT-transduced cultures maintained growth indefinitely, generating the 184DTERT line. (FIG. 15D) Post-stasis 240L-p16sh grown in M87A+CT+X were transduced at 7p with an hTERT expressing retrovirus (pBabe)(red) or vector alone (blue). Control cultures ceased net growth at agonescence at 13p whereas hTERT-transduced cultures maintained growth indefinitely, generating the 240Lp16sTERT line. (FIG. 15E) TRAP activity in pre-stasis 184D. Cells were grown in M85+CT±X with stasis at 15p (+X) or 10p (−X). Proliferative populations express low activity that is decreased by stasis. TRAP activity in post-selection post-stasis 184B and immortal 184A1 is shown for comparison.

FIG. 16A shows aCGH analysis of newly developed lines from 184F. FIG. 16B shows detail of aCGH analysis of chromosome 9 p21.3 region showing the small deletion including p16 gene. The log 2 signal ratios from individual microarray probes are plotted at genomic coordinates (hg18) they measure. The colored dotted lines indicate 1.5-fold difference in microarray signal. The data show the loss of one copy of p16/p15 genes locus in the lines 184Dp16sMY at 30p and 240Lp16sMY at 25p, and both copies of mir-31/MTAP locus in 240Lp16sMY. The region is intact in the 240Lp16s line at 25p shown at the top.

Figure 1A:
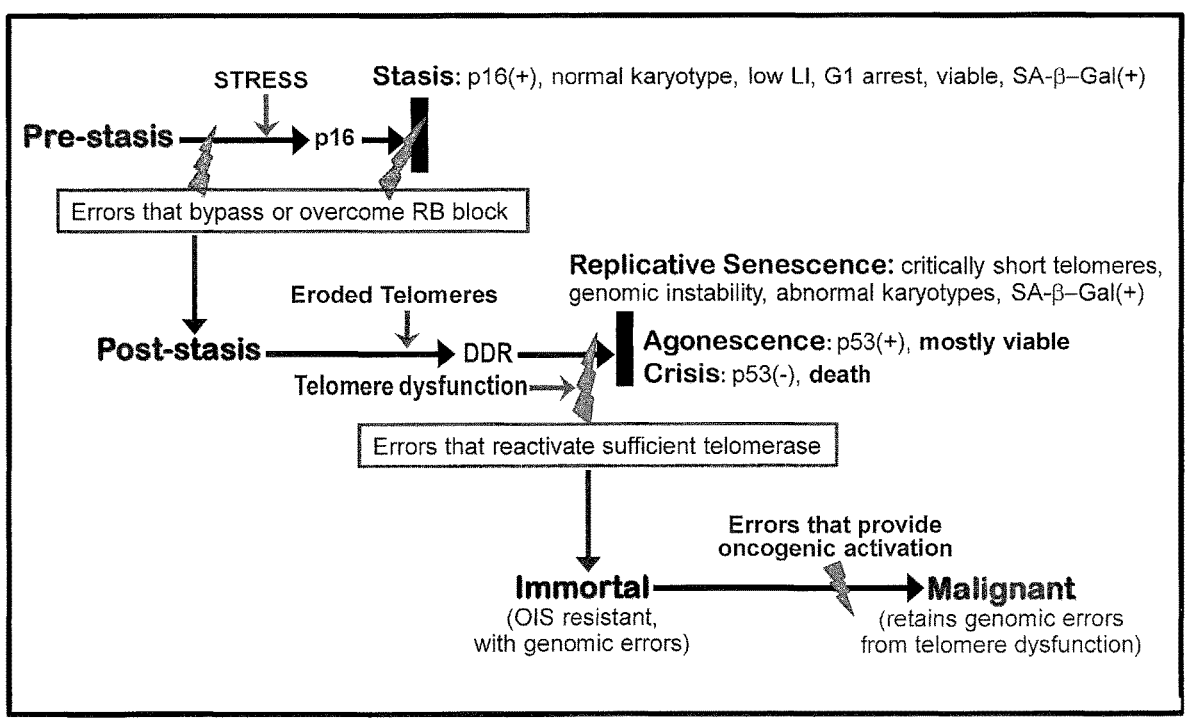
FIG. 1A: HMEC model system. Schematic model of senescence barriers encountered by cultured HMEC. Thick black bars represent the proliferation barriers of stasis and replicative senescence. Orange bolts represent genomic and/or epigenomic errors allowing these barriers to be bypassed or overcome. Red arrows indicate crucial changes occurring prior to a barrier. Normal cells obtained from reduction mammoplasty tissues and cultured in low stress-inducing medium such as M87A stop growth at stasis due to elevation of p16 expression. If exposed to oncogenic agents (such as chemical carcinogens, c-MYC, heavy metals, stress) they may incur genomic and/or epigenomic errors that allow them to bypass or overcome stasis. Continued replication of post-stasis HMEC in the absence of sufficient telomerase leads to shortening telomeres. When telomeres become critically short, telomere associations may occur, leading to genomic instability and genomic errors. In the vast majority of situations, these errors lead to cessation of cell growth (when p53+) or death (when p53−). If errors occur that allow reactivation of telomerase activity, the cell may immortalize, carrying with it all the genomic errors it incurred up to that point. Expression of sufficient telomerase in cultured HMEC has been correlated with gaining resistance to OIS. While finite HMEC exposed to many oncogenes will stop growth, immortalized cells exposed to the same oncogenes will not only maintain growth but also acquire malignancy-associated properties.

Table 2 MassARRAY primers sequences used for the Sequenom MassARRAY analysis of the TERT promoter. The SEQ ID NO: is also provided.

TABLE 2

| SEQ ID NO: | TERT promoter MassARRAY | SEQUENCE |
|---|---|---|
| 1 | TERT_UP_10F | aggaagagagGGTATTTTGTTTGGTAGATGAGGTT |
| 2 | TERT_UP_T7R | cagtaatacgactcactatagggagaaggctCCCTAATAACAAAAACAATTCACAAA |
| 3 | TERT_TSS_10F | aggaagagagAGGGTTTTTATATTATGGTTTTTTT |
| 4 | TERT_TSS_T7R | cagtaatacgactcactatagggagaaggctACACCAAACACTAAACCACCAAC |

DETAILED DESCRIPTION

Introduction and Model

Acquisition of sufficient telomerase activity to maintain stable telomere lengths is necessary for immortalization of most human epithelial cells. In turn, immortalization appears essential for development and progression of malignant human carcinomas. While normal finite human epithelial cells contain an intact genome, immortal, telomerase-expressing carcinoma cells usually exhibit many genomic errors and genomic instability. During in vivo carcinoma progression, short telomeres and widespread genomic instability can first be observed in many pre-malignant lesions, such as DCIS in breast [4,5]. We have postulated that the genomic instability caused by the critically shortened telomeres present in finite lifespan cells as they approach replicative senescence may give rise to rare errors permissive for telomerase reactivation, and underlie many of the passenger errors seen in carcinomas [1, 10].

Despite the crucial role of telomerase and immortalization in human carcinogenesis, the mechanisms that control telomerase expression, and the aberrations that allow telomerase reactivation during malignant progression, are still poorly understood. It is difficult to determine which errors are responsible for driving cancer-associated immortalization using in vivo human tissues, given the background of many passenger errors. The lack of appropriate experimentally tractable model systems of human cancer-associated telomerase reactivation and immortalization has also contributed to this knowledge gap. In addition, murine cells are known to have significant differences from human in their regulation of telomerase, including less stringent telomerase repression than exists in adult human somatic cells [2,3]. Thus, telomerase activity is not limiting in most murine carcinoma model systems. Moreover, there is a paucity of human epithelial cell immortalization models suitable for experimental examination of telomerase reactivation during carcinogenesis. Immortalization models employing transduction of ectopic hTERT, the catalytic subunit of telomerase, preclude identifying the errors responsible for telomerase reactivation during in vivo human carcinogenesis.

Immortalization, associated with reactivation of telomerase activity, is an essential but poorly understood step in human epithelial cell carcinogenesis, due in part to the paucity of experimentally tractable model systems that can examine human epithelial cell immortalization as it might occur in vivo.

Senescence barriers suppress tumorigenesis and malignant progression is dependent upon disabling these barriers. We have developed an integrated model of these barriers in cultured HMEC, consistent with what is known about carcinogenesis in vivo. We believe that increased understanding and use of this model could illuminate carcinogenesis mechanisms and enable new therapeutic approaches to cancer prevention and treatment.

Cultured HMEC first arrest at stasis, a stress-associated barrier independent of telomere length and extent of replication, mediated by the RB pathway. Stasis can be bypassed or overcome by errors in the RB pathway; in cultured HMEC, loss of p16 function is common. We hypothesize that getting past stasis correlates with early clonal expansion/atypical hyperplasia in vivo. Post-stasis HMEC exhibit ongoing telomere attrition, leading to replicative senescence, the telomere dysfunction barrier due to critically short telomeres. Post-stasis HMEC with telomere dysfunction show properties similar to DCIS (short telomeres, genomic instability). Cells that aberrantly reactivate sufficient telomerase can overcome this barrier and immortalize, while also gaining resistance to oncogene-induced senescence (OIS). Thus, subsequent expression of any of numerous oncogenes into non-malignant immortal cells will readily induce malignancy-associated properties rather than OIS. Non-malignant immortal lines share many aberrant properties with malignant cells, and differ significantly from normal HMEC, which are all finite.

There is confusion in the field due to the failure to distinguish between stasis and replicative senescence (a critical barrier in human carcinoma progression not present in murine models). Many cell types experience acute stresses (e.g. oxidative damage) leading to a DNA damage response (DDR) and a p53-dependent p21 stasis arrest. This DNA damage response has been confused with the DDR resulting from critically short telomeres. The critical importance of the immortalization step in human carcinogenesis—for example, necessary for development of all breast cancer subtypes—has been obscured, hindering efforts to therapeutically target the immortalization process.

Herein is described efficient non-clonal immortalization of normal human mammary epithelial cells (HMEC) by directly targeting the two main senescence barriers encountered by cultured HMEC. The stress-associated stasis barrier, mediated by elevated levels of p16$^{INK4a}$, was bypassed using shRNA to p16 or a cyclin D1/cdk2 construct. The replicative senescence barrier, a consequence of critically shortened telomeres, was bypassed in post-stasis HMEC by c-MYC transduction. These results demonstrate that just two oncogenic agents are needed to immortally transform normal HMEC. We additionally validated that the genomic instability commonly present in human carcinomas is not required per se for immortal transformation, but needed to generate genomic errors, some of which may function to bypass or overcome tumor suppressive senescence barriers. Early passage non-clonal immortalized lines exhibited normal karyotypes. Methods based on this model of efficient HMEC immortalization, in the absence of "passenger" genomic errors, will facilitate examination of telomerase regulation and immortalization during human carcinoma progression and the development of therapeutics targeting the process of immortalization.

DESCRIPTIONS OF THE EMBODIMENTS

Figure 5:
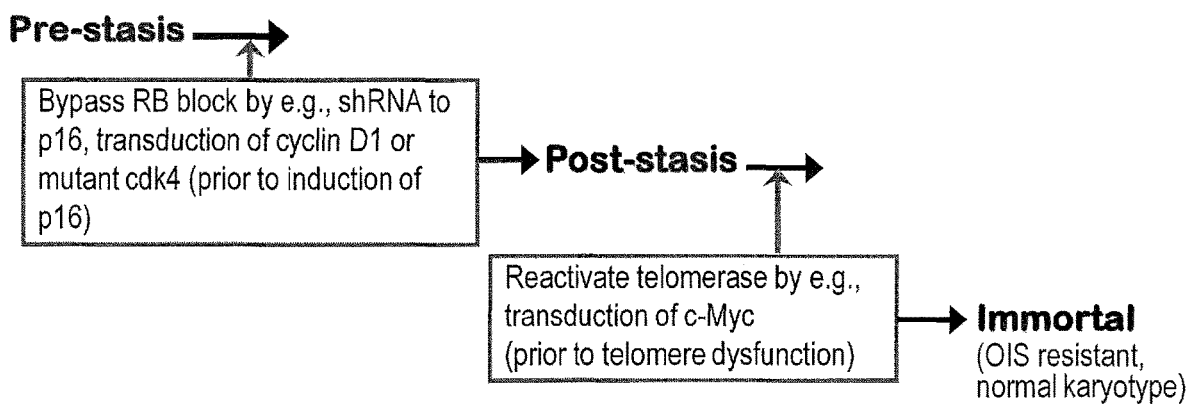
FIG. 5: Method to achieve efficient reproducible HMEC immortalization, without gross genomic errors, using pathologically relevant agents. The stasis barrier can be bypassed (before stress exposure as seen by a rise in p16 expression) by a number of errors that have been shown to be relevant to carcinoma progression in humans. These errors have in common an outcome that keeps the RB protein inactive or mutated. One common error in human carcinomas is the loss of functional p16, which may occur by multiple distinct means. Post-stasis HMEC that bypassed stasis (never encountered high stress) can be readily immortalized by transduction of c-MYC, a transactivator of hTERT. If c-MYC is given before telomeres become critically short, resulting immortalized lines may show no karyotypic abnormalities. It is possible to test other potential activators of hTERT at this stage to see if they are capable of causing immortalization.

Thus, in one embodiment, a method to efficiently and reproducibly immortalize normal human cells. In various embodiments, a method as shown schematically in FIG. 5 that is based upon a model of HMEC tumor suppressive senescence barriers and applied to normal human cells to induce immortalization with low numbers of passenger or genome errors.

In some embodiments, a method to efficiently and reproducibly immortalize normal human cells from tissues including but not limited to lung, prostate, colon, ovary, intestinal, pancreatic, breast, skin, kidney, liver, thyroid, esophageal, lymphatic, urinary, vaginal, testicular, stomach, cartilage, bone, muscle, brain, etc. In some embodiments, the tissue is from epithelial tissues. In other embodiments, the tissue is mammary or breast tissue.

In various embodiments, a method to immortalize normal human epithelial cells, the method comprising the steps of: a) providing normal pre-stasis epithelial cells in a low stress-inducing medium; b) introducing into normal pre-stasis epithelial cells a first polynucleotide construct that prevents the cell-cycle control protein Retinoblastoma (RB) from staying in an active form, wherein such introduction occurs prior to the induction of cyclin-dependent kinase inhibitor 2A (p16) and induces errors that bypass stasis; c) providing the epithelial cells that have bypassed stasis from the previous step, wherein the epithelial cells have bypassed stasis by bypassing the RB block; d) introducing into the post-stasis epithelial cells a polynucleotide construct that will induce expression of human Telomerase reverse transcriptase (hTERT) and/or telomerase activity, wherein such introduction of the polynucleotide construct occurs prior to telomere dysfunction from eroded telomeres, and whereby said introduction induces errors that reactivate sufficient telomerase activity; and e) reactivating telomerase activity thereby inducing immortalization of said post-stasis epithelial cells.

In one embodiment, a method to efficiently and reproducibly immortalize normal human mammary epithelial cells (HMEC), the method comprising the steps of: a) providing HMEC in a low stress-inducing medium; b) introducing into pre-stasis HMEC a first polynucleotide construct that prevents the cell-cycle control protein Retinoblastoma (RB) from staying in an active form, wherein such introduction occurs prior to the induction of cyclin-dependent kinase inhibitor 2A (p16) and induces errors that bypass stasis; c) providing HMEC that have bypassed stasis from the previous step, wherein the HMEC have bypassed stasis by bypassing the RB block; d) introducing into the post-stasis HMEC a polynucleotide construct that will induce expression of human telomerase reverse transcriptase (hTERT) and/or telomerase activity, wherein such introduction of the polynucleotide construct occurs prior to telomere dysfunction from eroded telomeres, and whereby said introduction induces changes that reactivate sufficient telomerase activity; and e) reactivating telomerase activity thereby inducing immortalization of said post-stasis HMEC.

In various embodiments, the human cells are grown in a low stress-inducing medium such as M87A (e.g., a medium that does not produce a rapid rise of the stress-induced molecule p16$^{INK4a}$ which is described in US Pat. Pub. No. US 2010-0022000-A1, WO2007115223, or as described in Garbe et al. Can Res 2009, all of which are hereby incorporated by reference in their entirety). Other non-stress inducing or low stress-inducing medium may be used. In some embodiments, the medium may contain other inducers to study the effect of stress and environment on the cells and the ability to bypass the stasis senescence barrier.

In some embodiments, a polynucleotide construct that prevents the cell-cycle control protein Retinoblastoma (RB) from staying in an active form is introduced to pre-stasis HMEC prior to the induction of p16. Examples of a polynucleotide construct include but are not limited to, a p16 shRNA, overexpression of a cyclin D1/CDK2 fusion protein, a mutant CDK4 protein, shRNA to Retinoblastoma. In some embodiments, other methods to inactivate RB function may be used. Inactivation of RB allows non-clonal bypass of the stasis senescence barrier by the cells to provide for populations of post-stasis cells.

In some embodiments, a polynucleotide construct that will induce expression of human telomerase reverse transcriptase (hTERT)/telomerase activity is then introduced to the post-stasis cells derived as above. In some embodiments, transduction of c-MYC will perform this function, and allow non-clonal immortalization of the post-stasis population. Other means for inducing telomerase activity or expression of hTERT are possible, and can be determined by testing additional potential hTERT inducers in the non-clonal post-stasis HMEC derived from unstressed pre-stasis HMEC.

In some embodiments, in vivo or other human cells in vitro may also employ p53-dependent p21 to enforce stasis. In those cases, non-clonal bypass of stasis may require either direct loss of RB function (e.g., by shRNA), or inactivation of p53 (e.g., by shRNA or a GSE) in addition to method steps listed above.

The immortality of the resultant lines is shown by their expression of telomerase activity and their indefinite replicative potential. The lack of gross genomic changes (passenger errors) can be shown by karyotype analysis and/or comparative genomic hybridization (CGH) analysis soon after immortalization. While lines without gross genomic errors can be generated, these lines may not necessarily remain genomically stable upon extensive passage due to potential viral errors cause by insertional mutagenesis (from the viral vectors used to transduce genetic elements) or instability instigated by deregulated c-MYC. For example, cells obtaining an error that provides a growth advantage could become more prominent in the population.

The methods described herein differ from currently used methods in that the present method uses pathologically relevant agents and can be applied to cells from multiple individuals to obtain an immortal line from any individual's cells that can be grown in primary culture before becoming highly stressed. This approach may applicable to other human epithelial cells; however HMEC are particularly useful due to the absence of p53-dependent p21 at stasis. In cell types that also engage p53 at stasis, both p16 and p53 can be inactivated (e.g., by shRNA, or by GSE inhibitor to p53) to bypass stasis, and cells then immortalized by c-MYC. While this situation may also provide immortal lines lacking gross genomic changes to start, the absence of functional p53 will likely make the resultant lines more vulnerable to genomic alterations upon stress exposures.

This method in turn provides an experimentally tractable system to examine the mechanisms underlying human cell and epithelial cell immortalization as it might occur during in vivo carcinogenesis, something that is currently largely unknown. The absence of passenger errors during the immortalization process greatly facilitates such a usage. In some embodiments, the methods and immortalized cells that are created by this process allow for comparison of the immortalized lines (lacking passenger errors) with their immediate finite precursors, to determine what properties (e.g., gene expression, epigenetic properties, etc.) differ between the isogeneic immortal and finite cells. In some embodiments, methods for testing of potential therapeutics in the resultant cells and cell lines to see if the therapeutics can prevent or reverse immortalization are provided. In other embodiments, methods for testing the post-stasis cells to determine what agents besides c-MYC may promote immortalization. In another embodiment, methods for utilizing the HMEC cultures generated from the above method to identify genes or processes that may be required to attain or maintain immortalization.

In some embodiments, finite (pre- and post-stasis) HMEC are compared to newly immortalized isogenic non-clonal HMEC lines to determine molecular differences. The assays to do this include, but are not limited to, global gene expression and global epigenetic landscape analysis. Gene expression analysis using RNA-seq and smRNA-seq reveals protein coding genes, long non-coding RNAs and miRNAs that changed expression during immortalization. Analysis of epigenetic landscape includes DNA methylation (MeDIP-seq, MRE-seq), various histone modifications (ChIP-seq) and chromatin conformation (e.g. FAIR-seq) to track the epigenetic changes linked to immortalization that might be responsible for stabilization of changes in gene expression.

To determine the statistical significance of the differences between finite and immortal HMEC and identify potential candidate relevant changes, data generated from the combined comprehensive epigenomic and genomic analyses can be analyzed using described tools (Genome analysis tools at the MIT website web.wi.mit.edu/young/research pages) with corrections for variable parameters. Based on variance between replicates and variance between experimental treatments, a global error model will be applied to each type of microarray using the adjusted log ratios to identify probes with significant changes. The significance threshold will be adjusted to account for the problem of multiple testing using the Benjamini Hochburg False Discovery Rate method with the false discovery rate set to 0.05. Genes passing these filters will be labeled as direct genetic or epigenetic targets. Genomic and epigenomic data will be analyzed in the R programming environment using Bioconductor packages (Website for r-project; Website for Bioconductor), using well-described approaches. Normalization of all data will use the Limma package. Control for false discovery rate will use a multiple testing correction method. Genes are considered statistically significant if the adjusted p-value is p<0.05. To obtain high resolution, high precision analysis of candidate genes, gene expression will be analyzed by quantitative real-time PCR. Histone modifications will be monitored using ChIP coupled to real-time PCR. DNA methylation state will be analyzed primarily by Sequenom MassArray technology.

Thus, herein are described methods and processes for direct targeting of the two senescence barriers, stasis and replicative senescence, that can reproducibly and efficiently generate immortal lines with no gross genomic changes. These data support the hypothesis that the widespread genomic changes seen in breast carcinomas are needed to generate errors that can bypass or overcome senescence barriers, but genomic instability per se is not necessary for transformation. The inherent genomic instability preceding replicative senescence may induce most genomic errors—those needed for immortalization as well as many "passenger" errors.

The diploid, non-clonal lines produced by the present methods can allow identification of immortalization-specific changes in the absence of widespread passenger mutations. Since immortalization is essential for malignancy, such changes could be therapeutic targets to prevent progression.

Therefore, the immortalization step in human carcinoma progression should be viewed as essential and rate-limiting, with many key cancer properties determined prior to immortalization (in vivo, by the DCIS stage).

In some applications, the present methods provide the ability to determine whether observed changes and/or candidate genes are needed to attain or maintain immortality, and candidate genes are tested for their effect on immortalization and conversion. Genes with increased expression can be targeted via shRNA constructs while genes with decreased expression can be transduced using retroviral vectors, or targeted by CRISPR-cas9-directed genomic changes. In some embodiments, methods and observation of the ability of candidate genes to inhibit immortalization of post-stasis HMEC transduced with c-MYC, since this protocol produces uniform immortalization. In other embodiments, methods and observation for the ability of candidate gene to prevent conversion using newly immortalized lines for which sufficient pre-conversion cell stocks are known or at hand. The potential for candidate genes to revert immortal lines to a finite state are tested using several different types of fully immortal lines.

Differences consistently shown between the post-stasis and immortal HMEC cultures will point out potential additional players in the immortalization process, and assays can assess whether these changes are necessary for the immortal state. These genes/processes could be therapeutic targets to prevent or reverse immortalization. Particularly noted is the possibility that immortalization requires epigenetic changes, since these may be more amenable to therapeutic targeting.

In some embodiments, only two oncogenic agents are sufficient to immortally transform normal finite HMEC. In other embodiments, three or more oncogenic agents are sufficient to malignantly transform normal finite HMEC. In various embodiments, methods for screening for those oncogenic agents are provided.

In some embodiments, a method for screening the effect of toxin on cancer progression comprising the steps of: a) providing normal cells in a low stress-inducing medium; b) introducing a toxin to said pre-stasis cells, wherein such introduction occurs prior to the induction of cyclin-dependent kinase inhibitor 2A (p16) and induces errors that bypass stasis; c) providing HMEC that have bypassed stasis from the previous step, wherein the cells have bypassed stasis by bypassing the RB block; d) screening said post-stasis cells for differential expression profiles from the normal HMEC and/or sequencing said post-stasis cells to compare the genetic errors induced to bypass stasis.

In another embodiment, a method for screening the effect of toxins on cancer progression comprising the steps of: a) providing cells in a low stress-inducing medium; b) introducing into pre-stasis HMEC a first polynucleotide construct that prevents the cell-cycle control protein Retinoblastoma (RB) from staying in an active form and allowing said cells to bypass stasis, wherein such introduction occurs prior to the induction of cyclin-dependent kinase inhibitor 2A (p16) and induces errors that bypass the RB block and stasis; c) providing cells that have bypassed stasis from the previous step, wherein the cells have bypassed stasis by bypassing the RB block; d) introducing to the post-stasis cells an agent to determine if the agent induces expression of human telomerase reverse transcriptase (hTERT) and/or telomerase activity, wherein such introduction of the polynucleotide construct occurs prior to telomere dysfunction from eroded telomeres; and e) screening for induction of errors that reactivate telomerase activity thereby inducing immortalization of said post-stasis cells.

Such agents that may be tested using the resultant cells may include but are not limited to common ions and chemicals, household and environmental chemicals and toxins found in consumer products, pathogens, carcinogens, analytes, agents, proteins, polynucleotides, hormones, polymers, foods, preservatives, drugs, therapeutics, small molecules, organic molecules, or other environmental agents such as radiation, soil, gas levels, or other organic matter.

Example 1: Immortalization of Normal Human Mammary Epithelial Cells in Two Steps by Direct Targeting of Senescence Barriers without Gross Genomic Alterations Our previous studies have used pathologically relevant agents to transform normal finite lifespan human mammary epithelial cells (HMEC) to immortality[6-9]. However, immortalization was clonal with multiple genomic errors present in immortalized lines[1], and the alterations specifically responsible for immortalization were not fully identified. The sporadic nature of the immortalization events has prevented examining the immortalization process as it occurs. We therefore sought to define a reproducible protocol, using agents that might recapitulate molecular alterations occurring during in vivo breast cancer progression, which could achieve non-clonal transformation of normal HMEC to immortality. Design of this protocol was based on our model of the tumor-suppressive senescence barriers normal HMEC need to bypass or overcome to attain immortality and malignancy[6,10] (see FIGS. 1A and 1B). Further, we wanted to determine whether direct targeting of senescence barriers could generate immortal lines lacking gross genomic errors. Cultured HMEC can encounter at least three distinct tumor-suppressive senescence barriers[6,10,11]. A first barrier, stasis, is stress-associated and mediated by the retinoblastoma protein (RB). HMEC at stasis express elevated levels of the cyclin-dependent kinase inhibitor CDKN2A/p16$^{INK4a}$ (p16), and do not show genomic instability or critically short telomeres[10,12,13]. A second barrier, replicative senescence, is a consequence of critically shortened telomeres from ongoing replication in the absence of sufficient telomerase, and is associated with telomere dysfunction, genomic instability, and a DNA damage response (DDR)[5,6,10,13,14]. When functional p53 is present, this barrier has been called agonescence; cell populations remain mostly viable. If p53 function is abrogated, cells enter crisis and eventually die[6]. Overcoming the third barrier, oncogene-induced senescence (OIS), is associated with acquiring telomerase activity and immortalization; thus a single additional oncogene can confer malignancy-associated properties once a cell is immortally transformed[11,15].

By exposing normal pre-stasis HMEC to different culture conditions and oncogenic agents, we have generated numerous post-stasis and immortal HMEC with distinct phenotypes. HMEC grown in our original MM medium ceased growth at stasis after ~15-30 population doublings (PD) (FIG. 1B, upper panel), but rare clonal outgrowths emerged after primary cultures were exposed to the chemical carcinogen benzo(a)pyrene (BaP), generating the BaP post-stasis populations (originally termed Extended Life)[7,16]. BaP post-stasis cultures examined lacked p16 expression, due to gene mutation or promoter silencing[12,17,18], and grew an additional 10-40 PD before agonescence. Rare immortal lines have emerged from BaP post-stasis populations at the telomere dysfunction barrier. Pre-stasis HMEC grown in serum-free MCDB170 medium showed more limited proliferative potential, with a rapid rise in p16 expression leading to stasis by ~10-20 PD; cells at stasis exhibited abundant stress fibers[12,19]. MCDB170 induces rare post-stasis cells, called post-selection, with silenced p16 as well as many other differentially methylated regions (DMR)[12,18]. Post-selection post-stasis HMEC proliferate for an additional 30-70 PD before the population ceases growth at agonescence. Immortal lines were produced by transducing BaP and post-selection post-stasis HMEC with the breast cancer-associated oncogenes c-MYC and/or ZNF217[1,8]. In those studies, transduced c-MYC, a transactivator of hTERT, did not by itself immortalize post-selection post-stasis HMEC; however, when c-MYC was later transduced into the BaP post-stasis culture 184Aa, uniform immortalization was observed. Consequently, we tested the hypothesis that exposure to highly stressful (i.e., rapid p16-inducing) culture environments such as growth in serum-free MCDB170 produced post-stasis populations refractory to c-MYC induction of telomerase, whereas post-stasis cells that had not experienced high stress could be immortalized by c-MYC.

In the current studies, additional, independently derived BaP post-stasis cultures also showed induction of telomerase activity and uniform immortalization following c-MYC transduction. However, these BaP-exposed p16(-) cells harbor BaP-induced small genomic and epigenomic errors ([18,20]). We therefore generated and examined the effect of c-MYC transduction on HMEC populations made post-stasis by transduction of shRNA to p16 (p16sh) or a cyclin D1/cdk2 construct into unstressed pre-stasis cells. In addition to trying to achieve reproducible non-clonal immortalization, we wanted to examine whether direct targeting of the stasis and replicative senescence barriers could produce immortalized lines without gross genomic changes. We report that transduction of p16sh or a cyclin D1/cdk2 construct to bypass stasis, followed by transduced c-MYC to induce hTERT, efficiently immortalized pre-stasis HMEC populations grown in low stress-inducing media. Resultant immortalized lines possessed a normal karyotype at early passages, and none to few genomic copy number changes at higher passages. The failure of c-MYC to immortalize the p16(-) post-selection post-stasis HMEC was not due to differences in the hTERT gene locus DNA methylation state, or repressive (H3K27me3) or permissive (H3K4me3) histone modifications. These data indicate that just two oncogenic agents are sufficient to immortally transform unstressed normal HMEC, and support our hypothesis that the genomic instability commonly present in human carcinomas may not be required per se for transformation, but is needed to generate errors that can bypass or overcome tumor suppressive barriers.

Results

Immortalization of HMEC by p16sh and c-MYC

Figure 1B:
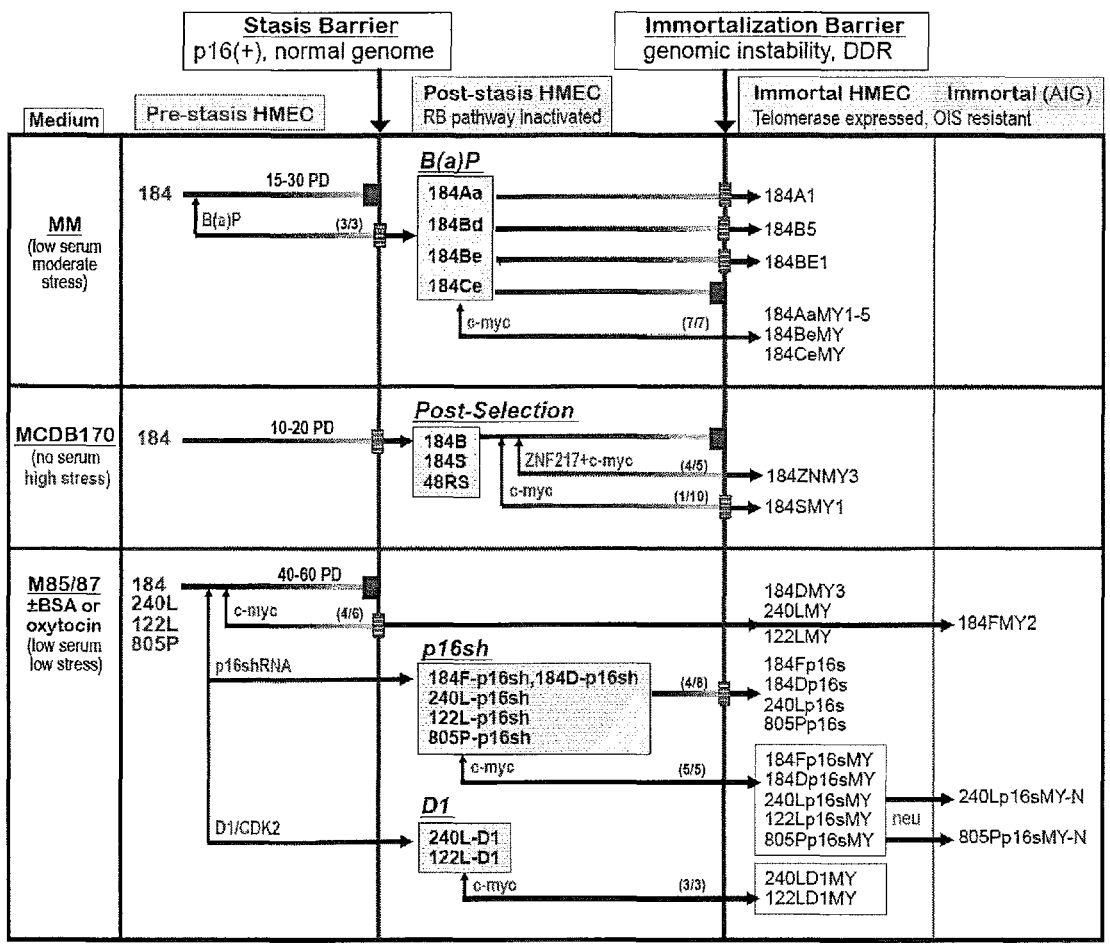
FIG. 1B: Derivation of isogenic HMEC from specimens 184, 240L, 48R, 122L and 805P at different stages of transformation ranging from normal pre-stasis to malignant. Cells were grown in media varying in stress induction, measured by speed of increased p16 expression (left column), and exposed to various oncogenic agents (red). The distinct types of post-stasis HMEC are shown in the middle column (blue); nomenclature for types is based on agent used for immortalization (e.g., BaP; p16sh) or historical naming (e.g., post-selection). Transduced finite cultures are indicated by specimen number and batch (e.g., 184F, 184D, 184B) followed by a "−" and the agent transduced (e.g., −p16sh); the BaP post-stasis nomenclature is based on original publications, and includes specimen number and batch (e.g., 184A, 184B, 184C). New non-clonal immortalized lines described herein are outlined in the right columns; nomenclature is based on the oncogenic agents employed (e.g., p16s for p16sh, MY for c-MYC). Numbers in parentheses before the barriers indicate how many time there was clonal or non-clonal escape from that barrier out of how many experiments performed (e.g., c-MYC-transduced pre-stasis HMEC were cultured to stasis 4 times; in 3 experiments there was clonal escape from stasis leading to 3 clonally immortalized lines)
Figure 2:
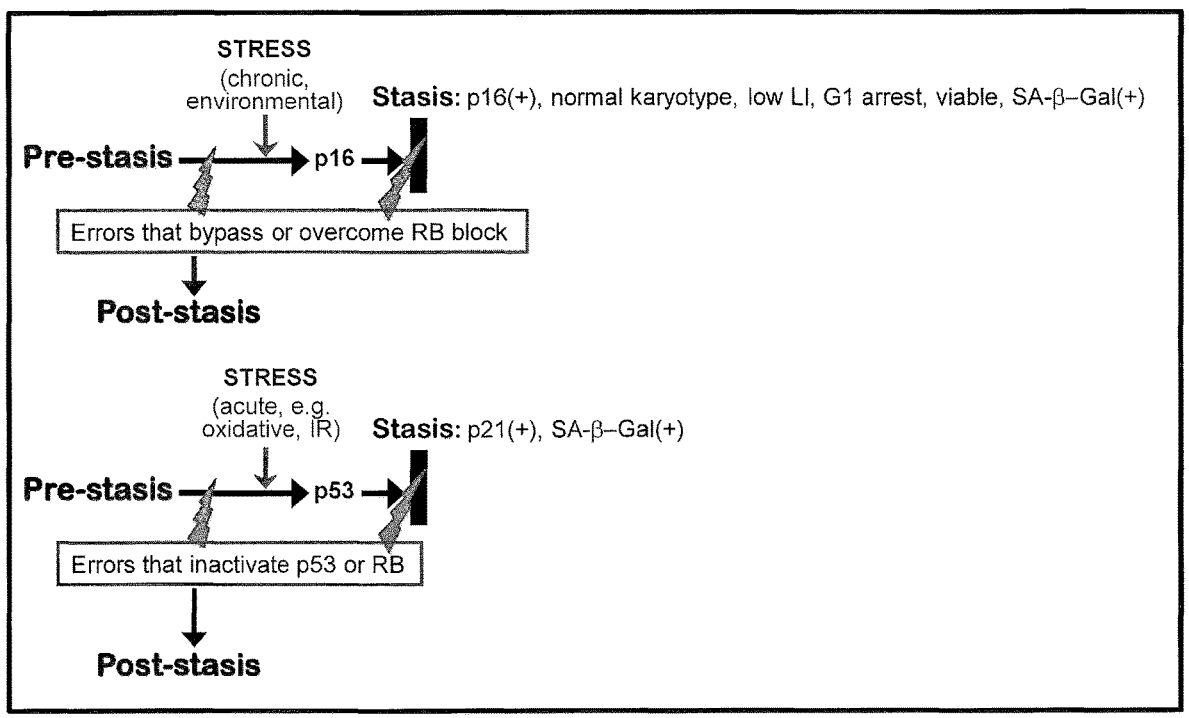
FIG. 2: Stasis may be enforced by both/either p16 and/or p21 keeping RB in an active state. Acute stresses, such as those that cause DNA damage (e.g., oxidative damage and irradiation) may induce p53-dependent p21, which will block RB inactivation and lead to stasis. We have not observed p21 expressed in unperturbed cultured HMEC at stasis, but this type of stasis could occur in vivo or in vitro if cells are exposed to agents that produce DNA damage. If p53-dependent stasis is engaged, then loss of p53 function would be a common way to bypass/overcome this barrier; loss of RB function could also be effective.
Figure 3:
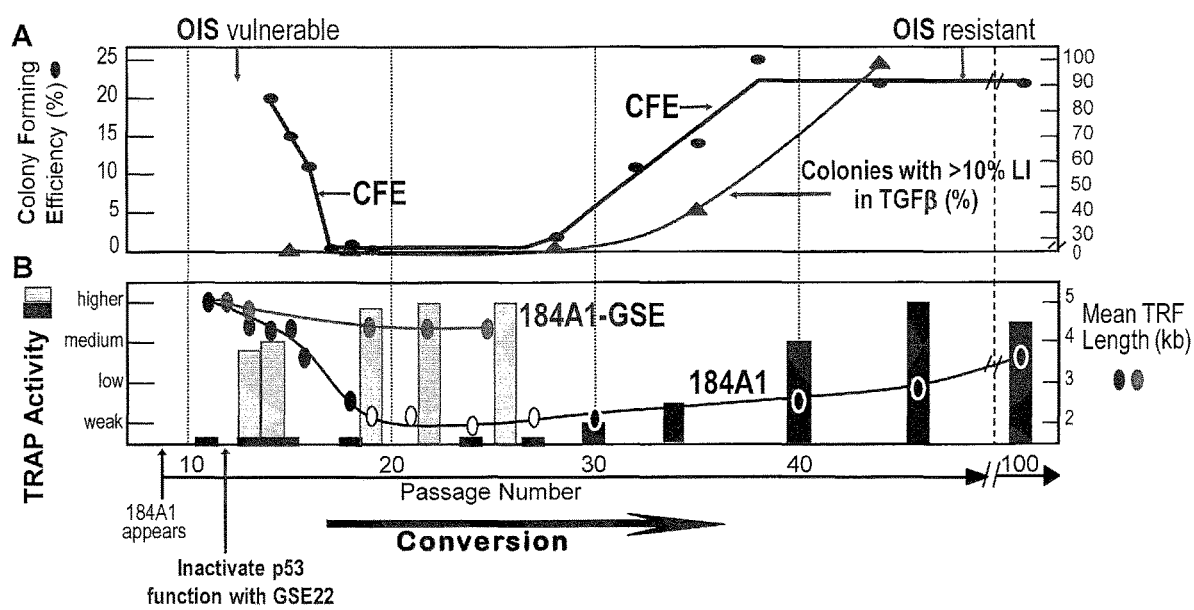
FIG. 3: Full reactivation of telomerase activity in cultured HMEC requires a conversion process.
Figure 4:
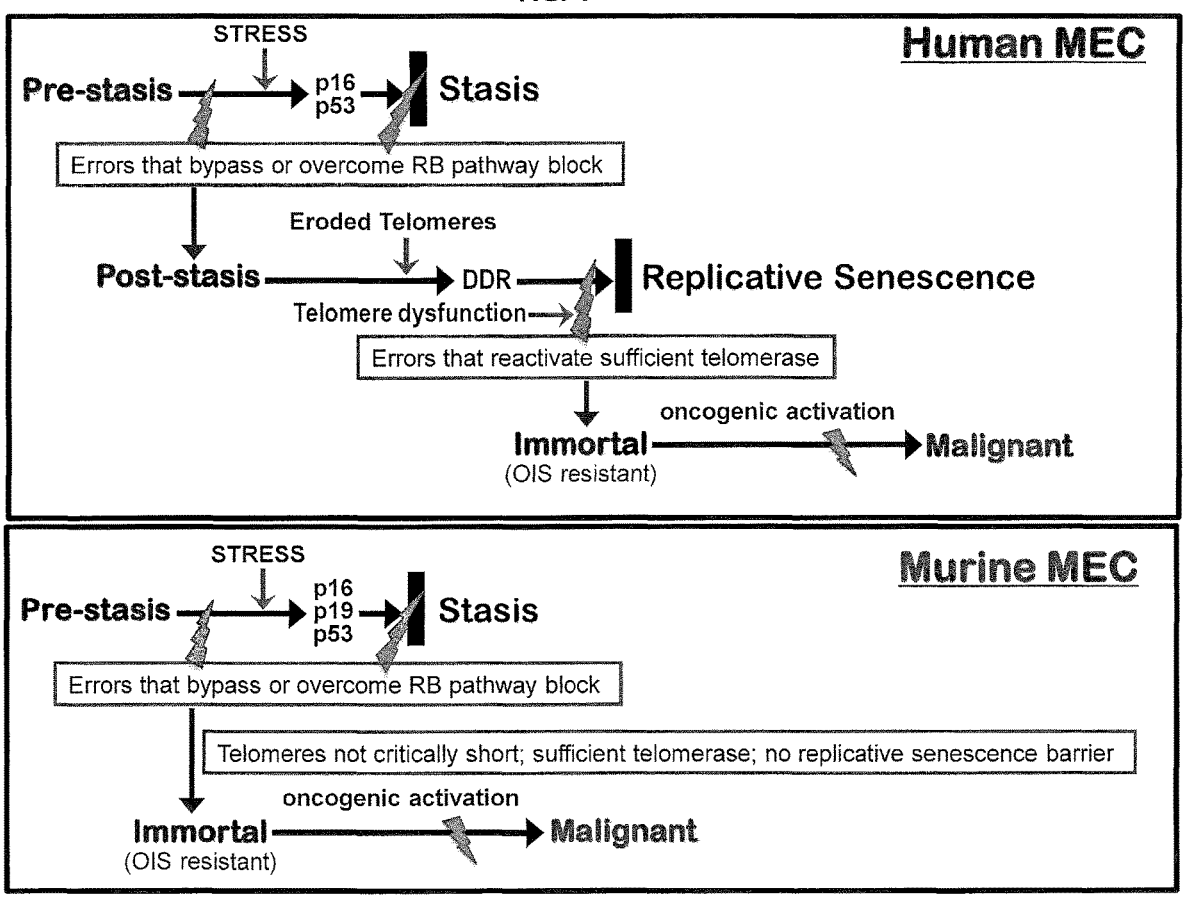
FIG. 4: Small short-lived animals such as mice and rats do not encounter a significant replicative senescence barrier to immortalization. Small short-lived animals, unlike humans, do not have stringent repression of telomerase activity in adult non-stem cells. Additionally, most such small animals used for cancer research have very long telomeres, much longer than normal human. Thus, once they bypass or overcome the stasis barrier, they can readily immortalize. Consequently, the small animals models commonly used for cancer research do not model the key immortalization step in human carcinoma progression, and cannot be used to accurately examine this step, or what might prevent this step.
Figure 15A:
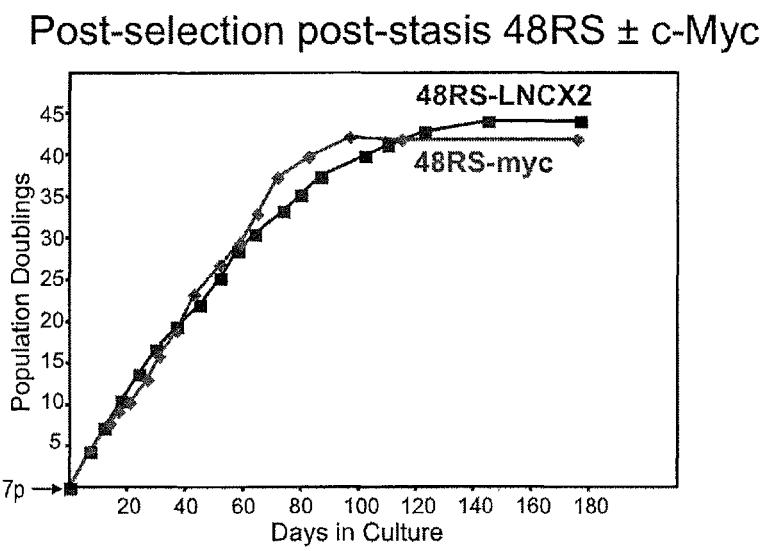
FIG. 15A-15E: Effect of c-MYC and p16sh on HMEC growth and TRAP activity.

FIG. 1A illustrates our model of the senescence barriers encountered by cultured primary HMEC and FIG. 1B shows the derivation and nomenclature of the finite and immortalized HMEC described in this study, and the agents employed to promote bypass or overcoming of the senescence barriers. In ten independent experiments, c-MYC transduction of the post-selection post-stasis HMEC produced only one instance of clonal immortalization, generating the 184SMY1 line (FIG. 1B middle panel). FIG. 10A shows the growth of post-selection 184B following transduction with c-MYC or control vector; net growth ceases at replicative senescence at passage (p) 15 in both conditions. Telomerase activity was examined using the TRAP assay in cells from this experiment, as well as one using the 184S post-selection batch, which ceases net growth at 22p. In both cases, no significant TRAP activity could be detected in either control or c-MYC transduced populations, consistent with the failure to immortalize. Similar results were seen using post-selection post-stasis HMEC from another specimen, 48RS (FIG. 15A).

Figure 10B:
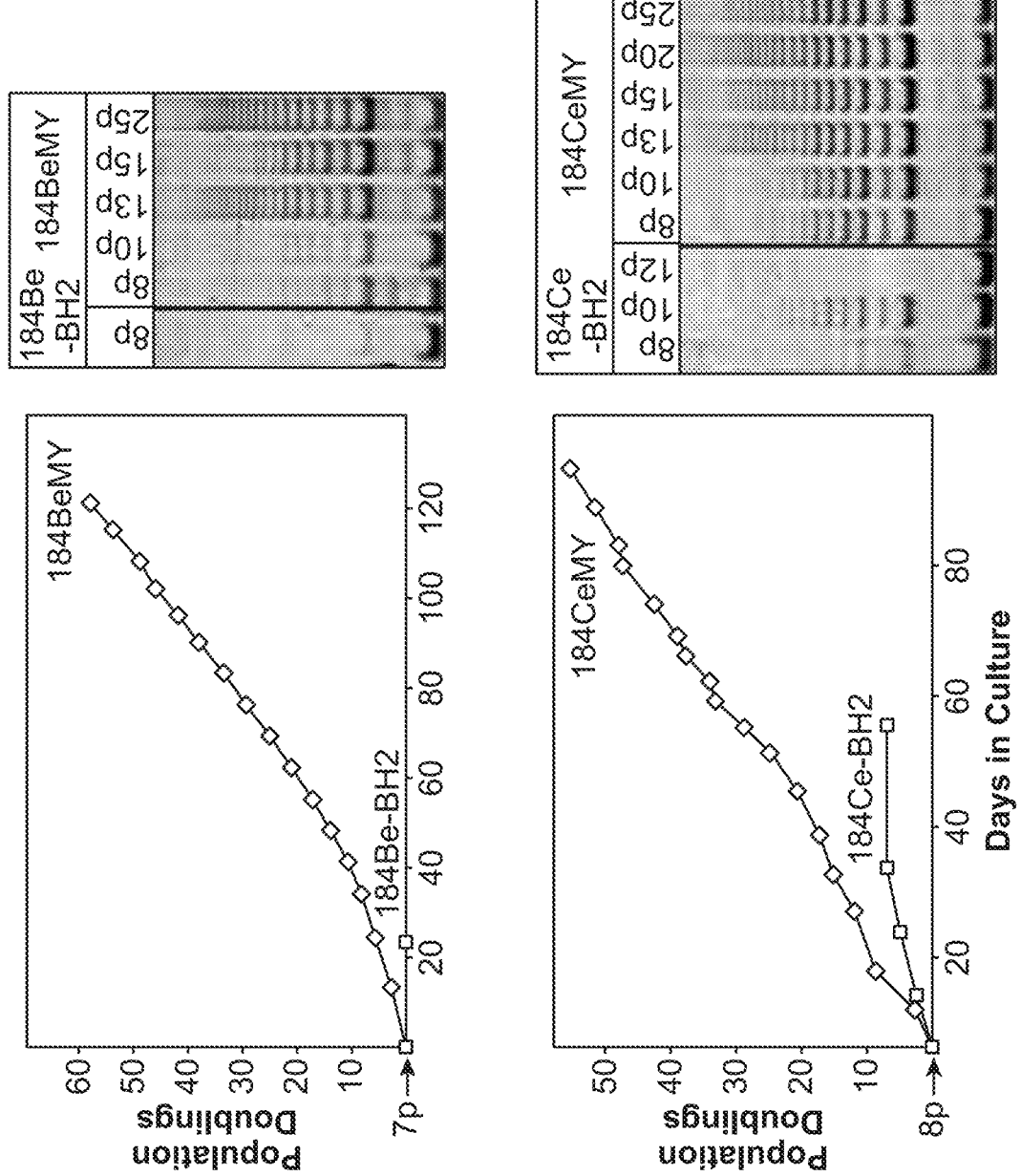
Figure 10C:
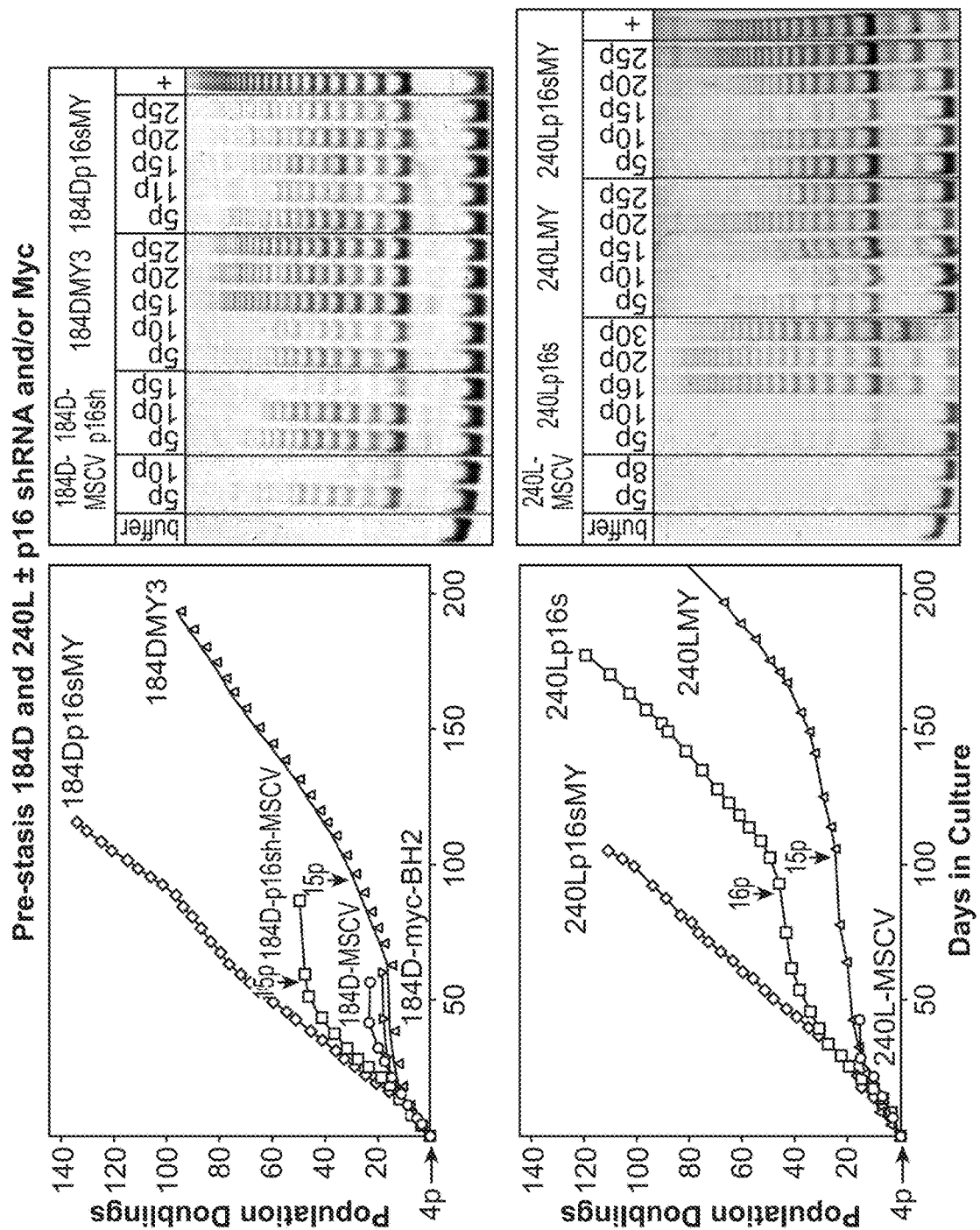
FIG. 10C. Pre-stasis 184D and 240L HMEC grown in M87A+CT+X were transduced at 3p with a p16sh-expressing retrovirus (MSCV, blue) or empty vector (black). At 4p cultures ±p16sh were transduced with c-MYC (BH2)(red+ p16sh; purple −p16sh). c-MYC-transduced p16sh post-stasis HMEC maintained active growth indefinitely, associated with increased TRAP activity. The continuous exponential growth following c-MYC transduction of the 4p p16sh-post-stasis populations reflects the observed non-clonal immortalization. Cells transduced with p16sh alone bypassed stasis and ceased net growth at agonescence, with rare clonal immortalization at agonescence. Cells transduced with c-MYC alone ceased growth at stasis, with rare clonal escape from stasis leading to immortalized lines. Control cultures transduced with empty vectors ceased growth at stasis. In some TRAP assays, heat-treated controls (+) were run next to unheated (−) samples. Positive TRAP control samples are indicted by "+".

In contrast, c-MYC transduction into the BaP post-stasis culture, 184Aa, produced continuous cell growth with increasing TRAP activity (FIG. 1B). Similar results were seen in 5 independent experiments, generating the non-clonally immortalized lines 184AaMY1-5 (FIG. 10B upper panel). While both these post-stasis types lack p16 expression, this was due to mutation in 184Aa and promoter silencing in the post-selection HMEC[12,17]. We therefore tested the effect of c-MYC transduction in two additional independent BaP post-stasis cultures that exhibited p16 promoter silencing, 184Be and 184Ce[12,18]. Both populations showed continuous growth and increasing TRAP activity following c-MYC transduction, generating the non-clonally immortalized lines 184BeMY and 184CeMY (FIGS. 1B and 10B). These data indicate that these two different types of p16(-) post-stasis HMEC, BaP and post-selection, differ significantly in response to c-MYC transduction.

Figure 6D:
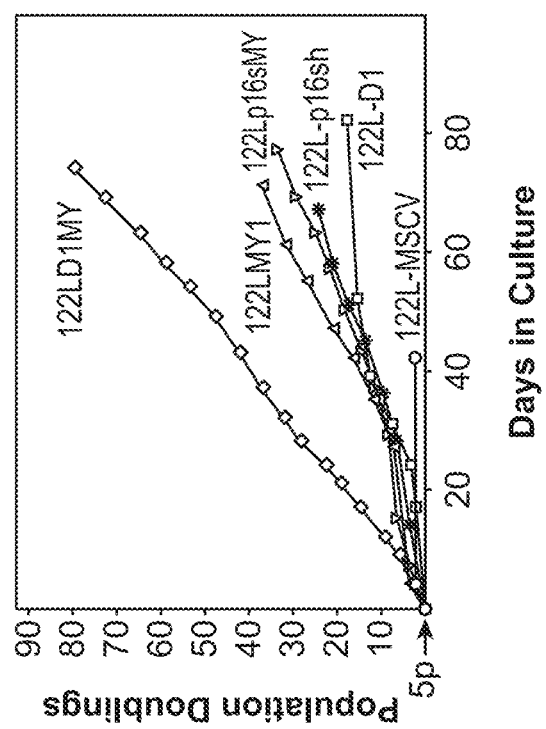
Figure 6C:
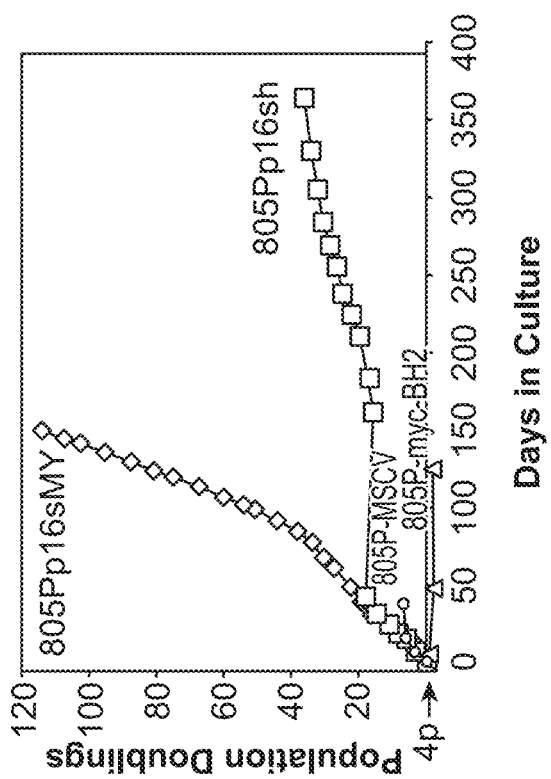
Figure 15C:
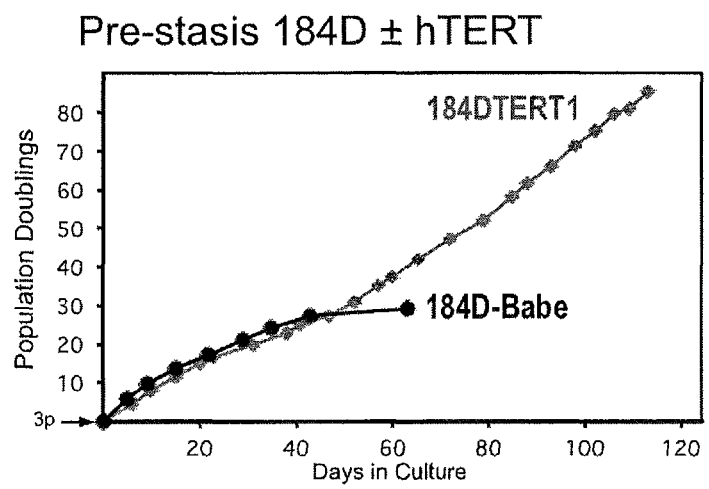
Figure 15D:
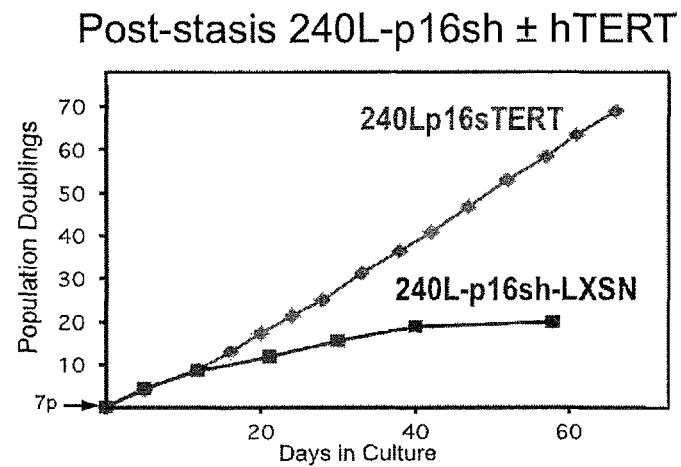
Figure 15B:
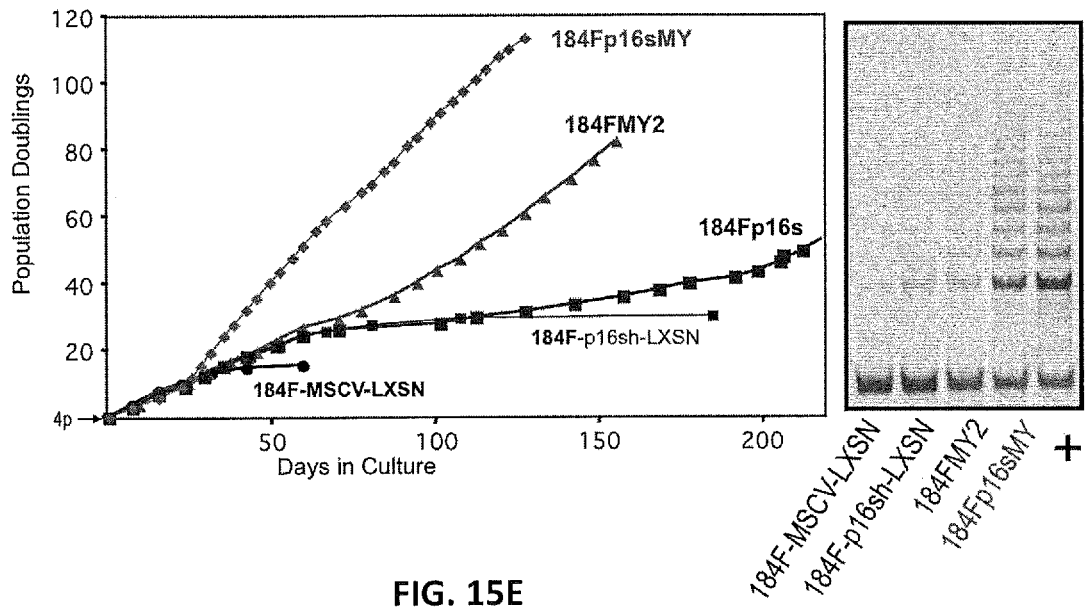

We then examined the effect of transduced c-MYC on HMEC made post-stasis by direct knockdown of p16 using p16sh, or a cyclin D1/cdk2 construct (FIG. 6AB). The non-clonal p16sh- and D1-post-stasis populations would not harbor the BaP-induced errors present in the clonal BaP post-stasis cultures, and do not contain the extensive DMR present in the post-selection post-stasis HMEC[18]. These studies used pre-stasis HMEC grown in media formulations (M87A or M85) that delay the onset of p16 expression and support up to ~60 PD[10]. Early passage pre-stasis HMEC from specimens 240L, 122L, and 805P, and two batches from specimen 184 were transduced with p16sh-containing, a cyclin D1/cdk2 containing, or a control retrovirus construct, followed by c-MYC or control transduction at the next passage (FIG. 6AB, FIG. 15B). At these early passages, <10% of the population expressed p16 protein[10]. Control cultures ceased growth at stasis, and p16sh- or D1-transduced cultures ceased growth at replicative senescence, with rare exceptions. p16sh post-stasis cultures that received c-MYC showed uniform continuous growth and TRAP activity, generating the non-clonal immortal lines 184Dp16sMY, 184Fp16sMY, 240Lp16sMY, 122Lp16sMY, 805Pp16sMY; D1 post-stasis cultures that received c-MYC also showed uniform continuous growth and TRAP activity, generating the non-clonal immortal lines 240LD1MY and 122LD1MY (FIG. 10B lower panel). These studies indicate that the ability of c-MYC to induce rapid uniform immortalization in post-stasis HMEC is not dependent upon pre-existing genomic errors.

Almost all pre-stasis HMEC receiving c-MYC alone ceased growth at stasis; however clonal outgrowths of rare cells that escaped stasis by unknown means produced clonal immortal lines (184DMY3, 184FMY2, 240LMY, 122LMY; FIG. 1B lower panel) with increased TRAP activity following the passages where most cells stopped at stasis (FIG. 6A). For example, pre-stasis 184D-myc initially stopped growth by 8-10p. However, a culture reinitiated from 5p frozen stocks exhibited 1-2 clonal outgrowths per dish at 9p, against a background of senescing cells; these colonies maintained growth, generating the 184DMY3 line. We presume that once this population became post-stasis, the transduced c-MYC could immortalize it similar to the effect of c-MYC on the BaP and p16sh post-stasis populations. Although we have never observed spontaneous immortalization at the telomere dysfunction barrier in unperturbed post-selection post-stasis HMEC (cells that had experienced high pre-stasis culture stress), rare clonal outgrowths in a background of senescent cells were seen at this barrier in some p16sh post-stasis cultures (cells that had bypassed stasis prior to p16 elevation). These colonies maintained growth, generating the clonal immortal lines 184Fp16s, 184Dp16s, 240Lp16s, 805Pp16s (FIG. 1B lower panel). The immortalization-producing error in 184Fp16s must have occurred after 9p, since re-initiation of frozen 9p184F-p16sh stock did not yield an immortal line (FIG. 15B). We hypothesize that the difference in spontaneous immortalization in the post-selection vs p16sh post-stasis HMEC, during the period of genomic instability, is related to the need for multiple errors for telomerase reactivation in the post-selection cells compared to the ability of just one error, such as transduced c-MYC, to immortalize the p16sh post-stasis HMEC. Altogether, these data suggest that a prior exposure to high culture stress may invoke alterations preventing c-MYC induction of hTERT in post-stasis populations.

Exposure of pre-stasis HMEC to high culture stress also influenced the ability of hTERT to produce efficient immortalization. Previous studies indicated that hTERT could not immortalize pre-stasis HMEC grown in high stress media such as MCDB170/MEGM[21], and yielded only one p16(-) clonal line (184FTERT) when transduced into 3p HMEC grown in moderate stress MM medium[22]. In contrast, hTERT transduced into 3p HMEC grown in low stress M87A efficiently immortalized the population, with no growth slowdown at the stasis barrier (184DTERT, FIG. 15C). As expected, given hTERT's ability to immortalize post-selection post-stasis HMEC[21,22], transduction of hTERT into the p16sh post-stasis cells 240L-p 16sh also produced efficient immortalization (240Lp16sTERT, FIG. 15D), with continuous growth similar to that seen following c-MYC transduction of 240L-p16sh (FIG. 6B).

We previously reported that proliferative pre-stasis HMEC grown in MM exhibit low levels of TRAP activity at 4p[23]. Pre-stasis HMEC from specimen 184 grown in M85/M87A also show low TRAP activity at early passages, but activity is not detectable when the cells approach stasis (FIGS. 6A; 15E). Transduction with p16sh appeared to slightly increase TRAP activity compared to controls, with levels reduced by agonescence (FIG. 6A; FIG. 15B). The low TRAP activity in unperturbed 240L was increased by p16sh transduction, while the immortalized clonal line 240Lp16s emerged from replicative senescence with robust TRAP activity (FIG. 6B). c-MYC alone transiently increased TRAP activity in proliferative pre-stasis populations, with further increased activity seen in immortalized lines (184DMY3, 240LMY).

The effect of transduced p16sh in reducing p16 protein expression is shown by Western analysis in FIG. 11A for the finite and immortal cultures, and by immunochemistry for post-stasis 184D-p16sh and immortal 184DMY3 FIG. 11C. 184B post-stasis post-selection cells, known to have silenced p16, are used as a negative control. As previously shown, higher passage pre-stasis 184D and 240LB express significant p16; transduction of p16sh reduced most but not all p16 expression in both the p16sh post-stasis HMEC, and the immortal lines derived from them. p16 protein was seen in two of the MYC-alone transduced clonal immortal lines; the high expression in 240LMY suggests that an error elsewhere in the RB pathway enabled the cell giving rise to that line to bypass stasis, while the mixed p16 expression and two distinct morphologies present in 184DMY3 suggests it consists of two distinct clones, one of which retains p16 expression. HMEC lines containing transduced c-MYC showed variably increased MYC expression levels compared to normal pre-stasis HMEC (FIG. 11B). Of note, MYC levels in c-MYC-transduced normal pre-stasis HMEC were not significantly elevated, but were increased in abnormal post-selection 184B-myc, which did not immortalize. As has been suggested for cancer cells[24], dysregulation of MYC, as well as increased expression, may play a role in carcinogenesis, and in some circumstances, low level deregulated c-MYC may be more efficient at oncogenesis than overexpressed c-MYC[25,26].

Figure 7D:
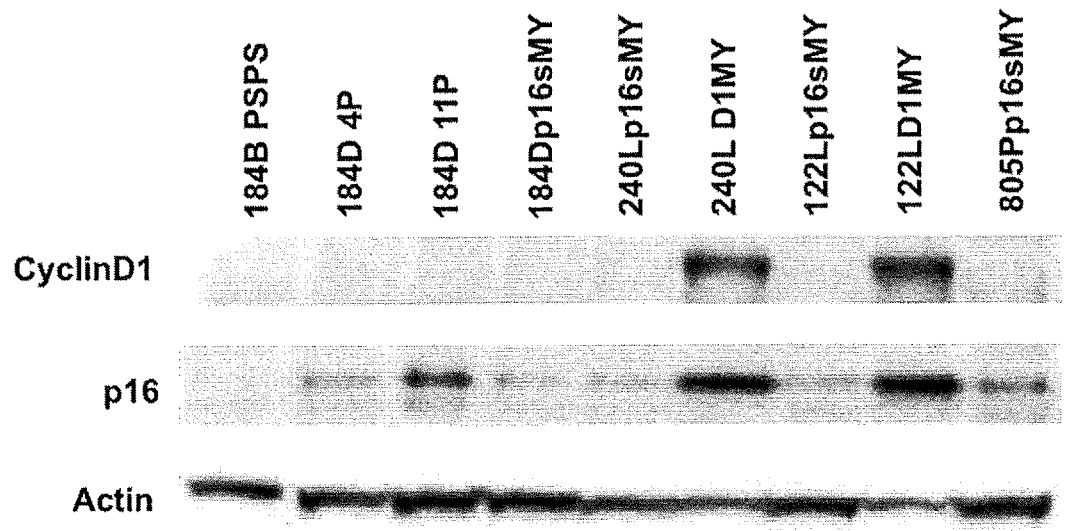
FIG. 7D shows the western blot analysis of cyclin D1 and p16 protein levels in cell lysates from non-clonal non-malignant immortal HMEC cell lines.
Figure 9A:
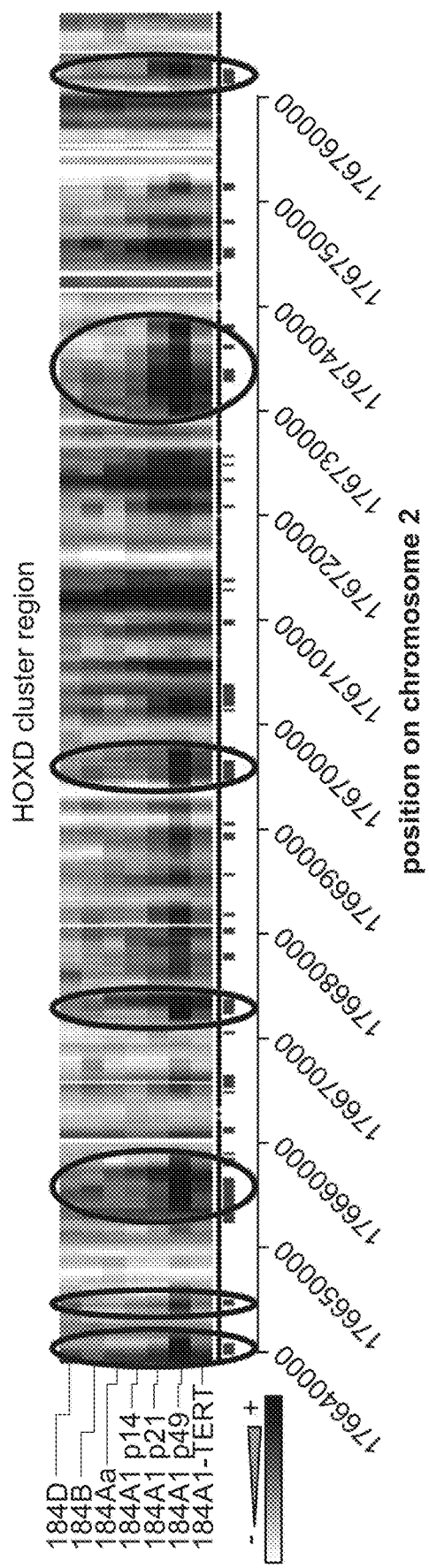
FIGS. 9A and 9B: Epigenetic changes may be involved in the conversion process during immortalization.
Figure 9B:
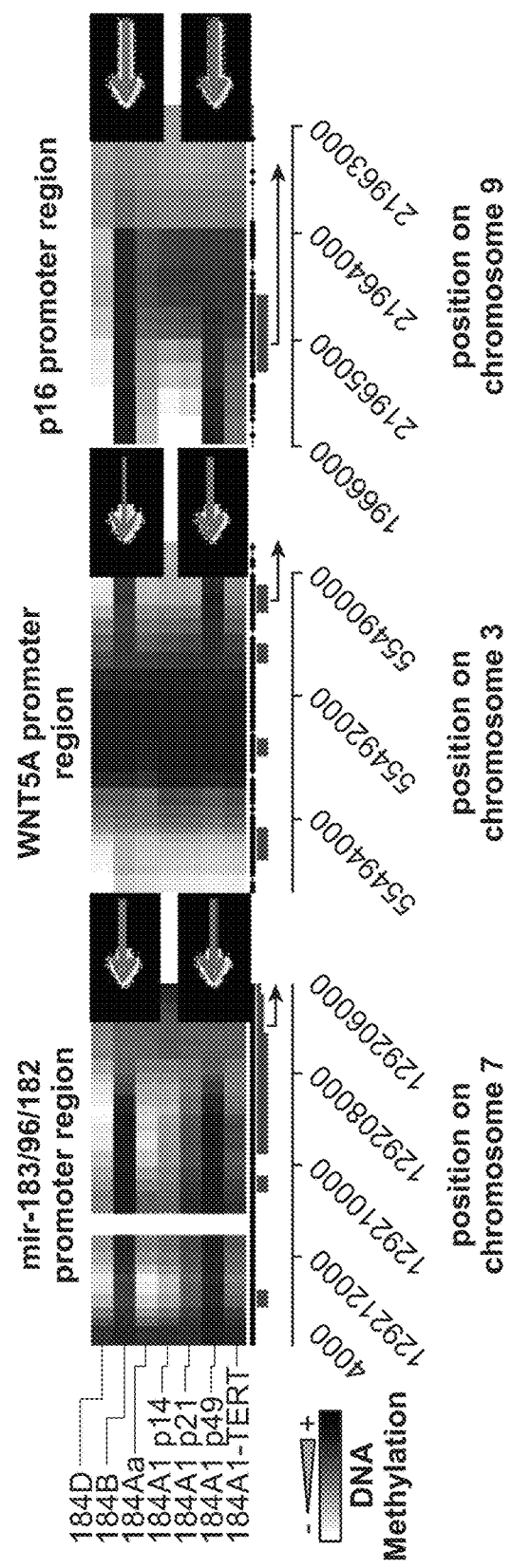

The effect of transduced cyclin D1 in elevating cyclin D1 expression is shown by Western analysis in FIG. 7D for the finite and immortal cultures. Only the lines that received cyclin D1 show elevated levels of D1, as well, as expected, of p16.

Altogether, these data indicate that post-selection post-stasis HMEC are refractory to c-MYC-induced telomerase induction and immortalization, while other post-stasis types are readily immortalized by c-MYC, and may be more vulnerable to immortalization from errors generated during telomere dysfunction. Most significantly, the data show that normal HMEC can be efficiently immortalized with endogenous telomerase reactivation by just two pathologically relevant oncogenic agents, p16sh and c-MYC.

Genomic Profiles of Immortally Transformed HMEC Lines

Figure 16A:
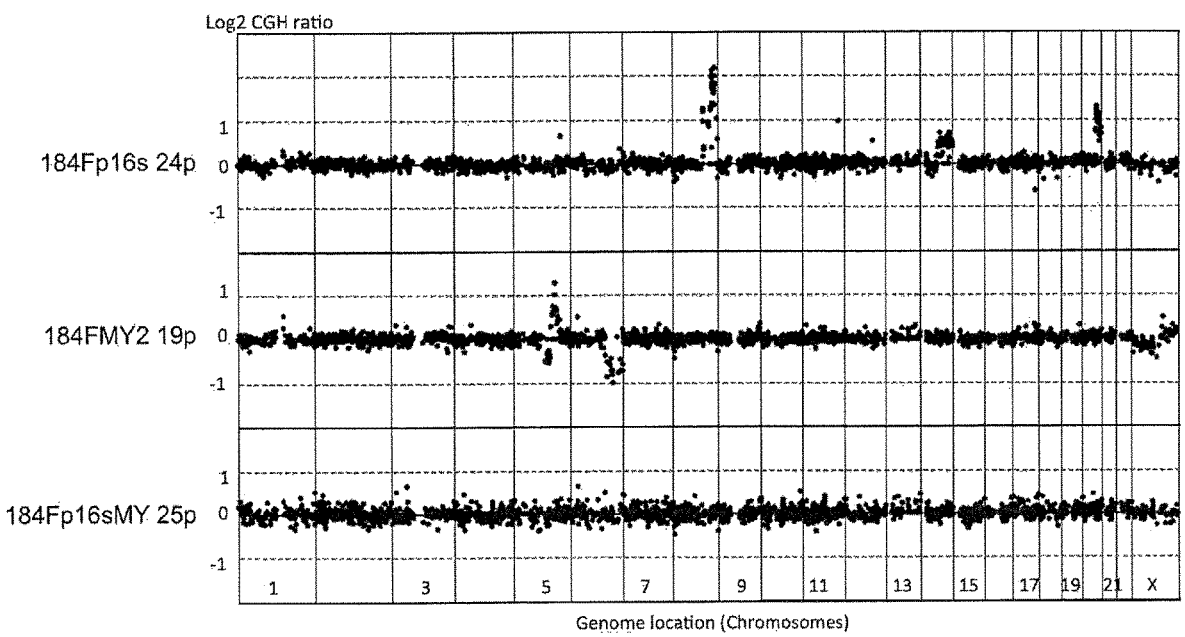
FIGS. 16A and 16B.
Figure 16B:
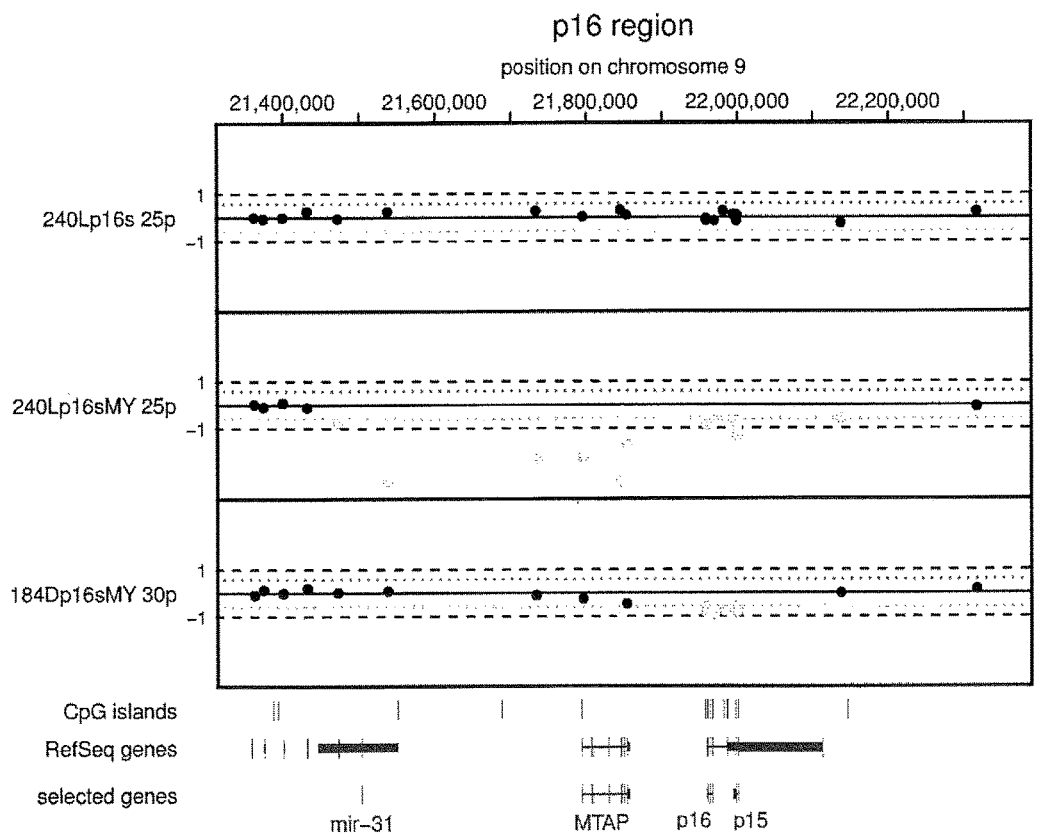

The studies described above have produced at least 18 new non-hTERT immortalized HMEC lines (FIG. 1B, shown in right column). To examine the role of genomic errors in their generation, lines were assayed for karyotype and/or genome copy number by array (a) CGH. Karyotype at early passages following immortalization was determined for the non-clonally immortalized lines 184AaMY1 (17p), 184BeMY (11p), 184CeMY (12p), 184Fp16sMY (16p), 184Dp16sMY (16p), and 240Lp16sMY (16p) (Table 1, FIGS. 7A and 7C). aCGH was performed on these, and additional clonal lines, at higher passages (FIG. 7B, FIG. 16). Clonal lines exhibited numerous copy number changes, consistent with a need to generate genomic errors to bypass or overcome stasis in the MYC-alone lines, and replicative senescence in the p16sh-alone lines. Some genomic errors, e.g., 1 q and 20 q amplification, are commonly seen in breast cancer[27].

The karyotype of all five p16sh-MYC-derived lines, two D1-MYC lines, and one of the three BaP-MYC lines (184CeMY), showed no abnormalities at early passage. At higher passages, 1-2 copy-number changes were observed in 184Dp16sMY (30p) and 240Lp16sMY (25p). Both contained small deletions in the p16 locus on 9p21 that would not be obvious by karyology (FIG. 16B), and a subpopulation of 240Lp16sMY showed a 1 q amplification. MYC-induced 9 induced genomic instability and/or retroviral-induced insertional mutagenesis could have produced a 1 q error conferring preferential growth to a 240Lp16sMY cell. The origin of the 9p deletion in lines that had received both p16sh and c-MYC is currently unknown. The gross genomic errors in 184AaMY1 and 184BeMY are likely due to these post-stasis cultures being transduced with c-MYC close to the point of agonescence (FIG. 10B), when the populations would already contain cells with genomic errors due to telomere dysfunction[13], as these errors are not present in earlier passages of 184Aa or 184Be[20].

In summary, by targeting the stasis and telomere dysfunction barriers with p16sh or cyclin D1, and c-MYC respectively, we could transform normal finite lifespan pre-stasis HMEC to immortality in the absence of gross genomic changes. These data are consistent with our hypothesis that cancer-associated genomic changes are needed to bypass or overcome tumor suppressive barriers and gain malignant properties, but gross genomic changes per se are not inherently necessary for cancer-associated immortalization.

Epigenetic State of the hTERT Promoter in the Cultured HMEC

Figure 13A:
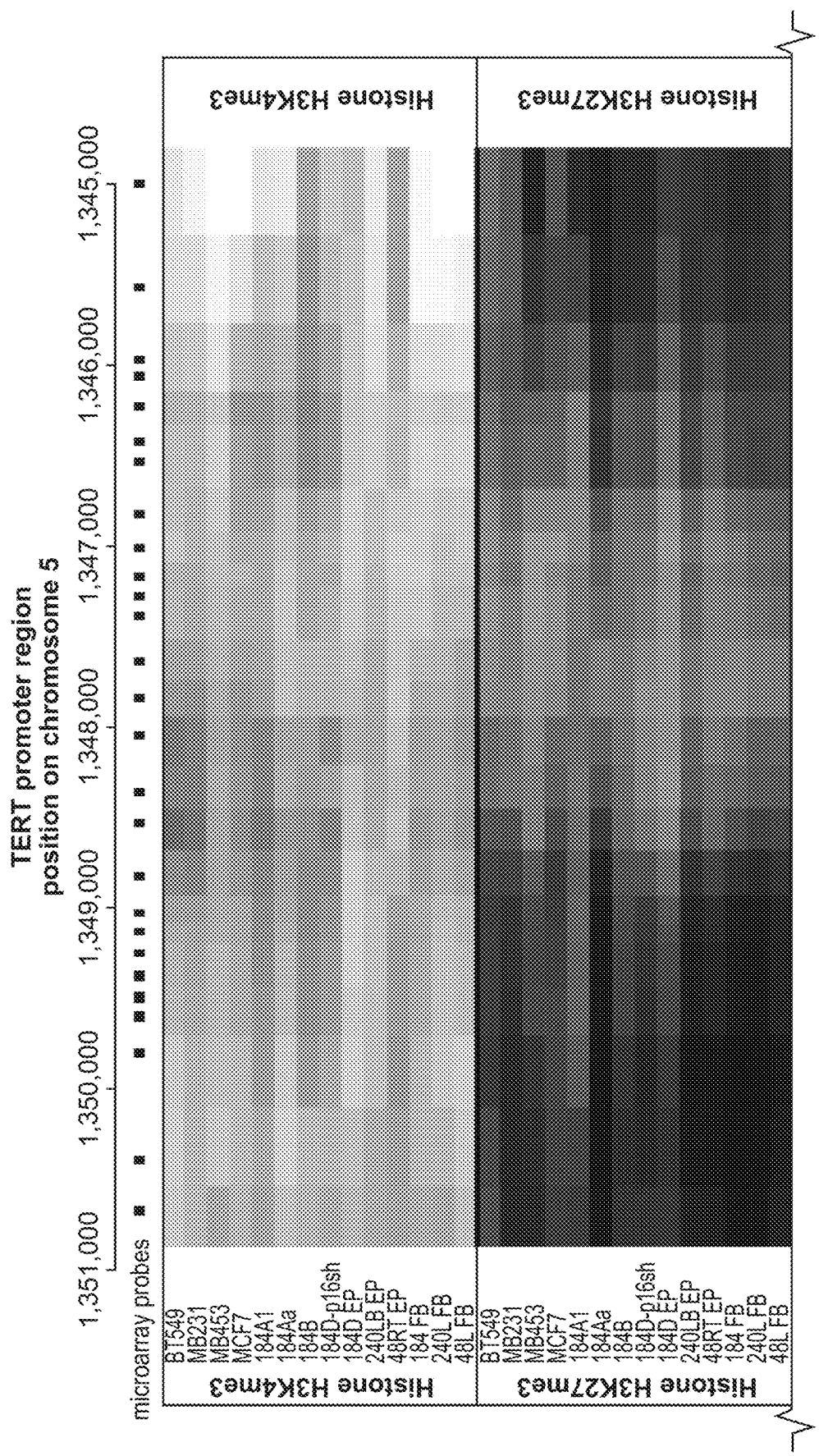
FIG. 13A-13C. Epigenetic analysis of the hTERT gene promoter.
Figure 13A:
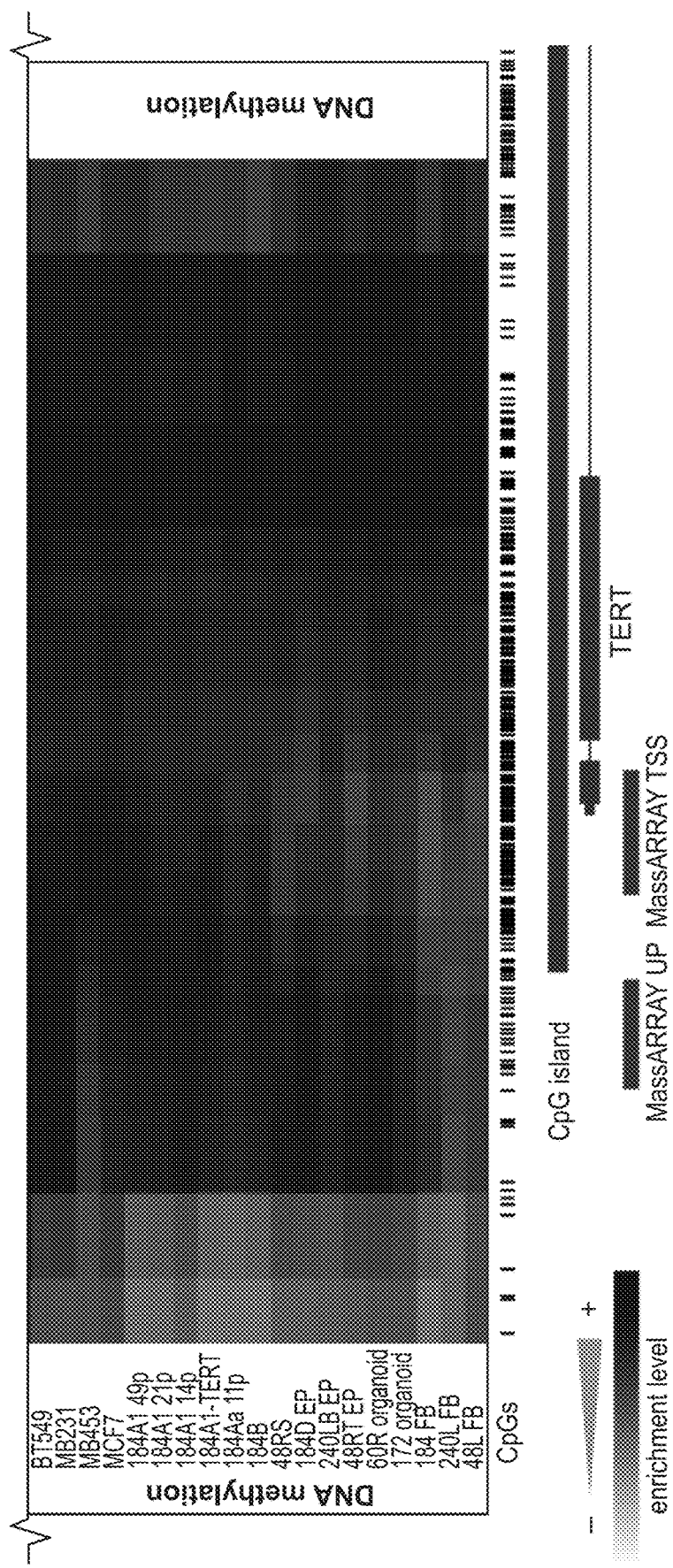
Figure 13C:
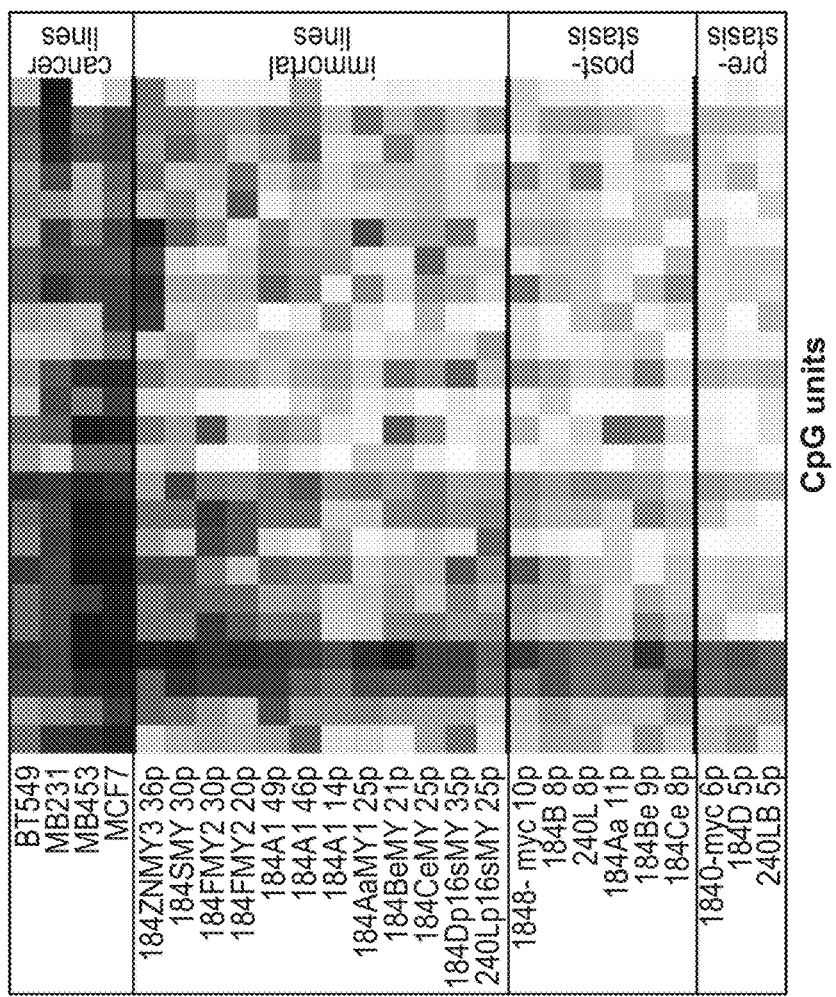
Figure 13B:
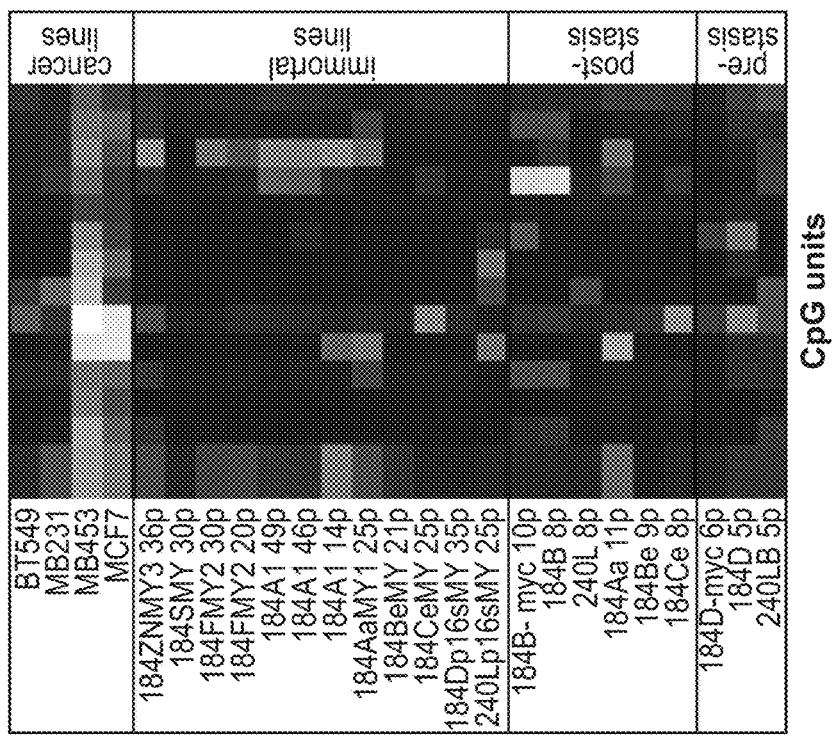
Figure 15E:
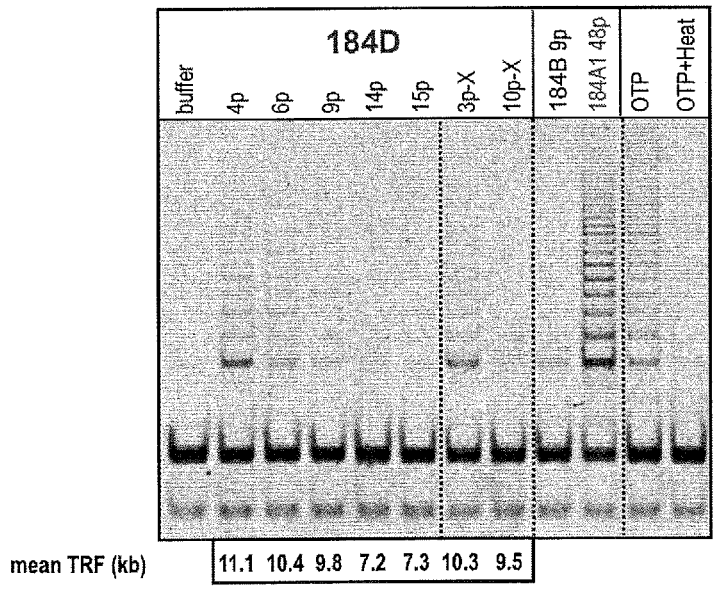

The above data showed that c-MYC can induce telomerase activity and immortalization in p16(−) BaP and p16sh post-stasis, but not post-selection post-stasis HMEC. One possible basis for this difference could be distinct hTERT chromatin states that affect accessibility of c-MYC, an hTERT transactivator. To evaluate this possibility and to gain better understand of HMEC telomerase regulation, the hTERT gene locus was examined for DNA methylation and permissive (H3K4me3) or repressive (H3K27me3) histone modifications using 5-methylcytosine and chromatin immunoprecipitations (ChIP) coupled to custom tiling microarray hybridization. Post-stasis BaP, post-selection, and p16sh cultures were examined along with other HMEC with different levels of TRAP activity, ranging from normal pre-stasis 184D (low activity, FIGS. 6A, 15E), isogenic 184 mammary fibroblasts (no activity, not shown), immortal 184A1 (FIG. 15E), and several breast tumor lines. The DNA methylation microarray results for the ~6 kb region that brackets the hTERT transcriptional start site are shown in FIG. 13A, lower panel. The TERT locus was extensively methylated in all samples analyzed, with no differences detected or correlated to the level of basal or MYC-inducible TRAP activity. To increase resolution and sensitivity of the DNA methylation analysis, two regions were analyzed in greater detail using MassARRAY (FIGS. 13B, 13C). One region that extended from 400 bp upstream to 200 bp downstream of the transcription start site (TSS) was unmethylated in the pre-stasis, post-stasis, and in vitro immortalized HMEC assayed, but partially methylated in some breast cancer cell lines. A second region located 850 to 1400 bp upstream of the TSS was extensively DNA methylated in all HMEC cultures, with lower levels in two of the four cancer cell lines. Therefore, there was no obvious correlation between DNA methylation state and TRAP activity among the cell types analyzed.

Figure 17:
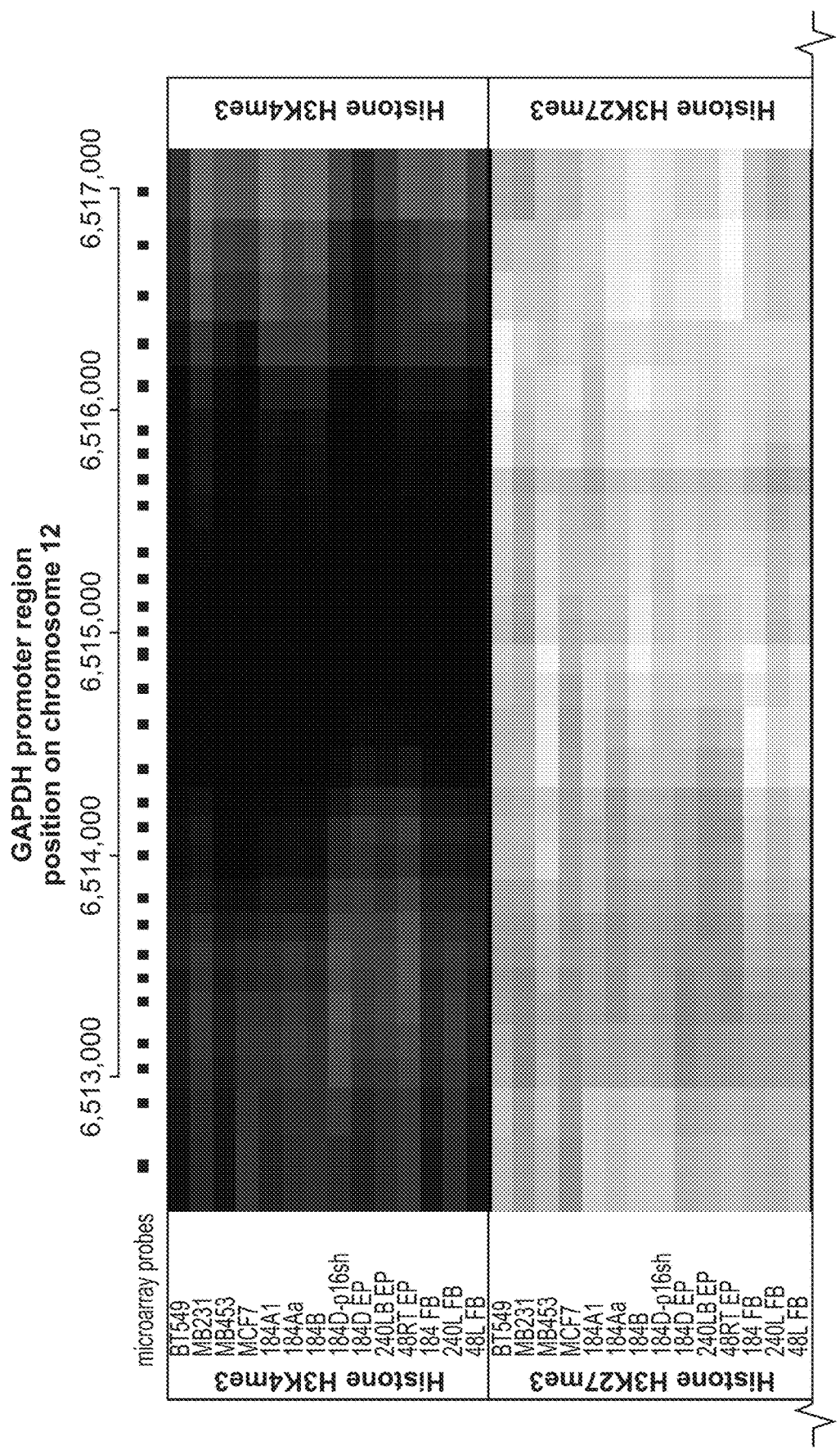
FIG. 17: Epigenetic marks at the actively expressed GAPDH gene. The tiling microarray data are displayed as a heatmap, with blue indicating high enrichment of particular epigenetic mark and yellow indicating no enrichment. Upper and middle sections of the heatmap show permissive H3K4me3 and repressive H3K27me3 histone marks, respectively; the bottom section shows DNA methylation data. The small black rectangles above the heatmap indicate positions of individual microarray probes. The vertical bars below the heatmap indicate positions of individual CpG dinucleotides. The CpG island is marked in green. The GAPDH gene structure is in blue. The genomic coordinates are hg18. There is strong enrichment for permissive H3K4me3 mark, no enrichment for the repressive H3K27me3 mark, and only very little enrichment for DNA methylation, consistent with active transcription of this housekeeping gene.
Figure 17:
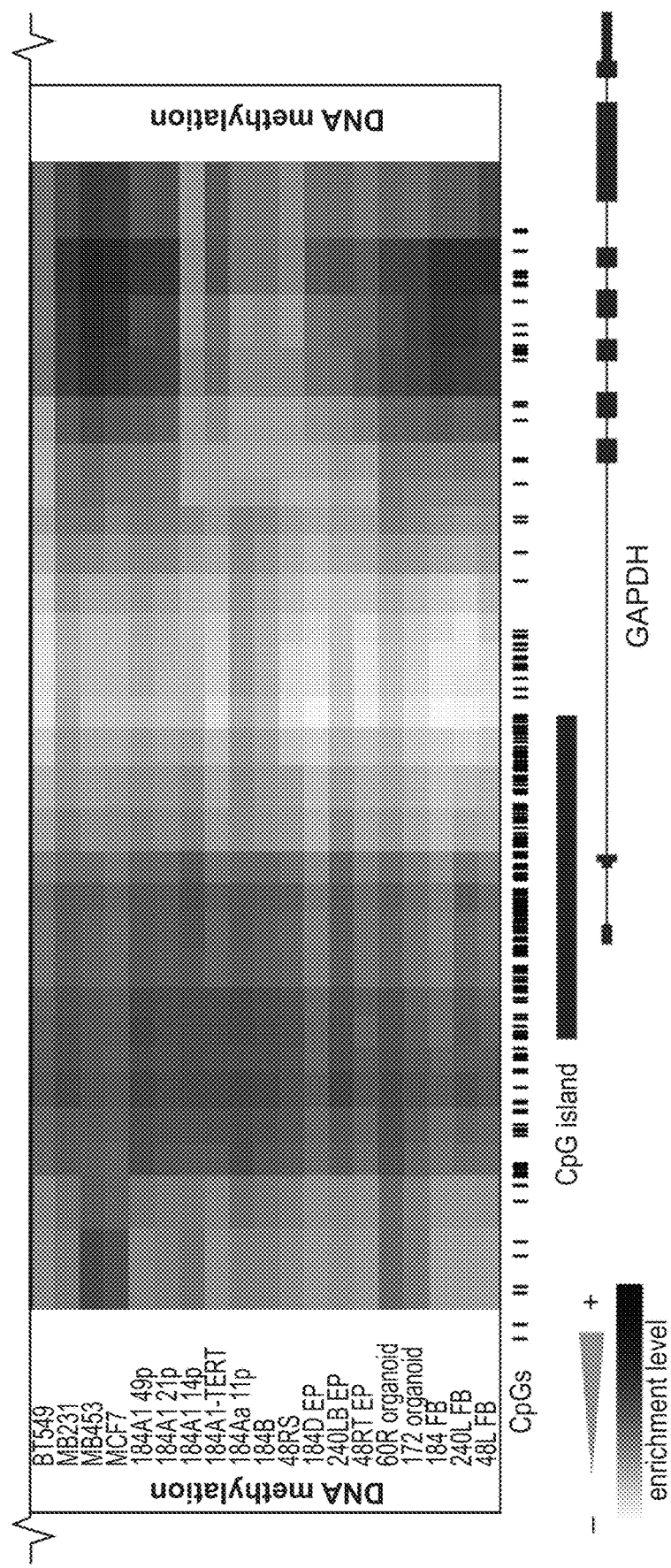

The unmethylated region immediately surrounding the TSS of the hTERT gene suggests a state permissive to transcription, so the absence of TRAP activity in some of these cultures might be due to other epigenetic marks. Using ChIP linked microarray, we analyzed the HMEC for two histone modifications at the hTERT gene region— H3K27me3, a polycomb-mediated repressive modification[28], and H3K4me3, a permissive modification present on all active and even some inactive promoters[29]. FIG. 13A (middle panel) shows that all the cultures have repressive H3K27me3 near the hTERT promoter, with no detectable correlation to TRAP activity. Surprisingly, the permissive H3K4me3 mark was not detected in the hTERT promoter region in any of the analyzed samples (FIG. 13A, top panel), including the in vitro immortalized and cancer lines, known to possess sufficient telomerase activity to maintain stable telomeres. The genomic region displayed in FIG. 13 includes the area occupied by H3K4me3 in TERT-expressing human embryonic stem cells according to the online data found at the Human Methylome page in the Neomorph website at the Salk Institute and we detected the permissive H3K4me3 at the GAPDH promoter (FIG. 17) and other active genes covered by the microarray.

Overall, the data show that the epigenetic states of the hTERT locus in the analyzed HMEC samples, with respect to DNA methylation, H3K4me3, and H3K27me3, are indistinguishable from one another and therefore do not appear to play a role in the differential response of post-stasis types to c-MYC transduction.

Characterization of Immortally Transformed HMEC Lines

The newly developed lines were characterized for lineage markers by FACS, immunofluorescence, and/or gene expression, and for AIG. Most of the lines did not display the malignancy-associated property of AIG (FIG. 1B); the one exception, 184FMY2, has other properties associated with more aggressive breast cancer cells (see below).

Figure 14B:
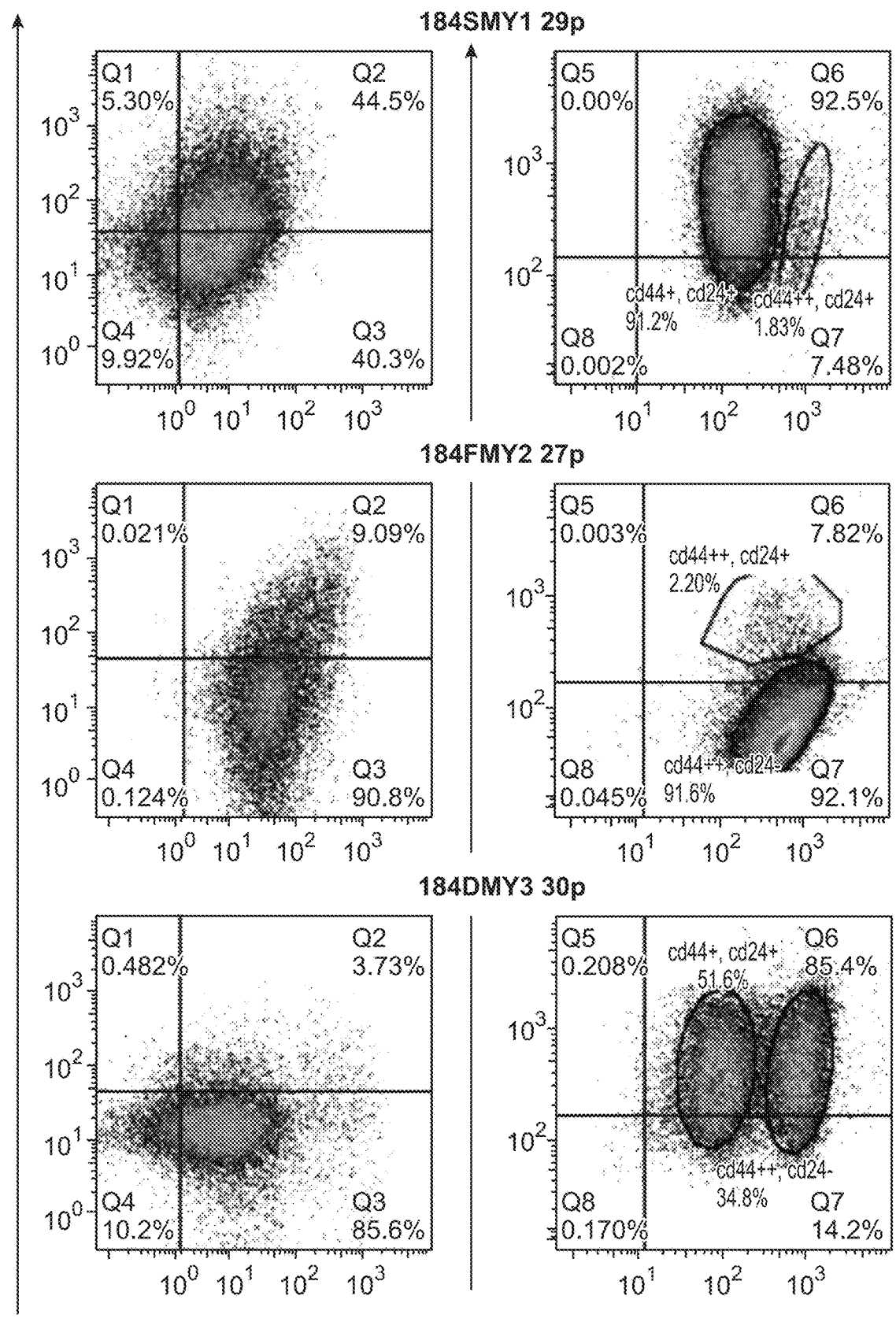
Figure 14B:
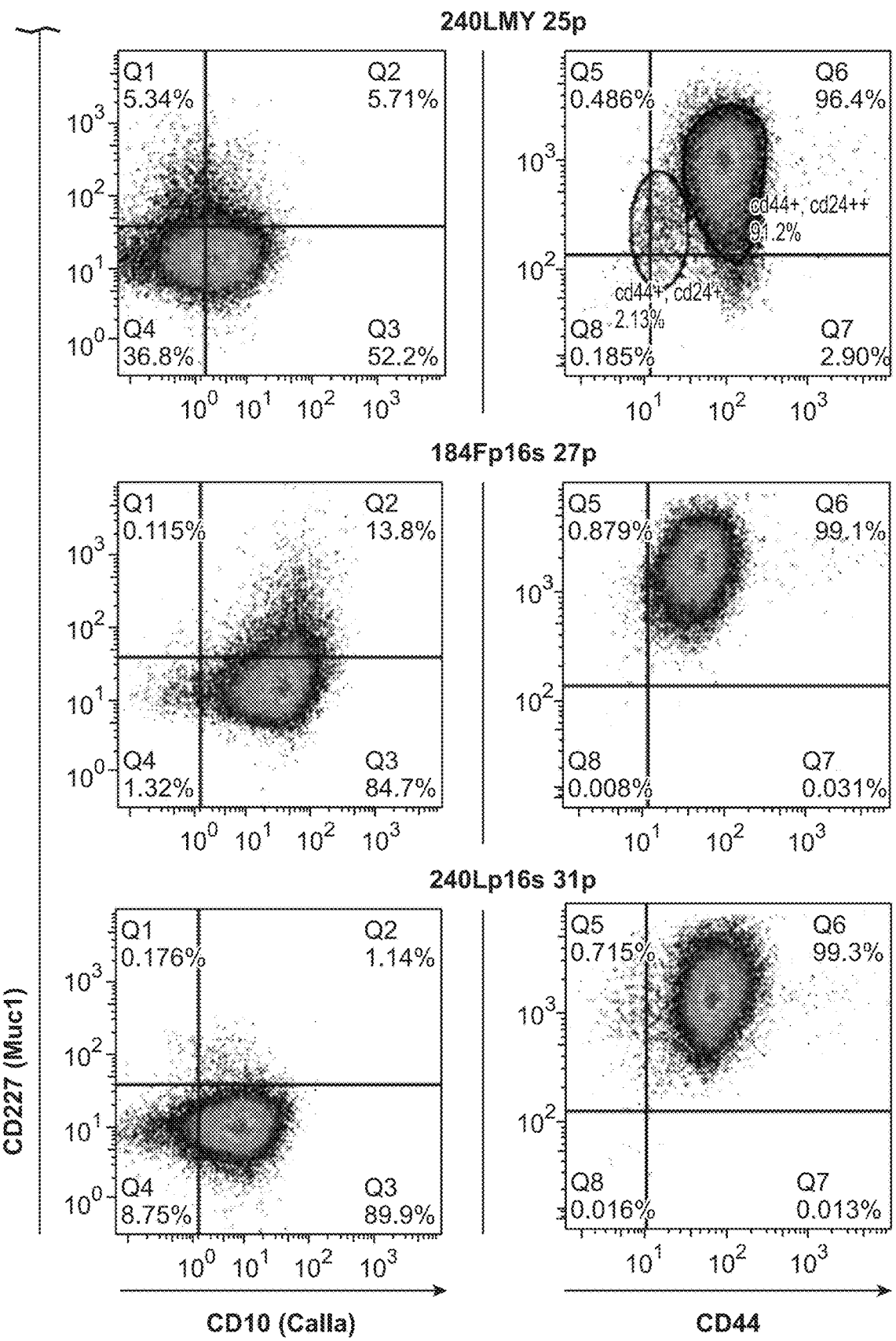
Figure 14C:
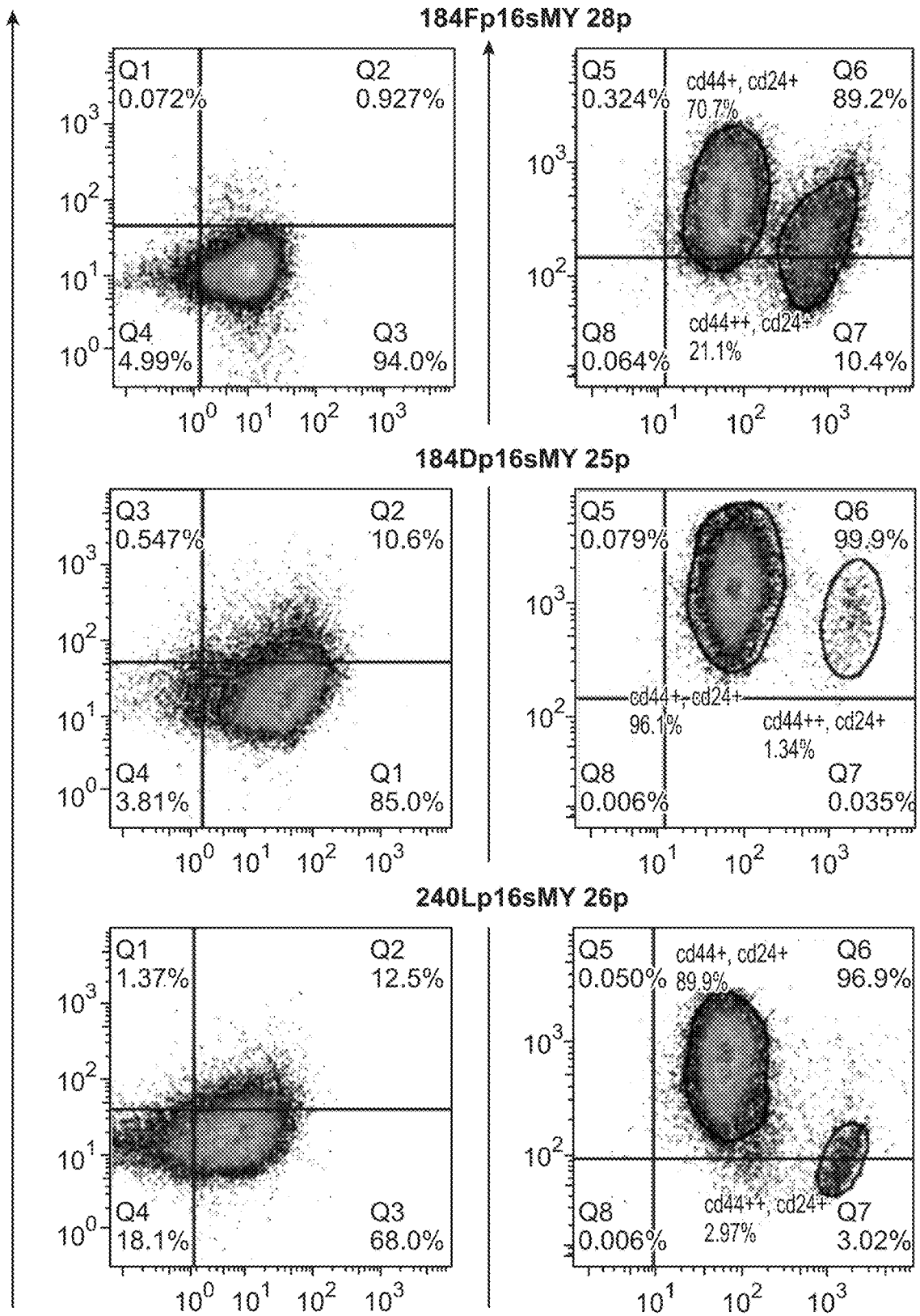
Figure 14C:
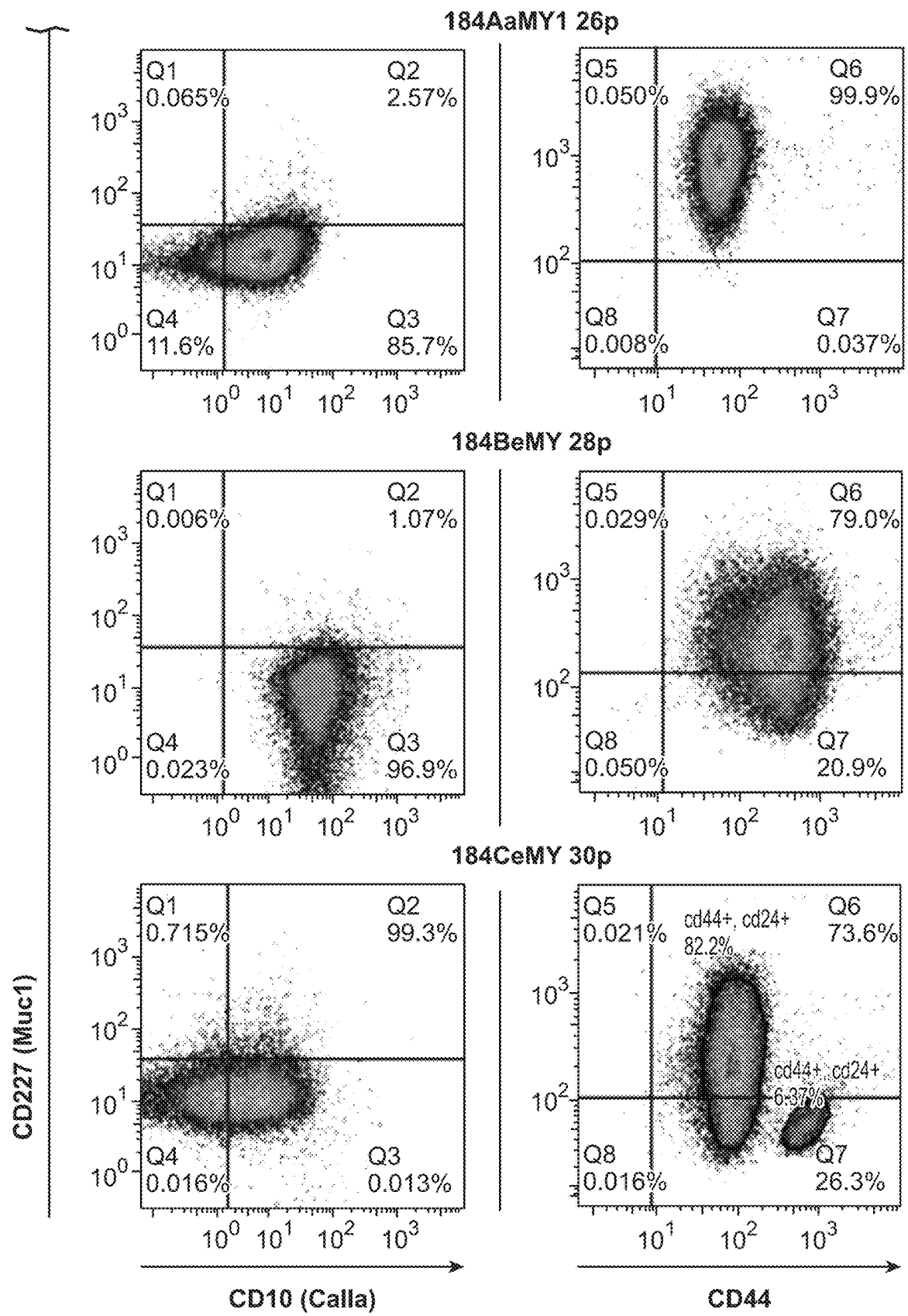

FACS analyses using the cell surface markers CD227 (Muc-1) and CD10 (Calla) can distinguish CD227+/CD10-luminal from CD227−/CD10+ myoepithelial lineages in normal pre-stasis HMEC (FIG. 14A). While normal pre-stasis 240L HMEC exhibit distinct luminal and myoepithelial populations, all the cell lines from specimens 184 and specimen 240L immortalized with p16sh and c-MYC exhibited a predominantly basal/myoepithelial-like phenotype, showing expression of CD10, along with minor to significant expression of CD227. In contrast, lines immortalized with cyclin D1 had increased CD227 expression (FIG. 14)

Antibodies recognizing the surface antigens CD44 and CD24 have been widely used in the putative identification of carcinoma cells with tumor-initiating properties[30,31]. Normal pre-stasis 240L HMEC are predominantly $CD44^{hi}$/ $CD24^{hi}$, with a small $CD44^{lo}$/$CD24^{hi}$ subpopulation. Almost all the lines exhibited co-expression of CD44 and CD24 at varying levels in all cells, but some had separate subpopulations with increased CD44 and decreased CD24, e.g., 184CeMY and 240Lp16sMY. Interestingly, the 184FMY2 cell line with AIG exhibited a very prominent $CD44^{hi}$/ $CD24^{low}$ population and evidence of EMT (Vrba, Garbe, Stampfer, Futscher unpublished), but no tumor-forming ability when injected subcutaneously in immune-compromised mice (data not shown).

Figure 12E:
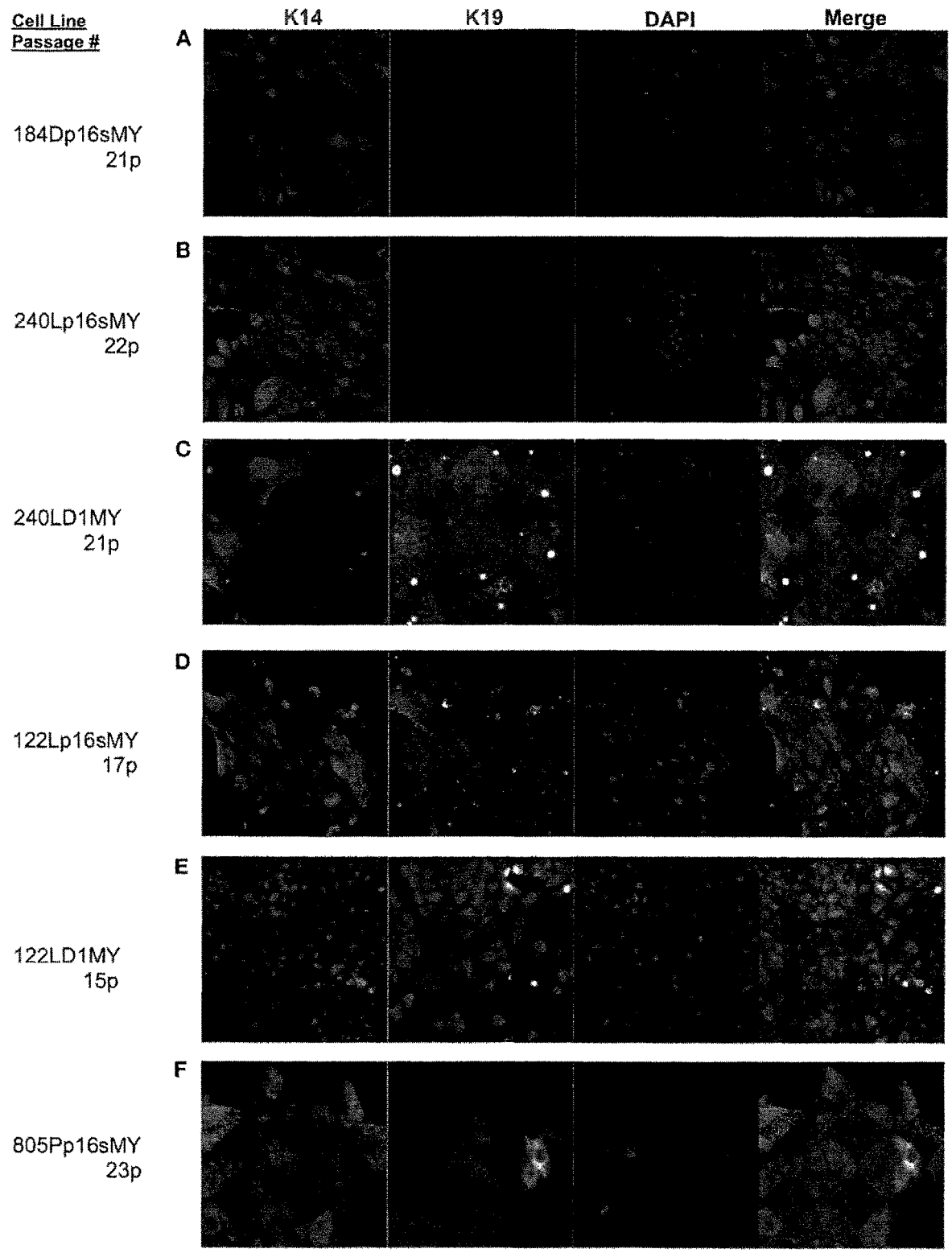
FIG. 12E. Lineage-specific keratin protein expression in non-malignant immortal HMEC on 2-D culture substrata. Representative immunofluorescence images showing keratin (K)14 (red) and K19 (green) expression in (Panel A) 184Dp16sMY, (Panel B) 240Lp16sMY, (Panel C) 240LD1MY, (Panel D) 122Lp16sMY, (Panel E) 122LD1MY, and (Panel F) 805Pp16sMY. Nuclei appear blue, bar represents 50 um. Lines derived from older women or using cyclin D1 to bypass stasis exhibit markers of a luminal phenotype.
Figure 19:
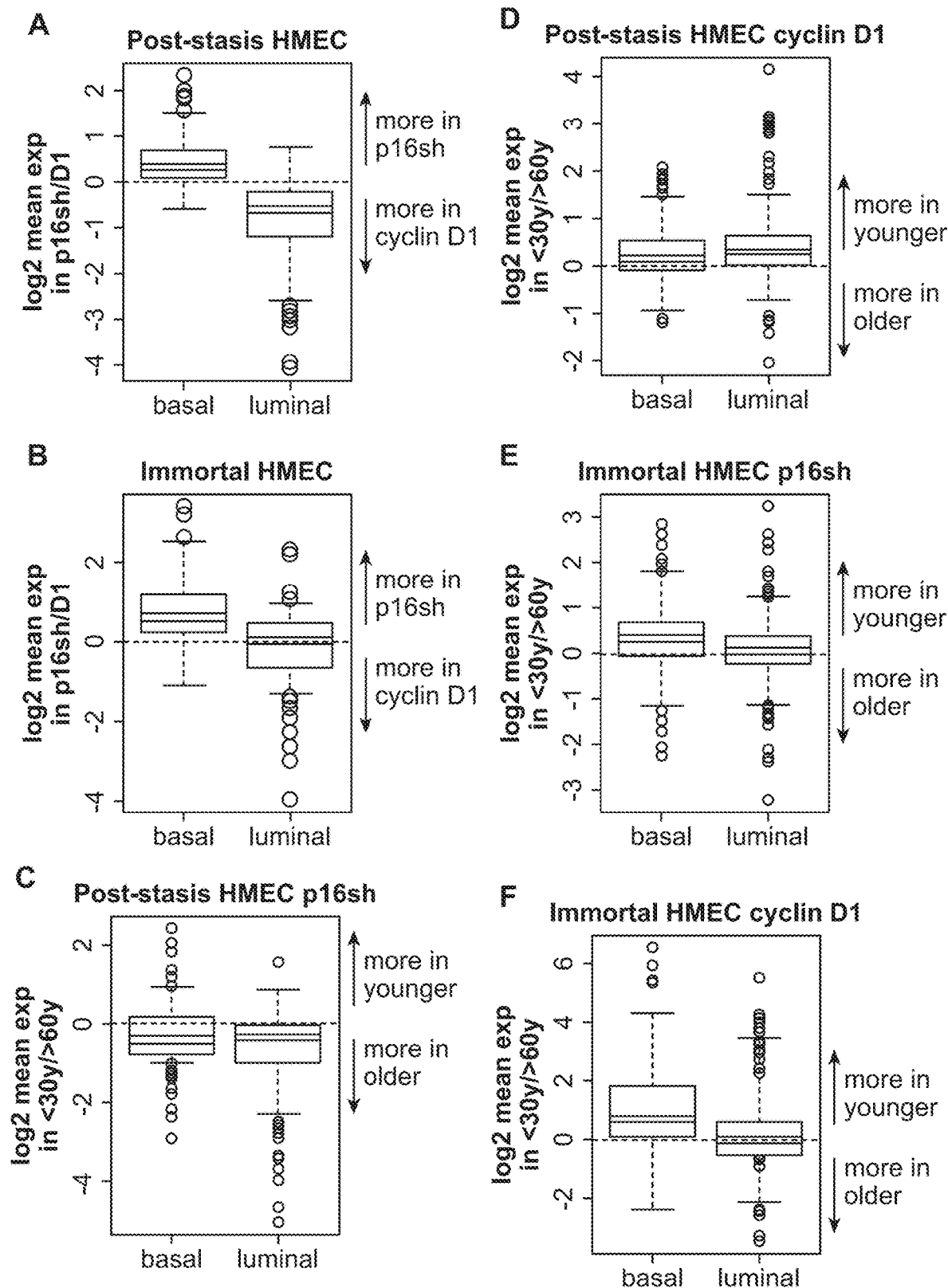
FIG. 19, Panels A-F: Lineage-specific gene expression. Boxplots showing enrichment of relative expression of 302 basal specific and 337 luminal specific transcripts in p16sh vs. D1 post-stasis HMEC (Panel A), and in p16sMY vs. D1MY immortal HMEC (Panel B). Boxplots showing enrichment of relative expression of luminal and basal specific transcripts in young vs. old donors in p16sh (Panel C) and D1 cells (Panel D) in post-stasis HMEC and in p16sh (Panel E) and D1 (Panel F) cells in immortal HMEC.
Figure 20:
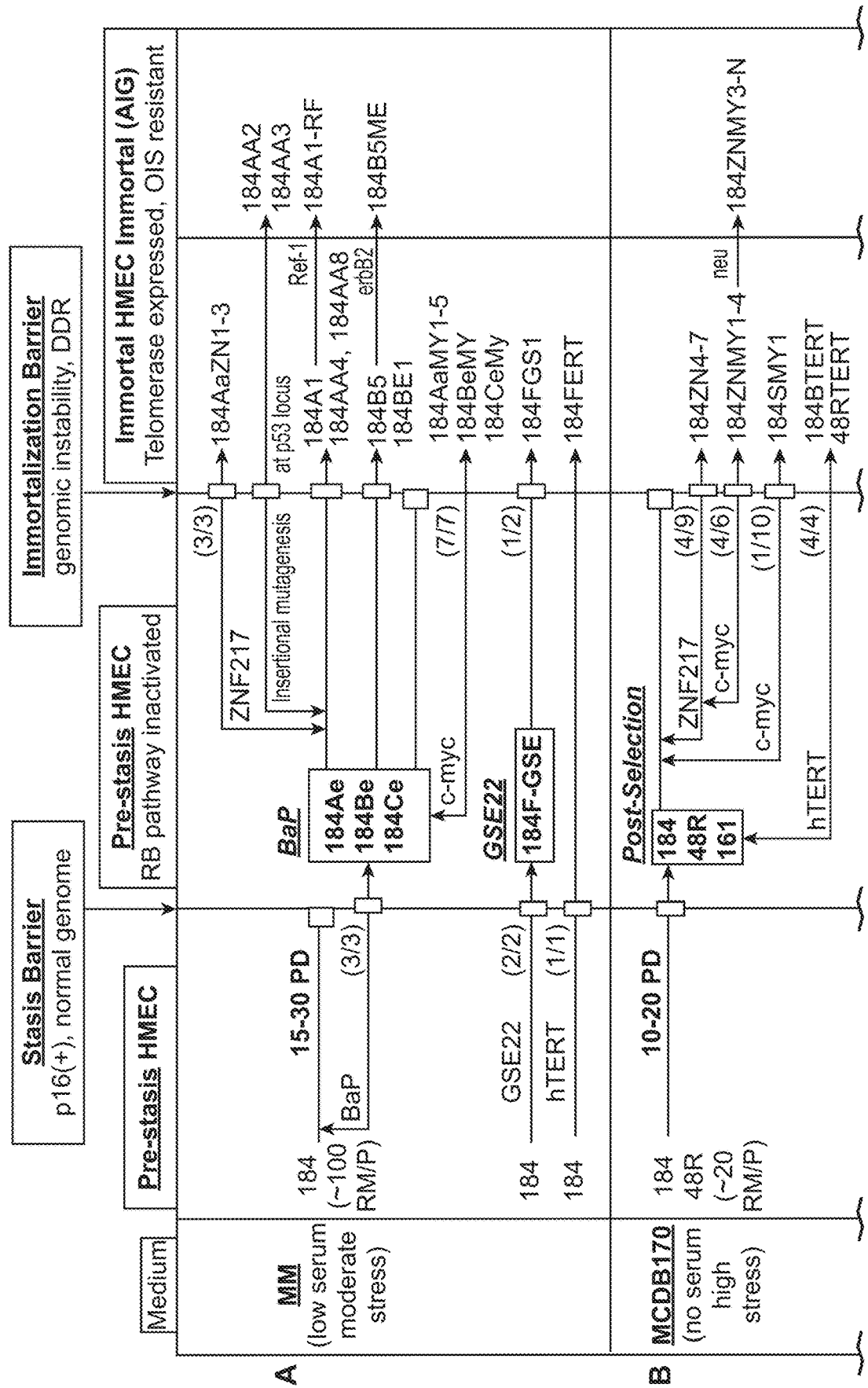
FIG. 20, Panels A-C: In vitro model system of step-wise transformation of normal finite HMEC through bypassing or overcoming senescence barriers by multiple pathways and molecular errors. Normal HMEC were grown using different culture conditions (panels A, B, C below) and exposed to pathologically relevant oncogenic agents, as well as hTERT (telomerase reactivation during in vivo carcinogenesis is not caused by introduction of ectopic hTERT). Both rare clonal and efficient non-clonal immortalization was achieved, dependent upon culture conditions and agents used. Different pathways to transformation generated lines heterogeneous for many properties (lineage markers, genomic stability, gene expression, epigenetic alterations, malignancy- and EMT-associated markers). Molecular properties diverged at the earliest stage in progression (bypassing stasis).
Figure 20:
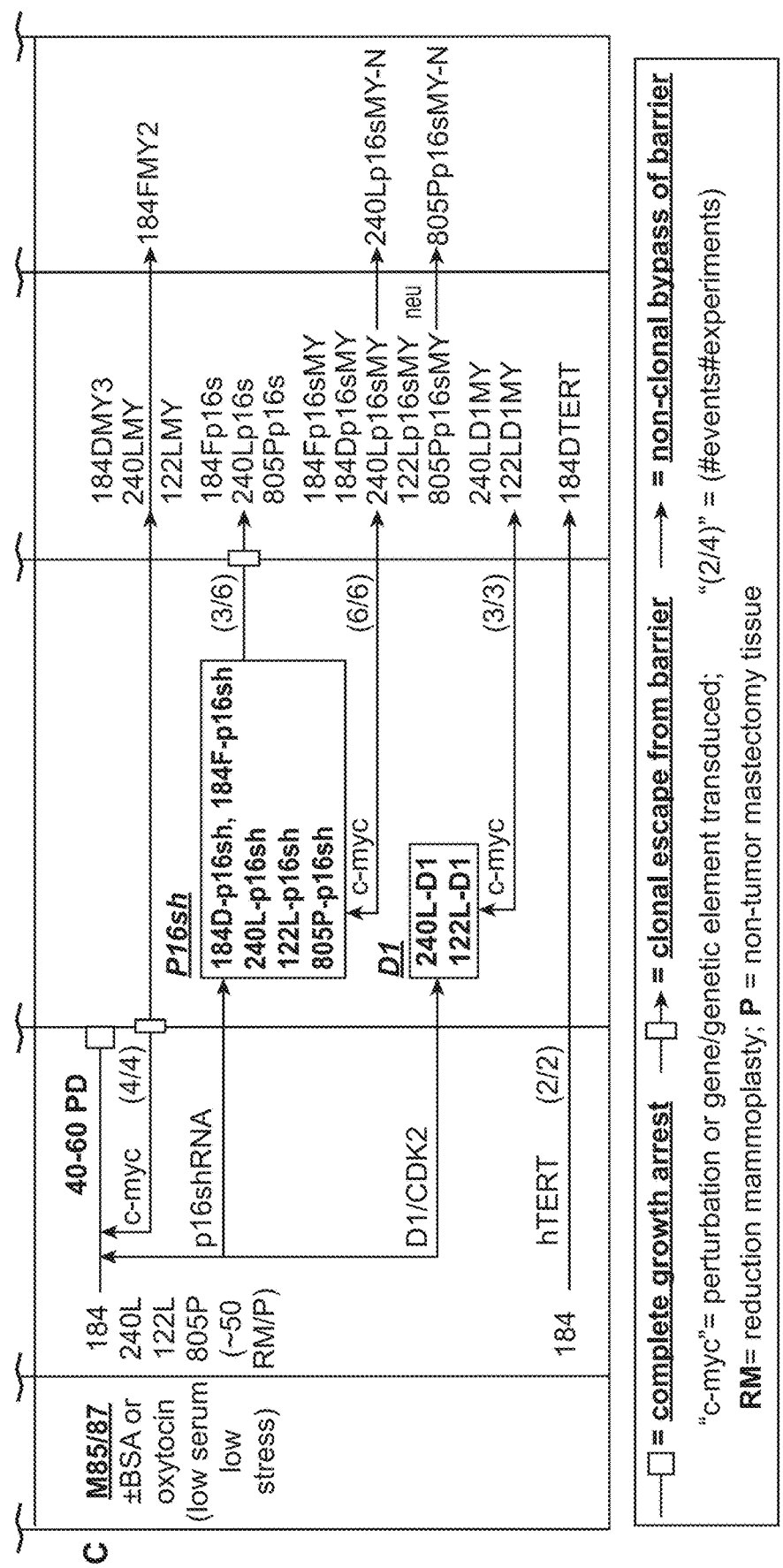
Figure 21:
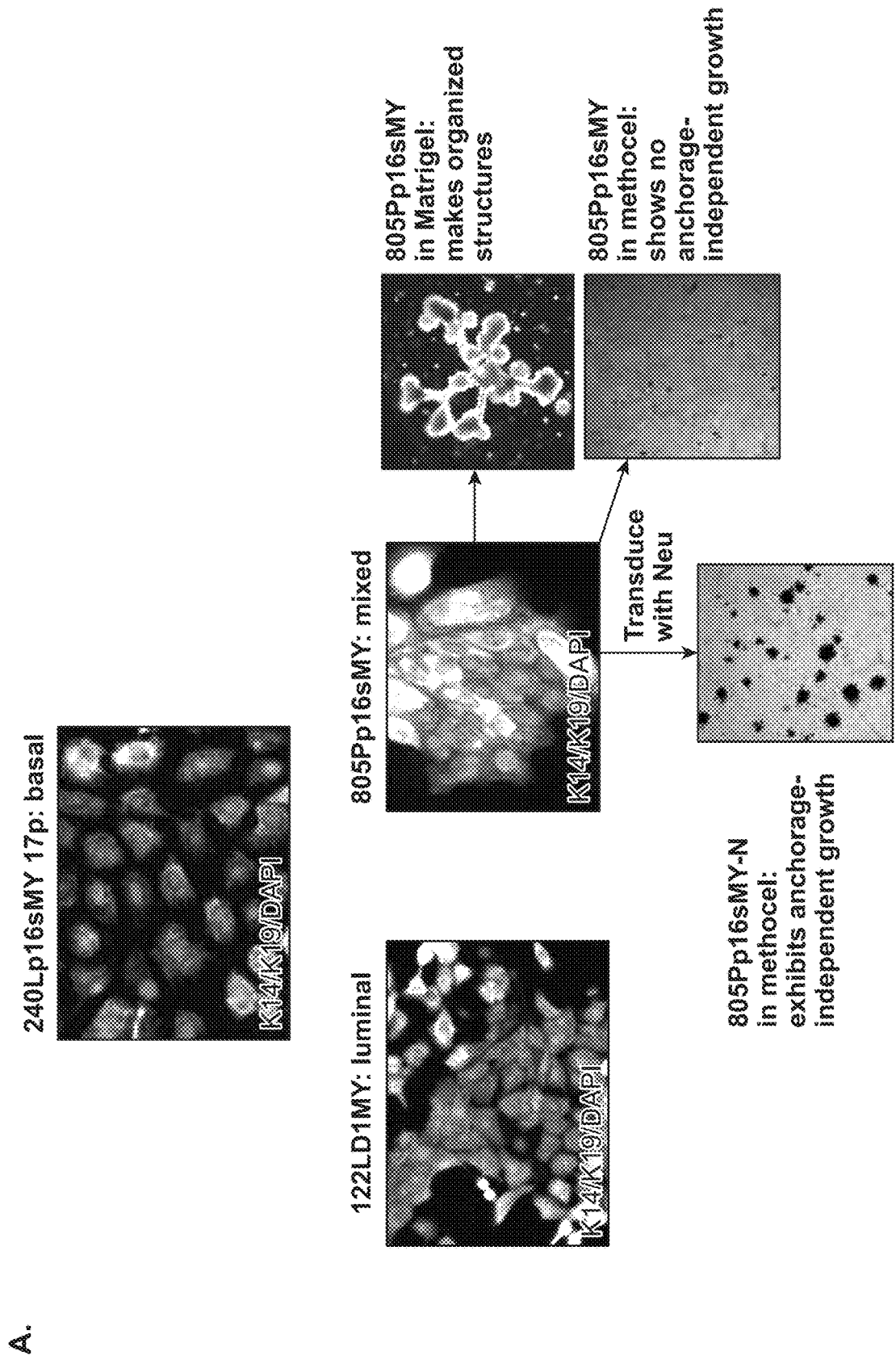
FIG. 21: Immortalized lines express diverse phenotypes. Transduction of oncogenes to non-malignant immortal lines confers malignancy-associated properties; in finite cells those oncogenes induce OIS. Phenotypes ranged from basal to luminal, dependent upon specimen, oncogenic agents and random errors. Some lines expressed EMT-associated properties; most lines showed functional p53. Panel A: Immortalized lines have varying phenotypes: expression of basal and luminal keratins. Transduced Neu confers AIG.

Comparison of lineage-associated gene expression and expression of lineage-associated proteins K14 (basal associated) and K19 (luminal associated) (FIGS. 12, 19) showed that in general, the immortalized lines derived from young reduction mammoplasty specimens using p16sh and c-MYC displayed basal-like phenotypes compared to the heterogeneous composition of their normal pre-stasis populations. Lines from both young and older specimens using the D1/cdk2 construct displayed more luminal-like phenotypes, and lines from older specimens using p16sh and c-MYC displayed both basal and luminal markers. Changes in lineage expression were apparent at the finite post-stasis stage (FIGS. 12, 14, 19). These data suggest that age and the means of bypassing stasis are key in establishing luminal-like or basal-like gene expression patterns, and occur early in progression.

Figure 18A:
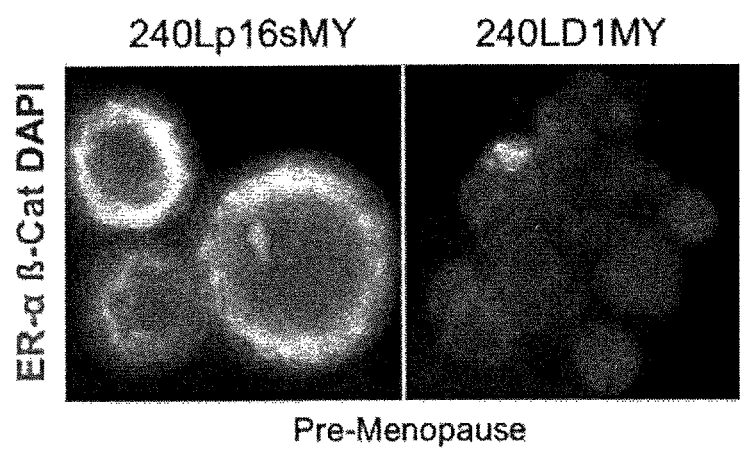
FIGS. 18A and 18B: Estrogen receptor and beta-catenin expression in 3-D. Representative immunofluorescence images ERa (red) and B-catenin (green) expression in (FIG. 18A) 240Lp16sMY and 240LD1MY, and (FIG. 18B) 122Lp16sMY and 122LD1MY. Nuclei appear blue, bar represents 50 um.
Figure 18B:
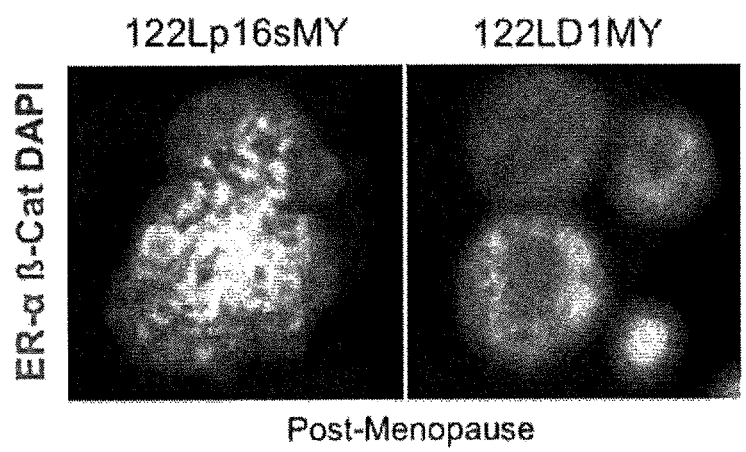

To further assess the differential effects of age and of method of stasis bypass, expression of the estrogen receptor alpha (ERa) protein was evaluated in the p16sMY and D1MY cell lines derived from the young strain 240L and the older strain 122L. ERa is expressed by a subset of luminal cells in the normal mammary gland, and is used to categorize the luminal subtypes of breast cancers. ERa was not detected in either the p16sMY or D1MY line derived from 240L (FIG. 18A), but it was richly expressed in both 122L-derived lines independent of the method used to bypass stasis (FIG. 18B). Altogether these data indicate that these non-clonal lines are heterogeneous, containing a mixture of lineages.

Discussion

Immortalization of normal cultured HMEC using agents associated with breast cancer pathogenesis in vivo has been difficult to achieve. We report here that reproducible non-clonal immortalization was attained by targeting two tumor suppressive senescence barriers, stasis and replicative senescence, and that resultant immortalized lines exhibit normal karyotypes at early passage. Our prior studies have indicated that stasis is enforced in cultured HMEC by elevated p16 levels maintaining RB in an active state. Unlike some other human epithelial cell types, e.g., keratinocytes[32], p53-dependent p21 is not upregulated in cultured HMEC at stasis 10, 12, 13; consequently, transduction of shRNA to p16 can be sufficient to bypass stasis. Overcoming the telomere dysfunction barrier at replicative senescence requires, at minimum, sufficient levels of telomerase activity to maintain stable telomere lengths. Transduction of c-MYC could induce telomerase activity and immortalization in some, but not all types of p16(−) post-stasis HMEC. These results demonstrate that bypassing these two barriers is sufficient to transform normal finite HMEC to immortality; genomic instability and gross genomic errors are not required. The data also validate our model of the functionally and molecularly distinct tumor suppressive senescence barriers encountered by cultured HMEC: stasis, a stress-associated arrest independent of telomere length and extent of replication, and replicative senescence due to ongoing replication in the absence of sufficient telomerase producing critically short telomeres and telomere dysfunction[6,10].

Expression of sufficient telomerase activity is crucial for human carcinoma progression. Almost all human breast cancer cell lines and tissues have detectable telomerase[33,34]; the ALT method for telomere maintenance is very rare[35]. The presence of short telomeres and genomic instability in most DCIS, as well as in pre-malignant lesions from other human organ systems, indicates that these lesions did not develop from cells expressing sufficient telomerase for telomere maintenance[4,5,36,37]. While malignancy requires immortality to support ongoing tumor cell proliferation, telomerase can also provide significant additional malignancy-promoting properties[38]. Telomerase reactivation has been associated with gaining resistance to OIS[11,15 39], and expression of hTERT can confer resistance to TGF-β growth inhibition[22] and affect other signaling pathways[38,40]. Given the importance of telomerase and immortalization for human carcinogenesis, it is surprising that so little is known about the regulation of hTERT as normal cells transform to cancer. The lack of appropriate experimentally tractable model systems has contributed to this knowledge gap. Unlike humans, small short-lived animals such as mice do not exert stringent repression of telomerase activity in adult cells, which can spontaneously immortalize in culture[2,3]. Comparison of the human and mouse TERT gene shows significant differences in regulatory regions[41]. The importance of telomerase in murine carcinogenesis has been demonstrated using animals engineered to lack telomerase activity[42], however such models do not address the mechanisms that allow endogenous hTERT to become reactivated during human carcinogenesis. There has also been a lack of human epithelial cell systems that model immortalization as it might occur during in vivo tumorigenesis. The use of ectopic hTERT to achieve immortalization precludes study of the factors that regulate endogenous hTERT in vivo, while viral oncogenes such as HPVE6E7 or SV40T are not etiologic agents for most human carcinomas, including breast, and have many characterized and uncharacterized effects.

We have employed reduction mammoplasty-derived primary HMEC grown under different culture conditions and exposed to a number of oncogenic agents, to generate cell types that may represent the different stages and heterogeneity of in vivo malignant progression.[6-9, 11] Prior studies revealed divergence in transformation pathways at the earliest stage, becoming post-stasis. Post-selection post-stasis HMEC exhibited ~200 DMR, most of which are also found in breast cancer cells, compared to ~10 in BaP and ~5 in p16sh post-stasis HMEC[18]. Of note, it has been suggested that post-selection post-stasis HMEC (also referred to as vHMEC[43], and sold commercially as "normal" primary HMEC (Lonza CC-2551; Life Technologies A10565)) may be on a pathway to metaplastic cancer[44]. Here we show an additional difference among post-stasis types: the inability of post-stasis post-selection HMEC to become immortalized by transduced c-MYC. While the molecular processes underlying this difference remain unknown, we note an association with prior exposure to culture stress. Post-selection HMEC overcame stasis following growth in medium that rapidly induces p16, whereas p16sh and D1 post-stasis HMEC bypassed stasis prior to p16 induction. The distinct properties of the post-selection HMEC may result from their prior experience of p16-inducing stresses. Current studies are addressing the hypothesis that mechanical stressors may influence telomerase expression. Functionally, our results suggest that neither post-selection HMEC, nor pre-stasis HMEC cultured in MCDB170-type media, would be suitable substrates for the immortalization protocol presented here.

The molecular phenotype of cancer cells likely varies depending upon initial target cell as well as the specific errors that promote transformation. Progenitor cell types have been suggested to be the initial target in some situations[45-47]. Our M87A/85 media support proliferation of pre-stasis HMEC with progenitor lineage markers, and allow robust proliferation prior to p16 upregulation[10,48].

Such lower stress/p16-inducing conditions may be reflective of early stage carcinogenesis in vivo, if unstressed progenitor cells are initial targets.

Our results support the hypothesis that genomic errors are needed to bypass or overcome tumor suppressive barriers, but instability and aneuploidy per se may not be required for transformation[6,10]. While all our clonally derived lines exhibit multiple genomic alterations[1,8,9], non-clonal lines without gross genomic errors could be generated by directly targeting the two main barriers to immortality, stasis and replicative senescence. Most human carcinomas contain many genomic changes, however, only a small number of these are estimated to play a driving role in carcinogenesis[49]. Several hypotheses have addressed the causes of genomic instability and aneuploidy in carcinomas, including mutator phenotype[50], DNA damage[51], and altered genomic copy number models[52,53]. We, and others, have proposed that the inherent genomic instability during telomere dysfunction at replicative senescence may be responsible for initiating most of the genomic errors seen in primary breast cancers[4,6,10,54,55]. This instability will render most cells non-proliferative or dead, but rare cells that generate errors allowing telomerase reactivation may immortalize, carrying with them all the other errors accumulated to that point. Consequently, genomic instability in pre-malignant cells may be the source of many of the "passenger" mutations present in carcinomas, as well as of "driver" mutations that influence prognosis. If bridge-fusion-breakage cycles have begun, immortalized cells will maintain some ongoing instability[9]. This hypothesis is consistent with DCIS cells possessing short telomeres, genomic instability, and many breast cancer-associated properties, including specific genomic errors and aggressiveness[56-59], as well as detection of telomerase activity in some DCIS tissues. Further, our results suggest that once a cell acquires the errors that allow stasis bypass, and then maintains proliferation to telomere dysfunction, no external agents may be needed to support rare progression to immortality. Although gross genomic changes were not required for immortalization of post-stasis HMEC by transduced c-MYC, epigenetic changes might be needed: changes have been observed associated with immortalization, even in non-clonally immortalized lines with no gross karyotypic abnormalities ([18] and unpublished). Our genomically normal non-clonal immortalized lines lack malignancy-associated properties; however, we and others have seen that these OIS-resistant populations can be readily further transformed to AIG and/or tumorigenicity by transduction of individual oncogenes[1,11,60] Genomic analysis of non-clonal lines malignantly transformed at early passage will be needed to determine whether a malignant phenotype can be achieved without gross genomic errors.

Our DNA methylation and histone modification analysis of the TERT locus provides an overview of the hTERT epigenetic state in normal to malignant cells, with varying expression of telomerase activity, from one organ system. We did not find any changes in DNA methylation or histone modification state that could explain the distinct responses to transduced c-MYC by post-selection post-stasis HMEC compared to the BaP and p16sh post-stasis types. Overall, we did not find a correlation between DNA methylation or histone modification and TRAP activity in all the HMEC examined. Specifically, the CpG-rich region that immediately surrounds the TERT TSS is DNA unmethylated in pre-stasis, post-stasis, and TRAP(+) immortal HMEC cultures. These results using isogenic HMEC indicate that the lack of DNA methylation in this region may be permissive for, but is not by itself indicative of telomerase activity[61].

This DNA methylation state is similar to what is seen in TERT-expressing human embryonic stem cells (hESC) or induced pluripotent stem cells (Human methylome page in the Neomorph website for the Salk Institute). Outside of the TERT TSS region, the rest of the TERT promoter is densely DNA methylated in most of the examined HMEC, consistent with previous reports for human cancer cells[61,62], as is the large CpG island that extends from the promoter to approximately 5 kb into the gene itself, similar to hESC and iPSC (Human methylome page in the Neomorph website for the Salk Institute). Our histone modification analysis did not detect the H3K4me3 mark at the TERT promoter/TSS in HMEC with and without telomerase activity. The polycomb-specific H3K27me3 mark was detected both upstream and downstream of the TSS region, but similar to DNA methylation, the H3K27me3 levels decreased near the TSS. These results are in contrast to hESC cells, where the TERT promoter exists in a bivalent state, occupied by both H3K4me3 and H3K27me3 (Human methylome page in the Neomorph website for the Salk Institute). Altogether, these analyses highlight some unusual qualities of the hTERT locus, in addition to the absence of any obvious epigenetic regulation correlated with TRAP activity. The absence of permissive H3K4me3 mark and the presence of two distinct repressive epigenetic marks at the HMEC TERT promoter suggests it exists in a repressed or inactive chromatin state, regardless of TRAP activity or finite vs immortal status. This type of redundant chromatin repression may reflect human cells general need, as part of tumor suppression, to limit TERT induction to prevent sustained aberrant overexpression and cell immortalization. Further support of this possibility is the presence of very high DNA methylation levels in the unusually large CpG island at the 5'end of the hTERT gene, a structure usually associated with transcriptional repression and heterochromatic state. Additionally, since TERT expression is usually very low and dynamic, being predominant during S-phase, at a given moment promoters permissive for transcription may be present only in a small proportion of the cells, making it difficult to detect active chromatin.

The process of telomerase reactivation during human carcinogenesis may present a valuable target for clinical intervention. While breast cancers are known to be heterogeneous, both among and within a given tumor, the requirement for immortalization is common to almost all human carcinomas. Further, unlike the signaling pathways involved in cell growth and survival, there are no commonly used alternative pathways to telomerase reactivation during HMEC immortalization, thus decreasing the possibility for emergence of therapeutic resistance. However, development of potential therapeutics has been limited by the lack of information on the mechanisms underlying human epithelial cell immortalization, and by the absence of a significant immortalization barrier in murine carcinogenesis, precluding usage of murine models for testing pharmacologic interventions in immortalization. The reproducible immortalization of HMEC in the absence of "passenger" errors that is achievable with our system can facilitate further examination of the mechanisms involved in hTERT regulation during carcinogenesis. Better understanding of hTERT regulation may offer new clinical opportunities that involve not just targeting telomerase activity but the reactivation process itself.

Figure 22:
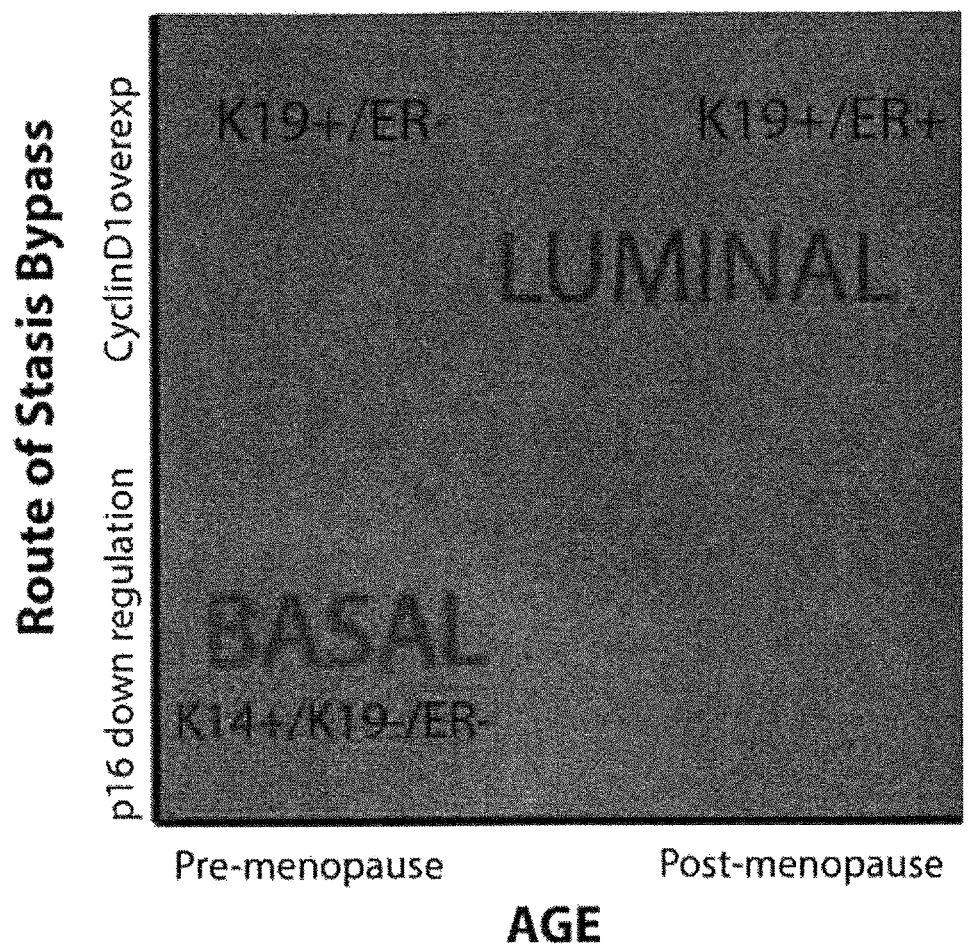
FIG. 22: Phase diagram summarizing our hypothesis of the impacts of chronological age and the means of bypassing stasis on the intrinsic subtype of immortal HMEC. The color red indicated basal-like subtypes, and green represents luminal-like subtypes.

Breast cancers have been categorized by lineage markers into intrinsic subtypes that differ in prognosis and response to treatment. The mechanisms responsible for determining subtype have not been clearly defined; cell of origin, specific oncogenic insults, and cellular microenvironment have been proposed to influence lineage expression in cancer cells. However, lineage specificity in immortal and malignantly transformed cells is neither exact nor obvious by comparison to the normal lineages in vivo. Every non-clonal cell line generated had some level of heterogeneity, with varying distributions of cells representing the luminal and myoepithelial lineages. Here we show that the relative luminal vs. basal phenotype of immortalized HMEC is influenced by both chronological age and the method of stasis bypass (FIG. 22). A comparison of HMEC from young (<30 years) vs. older (>60 years) women showed that increased age biased toward generation of immortalized lines with greater expression of luminal phenotypes. A comparison of immortalized lines generated by using either p16sh or cyclin D1/CDK2 to bypass stasis showed a bias toward a luminal phenotype when cyclin D1/CDK2 was utilized, independent of age.

A strength of our approach is that the outcome of the immortalization process can be evaluated in the absence of confounding gene mutations and gross genomic re-arrangements. Thus it is reasonable to assume a given targeted genetic change played a role in the final phenotypes of the cell lines that were generated. By comparison, the diverse collection of tumor-derived breast cancer cell lines available bear a large number of genetic and epigenetic changes, making it difficult to causally link specific changes to an intrinsic subtype, or indeed to the process of becoming immortal. Here we were able to control two variables, age and the method of bypassing stasis barrier, while holding other variables constant, such the use of c-MYC to transactivate telomerase to bypass replicative senescence. Our results implicate the earliest events in cancer progression—chronological age of the cell of origin and the molecular pathway used to bypass stasis—as key determinants of breast cancer subtype.

Material and Methods

Cell Culture.

Finite lifespan HMEC from specimens 184, 240L, 48R, and 122L were obtained from reduction mammoplasty tissue of women aged 21, 19, 16, and 66 respectively. Specimen 805P was obtained from non-tumor mastectomy tissue of a woman aged 91. Pre-stasis 184 (batch D), 240L (batch B), 48R (batch T), 122L, and 805P HMEC were grown in M87A supplemented with 0.5 ng/ml cholera toxin (CT), and 0.1 nM oxytocin (X) (Bachem); pre-stasis 184 (batch F) were grown in M85+CT, as described[10]. Post-selection post-stasis HMEC 184 (batch B, agonescence at ~passage (p) 15; batch S, agonescence at ~22p), and 48R batch S, agonescence at ~22p, as well as BaP post-stasis 184Aa, 184Be, and 184Ce HMEC (agonescence at ~16p, 10p, 15p respectively) were grown in serum-free MCDB170 medium (commercially available versions MEGM, Lonza, or M171, Life Technologies) plus supplements[19]. Total PD level was calculated as described in Garbe 2009_ENREF_9[10]. Anchorage-independent growth (AIG) was assayed as described[9] using 1.5% methylcellulose solution made up in M87A+CT+X. Details on the derivation and culture of these HMEC can be found at the HMEC website for LBNL (hmec.lbl.gov). Research was conducted under LBNL Human Subjects Committee IRB protocols 259H001 and 108H0041.

Retroviral Transduction. The p16 shRNA vector (MSCV) was obtained from Greg Hannon,[63].

The p16-containing construct was pLenti-p16-neo vector, plasmid 22260, Addgene. One of the p16 shRNA sequences used is ctgcccaacgcaccgaatagttacggtcgg (SEQ ID NO:3).

Four different c-MYC vectors were used: LXSN for 184B, 184S, 184Aa, 184F; pBabe-hygro (BH2) for 184Be, 184Ce, 184D, 240LB; LNCX2-MYC-ires-GFP for 48RS[60]; Myc:ER for 184S, 184B[64]. The hTERT vector pBabe-hygro-TERT was obtained from Bob Weinberg[65]. The c-MYC sequences used are shown in SEQ ID NOS:1 and 2. The construct used was the SPARQ™ Cumate Switch inducible lentivector Cat# QM800A-1 (System Biosciences, Mountain View, Calif.) where the c-MYC inserted at SalI and EcoR1 site.

Retroviral stocks were generated, supernatants collected in MCDB170 medium containing 0.1% bovine serum albumin or M87A medium, and infections performed as described in Stampfer M R, Garbe J, Nijjar T, Wigington D, Swisshelm K, Yaswen P. Loss of p53 function accelerates acquisition of telomerase activity in indefinite lifespan human mammary epithelial cell lines. Oncogene 2003; 22:5238-51, hereby incorporated by reference in its entirety.

TRAP Assays.

Telomerase activity assays employed the TRAPeze Telomerase detection kit (Millipore) using 0.2 µg of protein extract per reaction. Reaction products were separated on a 10% polyacrylamide gel and visualized using a Storm 860 imaging system (Molecular Dynamics).

DNA Isolation.

Genomic DNA was extracted using the DNeasy Blood and Tissue Kit (Qiagen) according to manufacturer protocol and quantified spectrophotometrically.

Comparative Genomic Hybridizations (CGH) and Karyology.

CGH was performed at the Genomics Shared Service of the Arizona Cancer Center using the Agilent human genome CGH microarray with 44,000 probes per array, and analyzed using Bioconductor in an R environment[66]. Low passage isogenic pre-stasis HMEC were used as a reference. CGH for the 184F lines was performed as described[5]. Karyology was performed as described[67].

Epigenetic Analysis of the hTERT Gene.

Methyl cytosine DNA immunoprecipitation (MeDIP), chromatin immunoprecipitation (ChIP), sample labeling and microarray hybridization were performed as described[68]. Microarray data were analyzed in R[66] as described[68] (GEO Accession number GSE48504). DNA methylation analysis by MassARRAY was performed as described in Novak P, Jensen T J, Garbe J C, Stampfer M R, Futscher B W. Step-wise DNA methylation changes are linked to escape from defined proliferation barriers and mammary epithelial cell immortalization. Cancer Research 2009; 67:5251-8, hereby incorporated by reference. Primer sequences are listed in Table 2; oligonucleotides were obtained from Integrated DNA Technologies.

Flow Cytometry.

CD227-FITC (BD Bioscience #559774, clone HMPV, 1:50), CD10-PE (BioLegend #312204, clone HI10a, 1:100), CD10-APC (BioLegend #312210, clone HI10a, 1:100), CD227-PE (BioLegend #355604, clone 16A, 1:100) were added to cells in media for 25 min on ice, washed in PBS and analyzed with a FACSCalibur (Becton Dickinson).

Western and ELISA Analysis.

Protein lysates for p16 and cyclin D1 were collected and processed as described[23] and 50 µg samples were resolved on a 4-12% Novex Bis/Tris gel (Invitrogen). Protein lysates for c-MYC were prepared using cell extraction buffer (Invitrogen cat# FNN0011) with protease inhibitors (Sigma Cat.# P2714). For detection of c-MYC by western blot, 25 µg of extracts were separated on a 4-12% Criterion TGX gel (Biorad). Separated proteins were transferred to Immobilon PVDF membrane (Millipore) and blocked in PBS 0.05% Tween20 with 1% nonfat milk for 1 hour. Binding of mAb 9E10 to c-MYC (Santa Cruz Biotech), mAb G175-405 to p16 (BD Biosciences) and mAb HD11, to cyclin D1 (Santa Cruz Biotech) was at 4° C. overnight followed by washing with PBS 0.05% Tween20. The membranes were incubated with goat anti mouse IgG Fc (HRP) conjugate (Abcam #ab97265, 1:5000) for 2 hours at room temperature, washed, and bound antibody was detected by chemiluminescence using the VersaDoc MP imaging system and quantified using Quantity-One software (Biorad). Beta-actin was detected with HRP conjugated mAb #AC-15 to beta-actin (Abcam). The total c-MYC ELISA assay (Invitrogen cat# KH02041) was performed following manufacturer's directions.

Immunohistochemistry and Immunofluorescence.

Immunohistochemical analysis for p16 was performed as described using the JC8[22] or MAB G175-405 antibody (BD Bioscience). Immunofluorescence was performed as described[23] using anti-K14 (1:500, Thermo, polyclonal) and anti-K19 (1:500, Sigma, clone A53-B/A2). Cells were counterstained with DAPI (Sigma) and imaged with an epifluorescence Axioplan microscope (Carl Zeiss).

HMEC were fixed in methanol:acetone (1:1) at −20° C. for 15 min, blocked with PBS, 5% normal goat serum, 0.1% Triton X-100, and incubated with K14 (Covance #PRB-155P-100, polyclonal rabbit, 1:1000) and K19 (Developmental Studies Hybridoma Bank, clone Troma-III, 1:20) overnight at 4° C., then visualized with fluorescent secondary antibodies (Invitrogen), and incubated for 2 h at room temperature. For 3-D cultures, HMEC were fixed in 4% paraformaldehyde for 30 min, blocked with PBS, 5% normal goat serum, 0.1% Triton X-100, and incubated with β-Catenin (BD Transduction Laboratories #610154, clone 14/Beta-Catenin, Mouse IgG1, 1:200) and Estrogen Receptor-a (Abcam #ab16660, clone SP1, rabbit monoclonal, 1:100) overnight at 4° C., then with secondaries for 2 hr at room temp.

FACS.

Cells were trypsinized and resuspended in ice-cold M87A media. Cells were stained for surface antigens using anti-CD227-FITC (Becton Dickinson, clone HMPV), anti-CD10-PE or -APC (BioLegend, clone HI10a), anti-CD24-Alexa488 (Biolegend, clone ML5), or anti-CD44-PE (BioLegend, clone IM7). Results were obtained on a FACS Calibur (Becton Dickenson) analysis platform as described in Garbe J C, Pepin F, Pelissier F A, Sputova K, Fridriksdottir A J, Guo D E, Villadsen R, Park M, Petersen O W, Borowsky A D, et al. Accumulation of multipotent progenitors with a basal differentiation bias during aging of human mammary epithelia. Cancer research 2012; 72:3687-701, hereby incorporated by reference.

Microarray Analysis.

Subconfluent cultures were harvested for RNA 24 h following feeding. Total RNA was harvested using TRIzol and purified using the miRNeasy Kit (Qiagen). RNA labeling and hybridization to Affymetrix Human Gene 1.0 ST Arrays, was performed according to the manufacturer's protocols. Microarray data were analyzed in R programming environment using the limma package.

Table 1:

Karyology of non-clonally immortalized lines at early passage. The 184Fp16sMY, 184Dp16sMY, 240Lp16sMY lines were non-clonally immortalized from non-clonal post-stasis cultures. The 184AaMY, 184BeMY, 184CeMY lines were non-clonally immortalized from clonal post-stasis cultures that had been exposed to the chemical carcinogen BaP. The karyotype of all three non-clonal p16sMY lines (184F, 184D, 240L), and one of the three BaP-MYC derived-lines (1.84CeMY), showed no abnormalities at early passage.

TABLE 1

Karyology of non-clonally immortalized lines at early passage

| Cell line, passage | Karyotype and Aberrations [# cells examined] |
|---|---|
| 184Fp16sMY, 16p | 46, XX normal diploid [10] |
| 184Dp16sMY, 16p | 46, XX normal diploid [12] |
| 240Lp16sMY, 16p | 46, XX normal diploid [11] |
| 184AaMY1, 17p | 46, XX normal diploid [14] |
|  | 47, XX, +i(1)(q10) [6] |
| 184BeMY, 11p | 45, X, add(X)(q28), −4, der(5)t(5; 15)(q11.2; q11.2), der(12)t(5; 12)(q11.2; q24.3), −15, +mar [cp16] |
| 184CeMY, 12p | 46, XX normal diploid [10] |

REFERENCES

1. Stampfer M R, Garbe J C, Labarge M A. An Integrated Human Mammary Epithelial Cell Culture System for Studying Carcinogenesis and Aging. In: Schatten H, ed. Cell and Molecular Biology of Breast Cancer. New York: Springer, 2013:323-61.
2. Greider C W. Telomeres, telomerase and senescence. BioEssays: news and reviews in molecular, cellular and developmental biology 1990; 12:363-9.
3. Seluanov A, Hine C, Bozzella M, Hall A, Sasahara T H, Ribeiro A A, Catania K C, Presgraves D C, Gorbunova V. Distinct tumor suppressor mechanisms evolve in rodent species that differ in size and lifespan. Aging Cell 2008; 7:813-23.
4. Meeker A K, Argani P. Telomere shortening occurs early during breast tumorigenesis: a cause of chromosome destabilization underlying malignant transformation? Journal of mammary gland biology and neoplasia 2004; 9:285-96.
5. Chin K, de Solorzano C O, Knowles D, Jones A, Chou W, Rodriguez E G, Kuo W L, Ljung B M, Chew K, Myambo K, et al. In situ analyses of genome instability in breast cancer. Nature genetics 2004; 36:984-8.
6. Garbe J C, Holst C R, Bassett E, Tlsty T, Stampfer M R. Inactivation of p53 function in cultured human mammary epithelial cells turns the telomere-length dependent senescence barrier from agonescence into crisis. Cell Cycle 2007; 6:1927-36.
7. Stampfer M R, Bartley J C. Induction of transformation and continuous cell lines from normal human mammary epithelial cells after exposure to benzo[a]pyrene. Proceedings of the National Academy of Sciences of the United States of America 1985; 82:2394-8.
8. Nonet G, Stampfer M R, Chin K, Gray J W, Collins C C, Yaswen P. The ZNF217 gene amplified in breast cancers promotes immortalization of human mammary epithelial cells. Cancer research 2001; 61:1250-4.
[19]9. Stampfer M R, Garbe J, Nijjar T, Wigington D, Swisshelm K, Yaswen P. Loss of p53 function accelerates acquisition of telomerase activity in indefinite lifespan human mammary epithelial cell lines. Oncogene 2003; 22:5238-51.
10. Garbe J C, Bhattacharya S, Merchant B, Bassett E, Swisshelm K, Feiler H S, Wyrobek A J, Stampfer M R. Molecular distinctions between stasis and telomere attrition senescence barriers shown by long-term culture of normal human mammary epithelial cells. Cancer research 2009; 69:7557-68.

11. Olsen C L, Gardie B, Yaswen P, Stampfer M R. Raf-1-induced growth arrest in human mammary epithelial cells is p16-independent and is overcome in immortal cells during conversion. Oncogene 2002; 21:6328-39.
12. Brenner A J, Stampfer M R, Aldaz C M. Increased p16INK4a expression with onset of senescence of human mammary epithelial cells and extended growth capacity with inactivation. Oncogene 1998; 17:199-205.
13. Romanov S R, Kozakiewicz B K, Holst C R, Stampfer M R, Haupt L M, Tlsty T D. Normal human mammary epithelial cells spontaneously escape senescence and acquire genomic changes. Nature 2001; 409:633-7.
14. Stampfer M R, Bodnar A, Garbe J, Wong M, Pan A, Villeponteau B, Yaswen P. Gradual phenotypic conversion associated with immortalization of cultured human mammary epithelial cells. Mol Biol Cell 1997; 8:2391-405.
15. Sherman M Y, Meng L, Stampfer M, Gabai V L, Yaglom J A. Oncogenes induce senescence with incomplete growth arrest and suppress the DNA damage response in immortalized cells. Aging Cell 2011; 10:949-61.
16. Stampfer M R, Bartley J C. Human mammary epithelial cells in culture: differentiation and transformation. Cancer Treat Res 1988; 40:1-24.
17. Brenner A J, Aldaz C M. Chromosome 9p allelic loss and p16/CDKN2 in breast cancer and evidence of p16 inactivation in immortal breast epithelial cells. Cancer Res 1995; 55:2892-5.
18. Novak P, Jensen T J, Garbe J C, Stampfer M R, Futscher B W. Step-wise DNA methylation changes are linked to escape from defined proliferation barriers and mammary epithelial cell immortalization. Cancer research 2009; 67:5251-8.
19. Hammond S L, Ham R G, Stampfer M R. Serum-free growth of human mammary epithelial cells: Rapid clonal growth in defined medium and extended serial passage with pituitary extract. Proc Natl Acad Sci USA 1984; 81:5435-9.
20. Severson P L, Vrba L, Stampfer M R, Futscher B W. (2014) Exome-wide mutation profile in benzo[a]pyrene-derived post-stasis and immortal human mammary epithelial cells. Mutation Res Genetic Tox and Env Mutagenesis: 775-776:48-54.
21. Kiyono T, Foster S A, Koop J I, McDougall J K, Galloway D A, Klingelhutz A J. Both Rb/p16INK4a inactivation and telomerase activity are required to immortalize human epithelial cells. Nature 1998; 396:84-8.
22. Stampfer M R, Garbe J, Levine G, Lichtsteiner S, Vasserot A P, Yaswen P. Expression of the telomerase catalytic subunit, hTERT, induces resistance to transforming growth factor beta growth inhibition in p16INK4A(−) human mammary epithelial cells. Proceedings of the National Academy of Sciences of the United States of America 2001; 98:4498-503.
23. Garbe J, Wong M, Wigington D, Yaswen P, Stampfer M R. Viral oncogenes accelerate conversion to immortality of cultured human mammary epithelial cells. Oncogene 1999; 18:2169-80.
24. Dang C V. MYC on the path to cancer. Cell 2012; 149:22-35.
25. Chen D, Kon N, Zhong J, Zhang P, Yu L, Gu W. Differential effects on ARF stability by normal versus oncogenic levels of c-Myc expression. Molecular cell 2013; 51:46-56.
26. Murphy D J, Junttila M R, Pouyet L, Karnezis A, Shchors K, Bui D A, Brown-Swigart L, Johnson L, Evan G I. Distinct thresholds govern Myc's biological output in vivo. Cancer cell 2008; 14:447-57.
27. Chin K, DeVries S, Fridly and J, Spellman P T, Roydasgupta R, Kuo W L, Lapuk A, Neve R M, Qian Z, Ryder T, et al. Genomic and transcriptional aberrations linked to breast cancer pathophysiologies. Cancer cell 2006; 10:529-41.
28. Simon J A, Kingston R E. Mechanisms of polycomb gene silencing: knowns and unknowns. Nature reviews Molecular cell biology 2009; 10:697-708.
29. Guenther M G, Levine S S, Boyer L A, Jaenisch R, Young R A. A chromatin landmark and transcription initiation at most promoters in human cells. Cell 2007; 130:77-88.
30. Bloushtain-Qimron N, Yao J, Snyder E L, Shipitsin M, Campbell L L, Mani S A, Hu M, Chen H, Ustyansky V, Antosiewicz J E, et al. Cell type-specific DNA methylation patterns in the human breast. Proceedings of the National Academy of Sciences of the United States of America 2008; 105:14076-81.
31. Park S Y, Gonen M, Kim H J, Michor F, Polyak K. Cellular and genetic diversity in the progression of in situ human breast carcinomas to an invasive phenotype. The Journal of clinical investigation 2010; 120:636-44.
32. Rheinwald J G, Hahn W C, Ramsey M R, Wu J Y, Guo Z, Tsao H, De Luca M, Catricala C, O'Toole K M. A two-stage, p16$^{INK4a}$- and p53-dependent keratinocyte senescence mechanism that limits replicative potential independent of telomere status. Mol Cell Biol 2002; 22:5157-72.
33. Carey L A, Hedican C A, Henderson G S, Umbricht C B, Dome J S, Varon D, Sukumar S. Careful histological confirmation and microdissection reveal telomerase activity in otherwise telomerase-negative breast cancers. Clinical cancer research: an official journal of the American Association for Cancer Research 1998; 4:435-40.
34. Yashima K, Milchgrub S, Gollahon L S, Maitra A, Saboorian M H, Shay J W, Gazdar A F. Telomerase enzyme activity and RNA expression during the multistage pathogenesis of breast carcinoma. Clinical cancer research: an official journal of the American Association for Cancer Research 1998; 4:229-34.
35. Subhawong A P, Heaphy C M, Argani P, Konishi Y, Kouprina N, Nassar H, Vang R, Meeker A K. The alternative lengthening of telomeres phenotype in breast carcinoma is associated with HER-2 overexpression. Modern pathology: an official journal of the United States and Canadian Academy of Pathology, Inc 2009; 22:1423-31.
36. Meeker A K, Hicks J L, E. A. P, March G E, Bennett C J, Delannoy M J, De Marzo A M. Telomere shortening is an early somatic DNA alteration in human prostate tumorigenesis. Cancer Res 2002; 62:6405-9.
37. Chene G, Tchirkov A, Pierre-Eymard E, Dauplat J, Raoelfils I, Cayre A, Watkin E, Vago P, Penault-Llorca F. Early telomere shortening and genomic instability in tubo-ovarian preneoplastic lesions. Clinical cancer research: an official journal of the American Association for Cancer Research 2013; 19:2873-82.
38. Blasco M A. Telomerase beyond telomeres. Nature reviews Cancer 2002; 2:627-32.
39. Suram A, Herbig U. The replicometer is broken: telomeres activate cellular senescence in response to genotoxic stresses. Aging Cell 2014.
40. Mukherjee S, Firpo E J, Wang Y, Roberts J M. Separation of telomerase functions by reverse genetics. Proceedings of the National Academy of Sciences of the United States of America 2011.

41. Horikawa I, Chiang Y J, Patterson T, Feigenbaum L, Leem S H, Michishita E, Larionov V, Hodes R J, Barrett J C. Differential cis-regulation of human versus mouse TERT gene expression in vivo: Identification of a human-specific repressive element. Proceedings of the National Academy of Sciences of the United States of America 2005; 102:18437-42.

42. O'Hagan R C, Chang S, Maser R S, Mohan R, Artandi S E, Chin L, DePinho R A. Telomere dysfunction provokes regional amplification and deletion in cancer genomes. Cancer cell 2002; 2:149-55.

43. Zhang J, Pickering C R, Holst C R, Gauthier M L, Tlsty T D. p16INK4a modulates p53 in primary human mammary epithelial cells. Cancer research 2006; 66:10325-31.

44. Keller P J, Arendt L M, Skibinski A, Logvinenko T, Klebba I, Dong S, Smith A E, Prat A, Perou C M, Gilmore H, et al. Defining the cellular precursors to human breast cancer. Proceedings of the National Academy of Sciences of the United States of America 2012; 109:2772-7.

45. Lim E, Vaillant F, Wu D, Forrest N C, Pal B, Hart A H, Asselin-Labat M L, Gyorki D E, Ward T, Partanen A, et al. Aberrant luminal progenitors as the candidate target population for basal tumor development in BRCA1 mutation carriers. Nature medicine 2009; 15:907-13.

46. Molyneux G, Geyer F C, Magnay F A, McCarthy A, Kendrick H, Natrajan R, Mackay A, Grigoriadis A, Tutt A, Ashworth A, et al. BRCA1 basal-like breast cancers originate from luminal epithelial progenitors and not from basal stem cells. Cell stem cell 2010; 7:403-17.

47. Proia T A, Keller P J, Gupta P B, Klebba I, Jones A D, Sedic M, Gilmore H, Tung N, Naber S P, Schnitt S, et al. Genetic predisposition directs breast cancer phenotype by dictating progenitor cell fate. Cell stem cell 2011; 8:149-63.

48. Garbe J C, Pepin F, Pelissier F A, Sputova K, Fridriksdottir A J, Guo D E, Villadsen R, Park M, Petersen O W, Borowsky A D, et al. Accumulation of multipotent progenitors with a basal differentiation bias during aging of human mammary epithelia. Cancer research 2012; 72:3687-701.

49. Wood L D, Parsons D W, Jones S, Lin J, Sjoblom T, Leary R J, Shen D, Boca S M, Barber T, Ptak J, et al. The genomic landscapes of human breast and colorectal cancers. Science 2007; 318:1108-13.

50. Loeb L A. Human cancers express mutator phenotypes: origin, consequences and targeting. Nature reviews Cancer 2011; 11:450-7.

51. Negrini S, Gorgoulis V G, Halazonetis T D. Genomic instability—an evolving hallmark of cancer. Nature reviews Molecular cell biology 2010; 11:220-8.

52. Kolodner R D, Cleveland D W, Putnam C D. Cancer. Aneuploidy drives a mutator phenotype in cancer. Science 2011; 333:942-3.

53. Storchova Z, Pellman D. From polyploidy to aneuploidy, genome instability and cancer. Nature reviews Molecular cell biology 2004; 5:45-54.

54. Soler D, Genesca A, Arnedo G, Egozcue J, Tusell L. Telomere dysfunction drives chromosomal instability in human mammary epithelial cells. Genes, chromosomes & cancer 2005; 44:339-50.

55. Pampalona J, Frias C, Genesca A, Tusell L. Progressive telomere dysfunction causes cytokinesis failure and leads to the accumulation of polyploid cells. PLoS genetics 2012; 8:e1002679.

56. Warnberg F, Nordgren H, Bergkvist L, Holmberg L. Tumour markers in breast carcinoma correlate with grade rather than with invasiveness. British journal of cancer 2001; 85:869-74.

57. Miron A, Varadi M, Carrasco D, Li H, Luongo L, Kim H J, Park S Y, Cho E Y, Lewis G, Kehoe S, et al. PIK3CA mutations in in situ and invasive breast carcinomas. Cancer research 2010; 70:5674-8.

58. Ma X J, Salunga R, Tuggle J T, Gaudet J, Enright E, McQuary P, Payette T, Pistone M, Stecker K, Zhang B M, et al. Gene expression profiles of human breast cancer progression. Proceedings of the National Academy of Sciences of the United States of America 2003; 100:5974-9.

59. Espina V, Liotta L A. What is the malignant nature of human ductal carcinoma in situ? Nature reviews Cancer 2011; 11:68-75.

60. Cipriano R, Kan C E, Graham J, Danielpour D, Stampfer M, Jackson M W. TGF-beta signaling engages an ATM-CHK2-p53-independent RAS-induced senescence and prevents malignant transformation in human mammary epithelial cells. Proceedings of the National Academy of Sciences of the United States of America 2011; 108:8668-73.

61. Zinn R L, Pruitt K, Eguchi S, Baylin S B, Herman J G. hTERT is expressed in cancer cell lines despite promoter DNA methylation by preservation of unmethylated DNA and active chromatin around the transcription start site. Cancer research 2007; 67:194-201.

62. Renaud S, Loukinov D, Alberti L, Vostrov A, Kwon Y W, Bosman F T, Lobanenkov V, Benhattar J. BORIS/CTCFL-mediated transcriptional regulation of the hTERT telomerase gene in testicular and ovarian tumor cells. Nucleic acids research 2011; 39:862-73.

63. Narita M, Nunez S, Heard E, Lin A W, Hearn S A, Spector D L, Hannon G J, Lowe S W. Rb-mediated heterochromatin formation and silencing of E2F target genes during cellular senescence. Cell 2003; 113:703-16.

64. Eilers M, Picard D, Yamamoto K R, Bishop J M. Chimaeras of myc oncoprotein and steroid receptors cause hormone-dependent transformation of cells. Nature 1989; 340:66-8.

65. Counter C M, Hahn W C, Wei W, Caddle S D, Beijersbergen R L, Lansdorp P M, Sedivy J M, Weinberg R A. Dissociation among in vitro telomerase activity, telomere maintenance, and cellular immortalization. Proc Natl Acad Sci USA 1998; 95:14723-8.

66. R Development Core Team. R: A Language and Environment for Statistical Computing. R Foundation for Statistical Computing. Vienna, Austria, 2011.

67. Barch M J. The AGT Cytogenetics Laboratory Manual, 3rd edition. New York: Lippincott-Raven, 1997.

68. Vrba L, Garbe J C, Stampfer M R, Futscher B W. Epigenetic regulation of normal human mammary cell type-specific miRNAs. Genome Res 2011; 21:2026-37.

The above examples are provided to illustrate the invention but not to limit its scope. Other variants of the invention will be readily apparent to one of ordinary skill in the art and are encompassed by the appended claims. All publications, accessions, references, databases, and patents cited herein are hereby incorporated by reference for all purposes.

What is claimed is:

1. A method of identifying an agent that prevents cell immortalization, comprising:
   culturing pre-stasis epithelial cells in a low stress-inducing medium;
   measuring the level of cyclin-dependent kinase inhibitor 2A (p16) in the pre-stasis epithelial cells to determine status of induction of p16 in the pre-stasis epithelial cells;
   prior to induction of p16 in the pre-stasis epithelial cells, introducing into the pre-stasis epithelial cells a polynucleotide that prevents the retinoblastoma protein (RB) from staying in an active form, to produce post-stasis epithelial cells, wherein the polynucleotide that prevents RB from staying in an active form is a p16 shRNA;
   prior to telomere dysfunction, introducing:
      an agent; and
      a polynucleotide that induces telomerase activity, wherein the polynucleotide that induces telomerase activity encodes c-MYC,
   into the post-stasis epithelial cells; and
   subsequent to introducing the agent and the polynucleotide that induces telomerase activity, culturing the epithelial cells to determine whether the cells are immortalized, wherein when the cells are not immortalized, the agent is identified as an agent that prevents cell immortalization, wherein the method does not introduce gross genomic errors into the epithelial cells.

2. The method according to claim 1, wherein the agent is a polynucleotide or a small molecule.

3. The method according to claim 1, wherein the low stress-inducing medium is M87A medium.

4. The method according to claim 3, wherein the pre-stasis epithelial cells are pre-stasis human mammary epithelial cells (HMEC).

5. The method according to claim 1, wherein the method further comprises introducing an additional polynucleotide into the pre-stasis epithelial cells that targets RB expression or inactivates p53.

6. The method according to claim 5, wherein the additional polynucleotide comprises an RB shRNA.

7. The method according to claim 5, wherein the additional polynucleotide comprises a p53 shRNA or a p53 genetic suppressor element.

8. The method according to claim 1, wherein the pre-stasis epithelial cells are pre-stasis mammary epithelial cells.

9. The method according to claim 8, wherein the pre-stasis mammary epithelial cells are pre-stasis human mammary epithelial cells (HMEC).

* * * * *

SEQUENCE LISTING

<160> NUMBER OF SEQ ID NOS: 7

<210> SEQ ID NO 1
<211> LENGTH: 1800
<212> TYPE: DNA
<213> ORGANISM: Homo sapiens

<400> SEQUENCE: 1

```
atgcccctca acgttagctt caccaacagg aactatgacc tcgactacga ctcggtgcag      60
ccgtatttct actgcgacga ggaggagaac ttctaccagc agcagcagca gagcgagctg     120
cagcccccgg cgcccagcga ggatatctgg aagaaattcg agctgctgcc caccccgccc     180
ctgtccccta gccgccgctc cgggctctgc tcgccctcct acgttgcggt cacacccttc     240
tcccttcggg gagacaacga cggcggtggc gggagcttct ccacgccgga ccagctggag     300
atggtgaccg agctgctggg aggagacatg gtgaaccaga gtttcatctg cgacccggac     360
gacgagacct tcatcaaaaa catcatcatc caggactgta tgtggagcgg cttctcggcc     420
gccgccaagc tcgtctcaga gaagctggcc tcctaccagg ctgcgcgcaa agacagcggc     480
agcccgaacc ccgcccgcgg ccacagcgtc tgctccacct ccagcttgta cctgcaggat     540
ctgagcgccg ccgcctcaga gtgcatcgac ccctcggtgg tcttcccta ccctctcaac     600
gacagcagct cgcccaagtc ctgcgcctcg caagactcca cgccttctc tccgtcctcg     660
gattctctgc tctcctcgac ggagtcctcc ccgcagggca gccccgagcc cctggtgctc     720
catgaggaga caccgcccac caccagcagc gactctgagg aggaacaaga agatgaggaa     780
gaaatcgatg ttgtttctgt ggaaaagagg caggctcctg gcaaaaggtc agagtctgga     840
tcaccttctg ctggaggcca cagcaaacct cctcacagcc cactggtcct caagaggtgc     900
cacgtctcca cacatcagca caactacgca gcgcctccct ccactcggaa ggactatcct     960
gctgccaaga gggtcaagtt ggacagtgtc agagtcctga cagatcag caacaaccga    1020
aaatgcacca gccccaggtc ctcggacacc gaggagaatg tcaagaggcg aacacacaac    1080
gtcttggagc gccagaggag gaacgagcta aaacggagct tttttgccct gcgtgaccag    1140
atcccggagt tggaaaacaa tgaaaaggcc cccaaggtag ttatccttaa aaaagccaca    1200
gcatacatcc tgtccgtcca agcagaggag caaaagctca tttctgaaga ggacttgttg    1260
cggaaacgac gagaacagtt gaaacacaaa cttgaacagc tacggaactc ttgtgcgtaa    1320
ggaaaagtaa ggaaaacgat tccttctaac agaaatgtcc tgagcaatca cctatgaact    1380
tgtttcaaat gcatgatcaa atgcaacctc acaaccttgg ctgagtcttg agactgaaag    1440
atttagccat aatgtaaact gcctcaaatt ggactttggg cataaaagaa cttttttatg    1500
cttaccatct tttttttttc tttaacagat ttgtatttaa gaattgtttt taaaaaattt    1560
taagatttac acaatgtttc tctgtaaata ttgccattaa atgtaaataa ctttaataaa    1620
acgtttatag cagttacaca gaatttcaat cctagtatat agtacctagt attataggta    1680
ctataaaccc taatttttt tatttaagta cattttgctt tttaaagttg attttttcct    1740
attgttttta gaaaaaataa aataactggc aaatatatca ttgagccaaa tcttaaaaaa    1800
```

<210> SEQ ID NO 2
<211> LENGTH: 439
<212> TYPE: PRT
<213> ORGANISM: Homo sapiens

<400> SEQUENCE: 2

Met Pro Leu Asn Val Ser Phe Thr Asn Arg Asn Tyr Asp Leu Asp Tyr

```
1               5                   10                  15
Asp Ser Val Gln Pro Tyr Phe Tyr Cys Asp Glu Glu Asn Phe Tyr
                20                  25                  30
Gln Gln Gln Gln Gln Ser Glu Leu Gln Pro Pro Ala Pro Ser Glu Asp
                35                  40                  45
Ile Trp Lys Lys Phe Glu Leu Leu Pro Thr Pro Pro Leu Ser Pro Ser
                50                  55                  60
Arg Arg Ser Gly Leu Cys Ser Pro Ser Tyr Val Ala Val Thr Pro Phe
65                  70                  75                  80
Ser Leu Arg Gly Asp Asn Asp Gly Gly Gly Ser Phe Ser Thr Ala
                85                  90                  95
Asp Gln Leu Glu Met Val Thr Glu Leu Leu Gly Gly Asp Met Val Asn
                100                 105                 110
Gln Ser Phe Ile Cys Asp Pro Asp Asp Glu Thr Phe Ile Lys Asn Ile
                115                 120                 125
Ile Ile Gln Asp Cys Met Trp Ser Gly Phe Ser Ala Ala Ala Lys Leu
                130                 135                 140
Val Ser Glu Lys Leu Ala Ser Tyr Gln Ala Ala Arg Lys Asp Ser Gly
145                 150                 155                 160
Ser Pro Asn Pro Ala Arg Gly His Ser Val Cys Ser Thr Ser Ser Leu
                165                 170                 175
Tyr Leu Gln Asp Leu Ser Ala Ala Ala Ser Glu Cys Ile Asp Pro Ser
                180                 185                 190
Val Val Phe Pro Tyr Pro Leu Asn Asp Ser Ser Ser Pro Lys Ser Cys
                195                 200                 205
Ala Ser Gln Asp Ser Ser Ala Phe Ser Pro Ser Ser Asp Ser Leu Leu
                210                 215                 220
Ser Ser Thr Glu Ser Ser Pro Gln Gly Ser Pro Glu Pro Leu Val Leu
225                 230                 235                 240
His Glu Glu Thr Pro Pro Thr Thr Ser Ser Asp Ser Glu Glu Glu Gln
                245                 250                 255
Glu Asp Glu Glu Glu Ile Asp Val Val Ser Val Glu Lys Arg Gln Ala
                260                 265                 270
Pro Gly Lys Arg Ser Glu Ser Gly Ser Pro Ser Ala Gly Gly His Ser
                275                 280                 285
Lys Pro Pro His Ser Pro Leu Val Leu Lys Arg Cys His Val Ser Thr
                290                 295                 300
His Gln His Asn Tyr Ala Ala Pro Pro Ser Thr Arg Lys Asp Tyr Pro
305                 310                 315                 320
Ala Ala Lys Arg Val Lys Leu Asp Ser Val Arg Val Leu Arg Gln Ile
                325                 330                 335
Ser Asn Asn Arg Lys Cys Thr Ser Pro Arg Ser Ser Asp Thr Glu Glu
                340                 345                 350
Asn Val Lys Arg Arg Thr His Asn Val Leu Glu Arg Gln Arg Arg Asn
                355                 360                 365
Glu Leu Lys Arg Ser Phe Phe Ala Leu Arg Asp Gln Ile Pro Glu Leu
                370                 375                 380
Glu Asn Asn Glu Lys Ala Pro Lys Val Val Ile Leu Lys Lys Ala Thr
385                 390                 395                 400
Ala Tyr Ile Leu Ser Val Gln Ala Glu Glu Gln Lys Leu Ile Ser Glu
                405                 410                 415
Glu Asp Leu Leu Arg Lys Arg Arg Glu Gln Leu Lys His Lys Leu Glu
                420                 425                 430
```

Gln Leu Arg Asn Ser Cys Ala
        435

<210> SEQ ID NO 3
<211> LENGTH: 30
<212> TYPE: DNA
<213> ORGANISM: Artificial sequence
<220> FEATURE:
<223> OTHER INFORMATION: Synthetic p16 shRNA sequence

<400> SEQUENCE: 3
ctgcccaacg caccgaatag ttacggtcgg                               30

<210> SEQ ID NO 4
<211> LENGTH: 35
<212> TYPE: DNA
<213> ORGANISM: Artificial sequence
<220> FEATURE:
<223> OTHER INFORMATION: TERT promoter MassARRAY synthetic sequence
      TERT_UP_10F

<400> SEQUENCE: 4
aggaagagag ggtattttgt ttggtagatg aggtt                         35

<210> SEQ ID NO 5
<211> LENGTH: 57
<212> TYPE: DNA
<213> ORGANISM: Artificial sequence
<220> FEATURE:
<223> OTHER INFORMATION: TERT promoter MassARRAY synthetic sequence
      TERT_UP_T7R

<400> SEQUENCE: 5
cagtaatacg actcactata gggagaaggc tccctaataa caaaaacaat tcacaaa   57

<210> SEQ ID NO 6
<211> LENGTH: 35
<212> TYPE: DNA
<213> ORGANISM: Artificial sequence
<220> FEATURE:
<223> OTHER INFORMATION: TERT promoter Mass ARRAY synthetic sequence
      TERT_TSS_10F

<400> SEQUENCE: 6
aggaagagag agggttttta tattatggtt ttttt                         35

<210> SEQ ID NO 7
<211> LENGTH: 54
<212> TYPE: DNA
<213> ORGANISM: Artificial sequence
<220> FEATURE:
<223> OTHER INFORMATION: TERT promoter MassARRAY synthetic sequence
      TERT_TSS_T7R

<400> SEQUENCE: 7
cagtaatacg actcactata gggagaaggc tacaccaaac actaaaccac caac     54